United States Patent [19]

Schoenig, Jr. et al.

[11] Patent Number: 4,496,056
[45] Date of Patent: Jan. 29, 1985

[54] AUTOMATED INSPECTION SYSTEM

[75] Inventors: Frederick C. Schoenig, Jr., Wilmington; Leonard N. Grossman, Wrightsville Beach, both of N.C.; Ching C. Lai, Pleasanton, Calif.; William Masaitis, Castle Hayne; Robert O. Canada, Wilmington, both of N.C.

[73] Assignee: General Electric Company, San Jose, Calif.

[21] Appl. No.: 361,933

[22] Filed: Mar. 25, 1982

[51] Int. Cl.$^3$ .................. B07C 5/02; B07C 5/342
[52] U.S. Cl. ................... 209/539; 209/579; 209/587; 209/586; 209/654; 209/916; 356/237; 356/394; 356/398; 364/507
[58] Field of Search .............. 209/539, 576–579, 209/585–587, 651–654, 701, 903, 914, 916, 921, 209/934, 936; 356/394, 398, 426, 445, 448, 237; 364/552, 555, 507; 198/425, 410, 411, 461, 738, 198/739, 372

[56] References Cited

U.S. PATENT DOCUMENTS

| | | | |
|---|---|---|---|
| 3,355,014 | 11/1967 | Howles | 209/587 |
| 4,155,455 | 5/1979 | Spierer et al. | 209/701 X |
| 4,349,112 | 9/1982 | Wilks et al. | 209/579 X |
| 4,377,238 | 3/1983 | Wilks et al. | 209/564 X |

Primary Examiner—Robert B. Reeves
Assistant Examiner—Edward M. Wacyra
Attorney, Agent, or Firm—Samuel E. Turner; Fred Jacob; Ernest F. Chapman

[57] ABSTRACT

An automated inspection station comprises a pair of rotating rollers for supporting a collected group of pellets. A pusher drops in behind the group to urge the entire group forward. The rotating rollers cause the entire group of pellets to spin in unison as the pellets pass through an optical inspection station. The optical inspection station comprises a light source, diverging and collimating lenses to illuminate each rotating pellet in turn. Signals are generated by at least two arrays of photodiodes in response to light reflected from the surface of the pellets. Circuitry normalizes the signals of the respective diodes for variations unrelated to pellet surface features. The signals are analyzed to ascertain conformance of each pellet to length, cylindricality diameter and surface reflectivity requirements. A pellet sorter diverts unacceptable pellets from the path, while the acceptable pellets are transported to a collection station. Additional circuitry generates known timing pulses which control the axial speed of the pellets advancing past the inspection station, as well as for synchronizing and correlating the collected data with the respective advancing pellets. The number of threshold changes and their location on the pellet help determine conformance to the above criteria.

7 Claims, 46 Drawing Figures

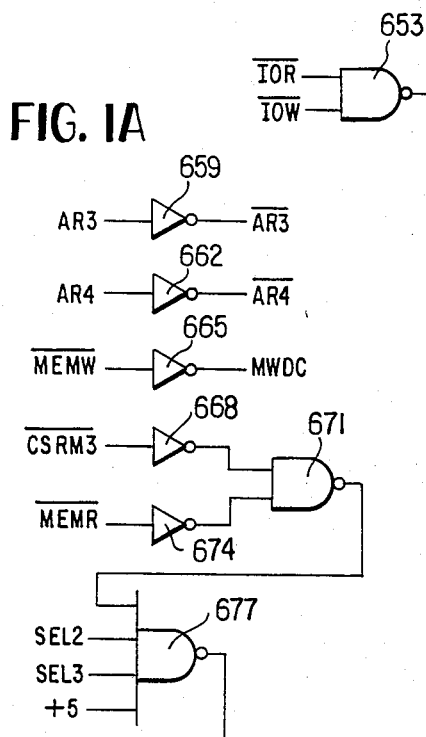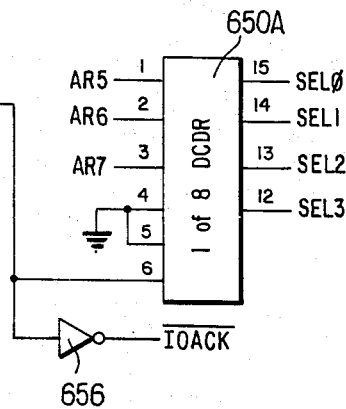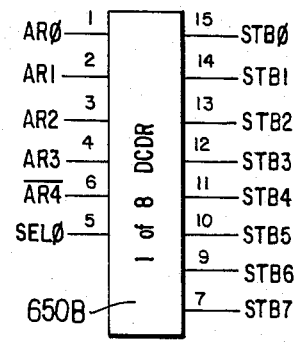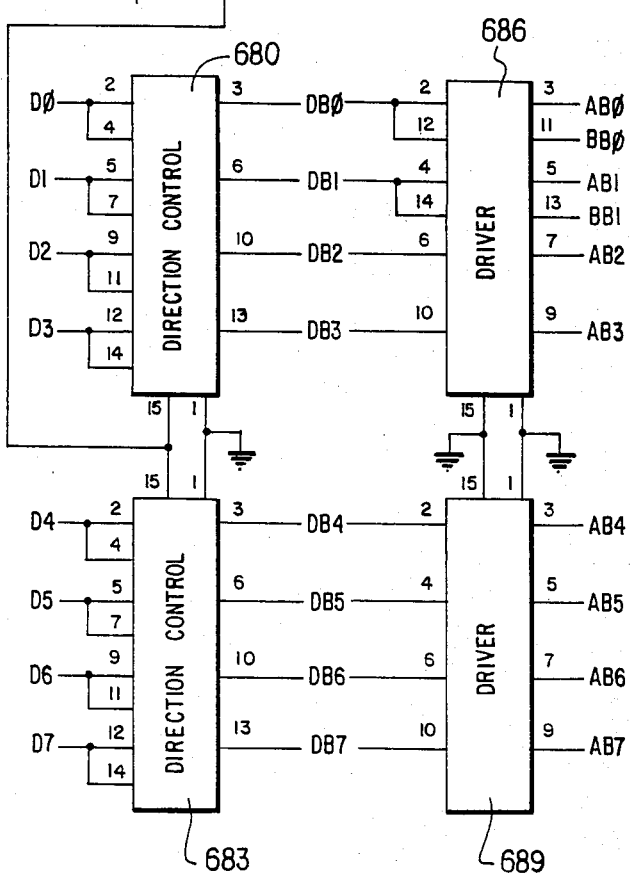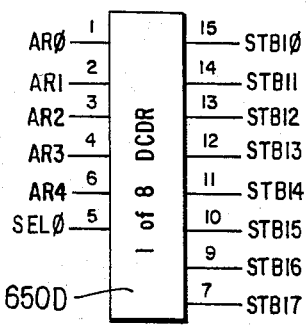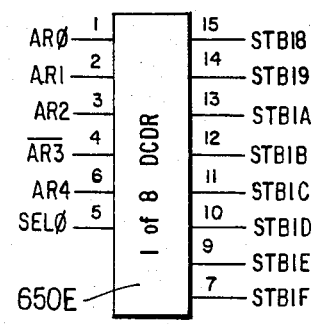

FIG. 19
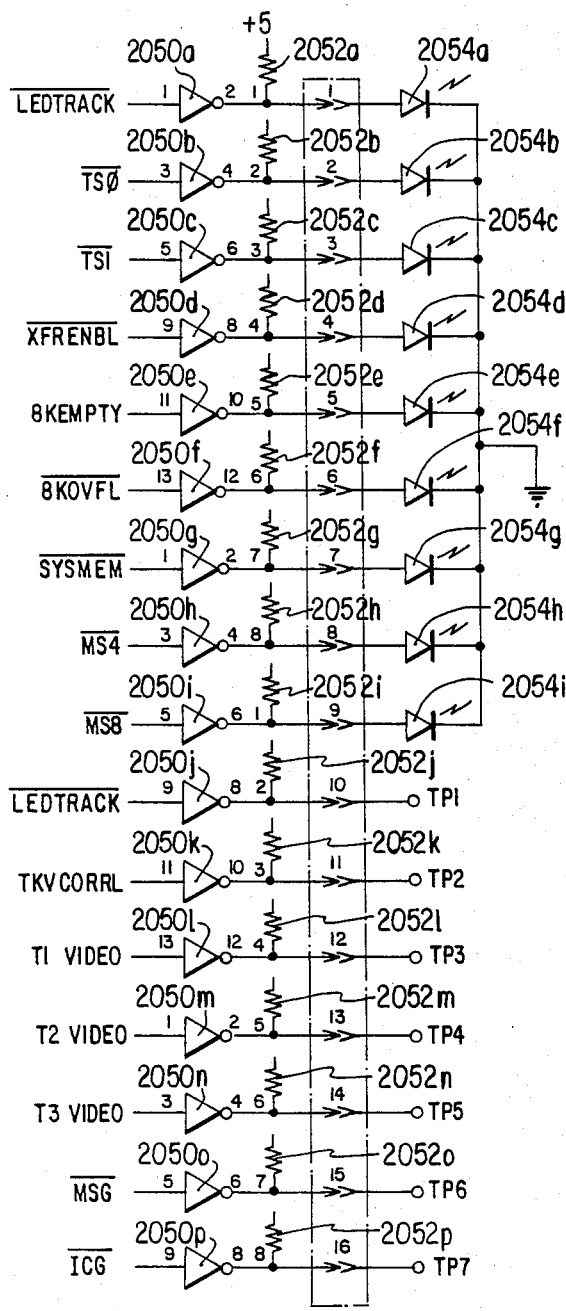
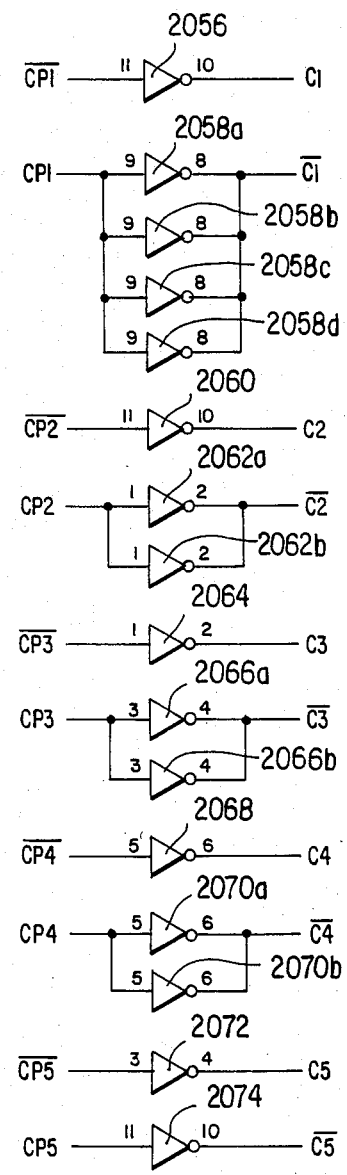

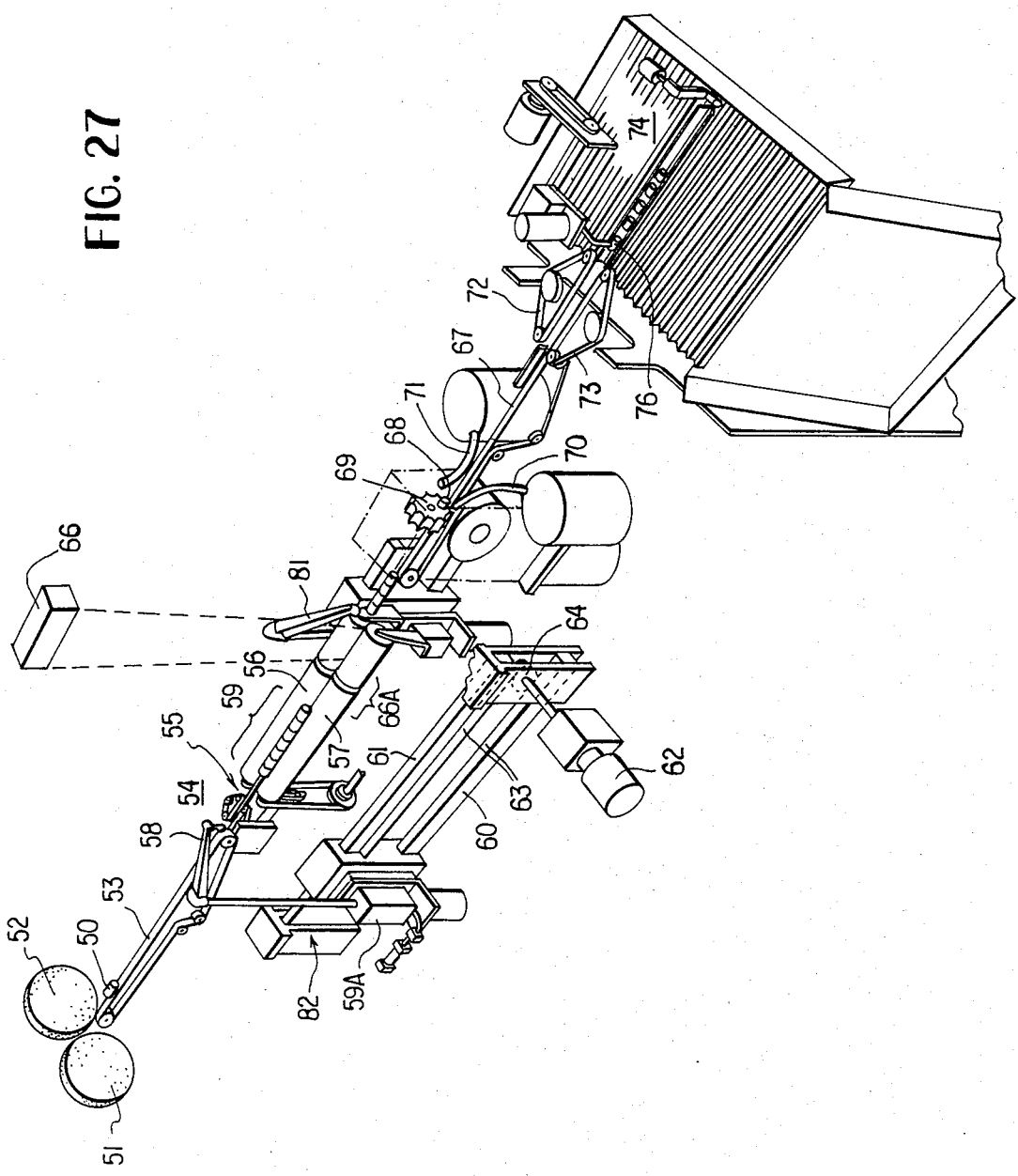

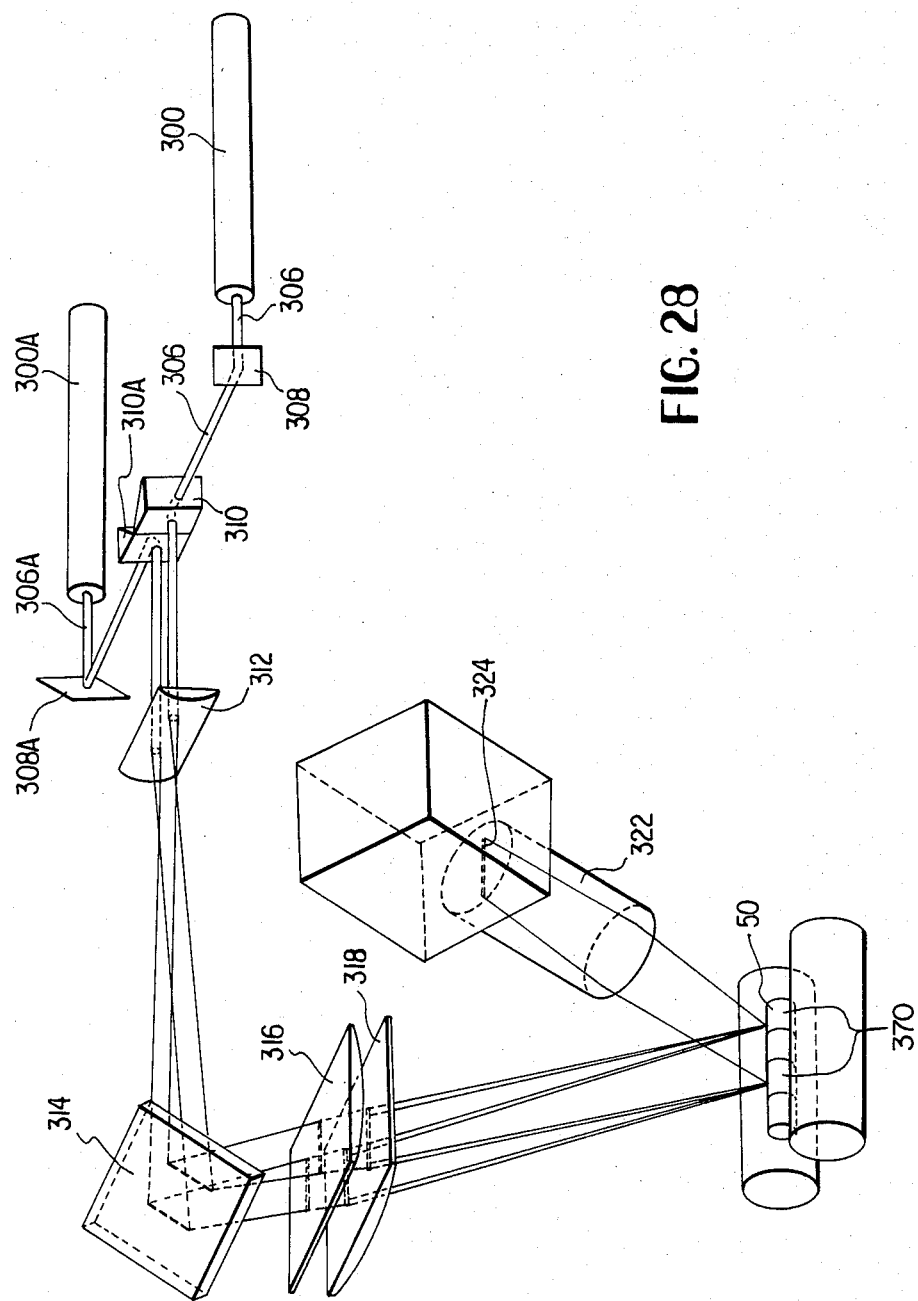

AUTOMATED INSPECTION SYSTEM

The present invention relates in general to new and improved inspection systems, in particular to an automated inspection system for inspecting various physical characteristics of objects, such as a succession of cylindrically shaped objects, for conformance to predetermined criteria.

CROSS REFERENCE TO RELATED APPLICATION

The automated inspection system can utilize an "Optical Inspection System" such as that discussed in Copending application Ser. No. 362,992, filed Mar. 25, 1982, assigned to General Electric Company, and expressly incorporated herein by reference.

Copending application Ser. No. 361,993, filed Mar. 25, 1982 assigned to General Electric Company and expressly incorporated herein by reference shows a "Transport Apparatus" specifically adapted for utilization with the present invention. The incorporated disclosure details aspects of controlling angular velocity of pellets undergoing inspection beginning on Page 15 of the application.

Copending application Ser. No. 362,046, filed Mar. 25, 1982, and assigned to General Electric company discloses a "Tray loader Method and apparatus for Nuclear Fuel Pellets" suitable for collecting pellets after inspection. The specific method and apparatus disclosed provides for weighing groups of pellets after collection into a suitable container.

BACKGROUND OF THE INVENTION

The fuel rods in use in nuclear reactors commonly use cylindrical pellets composed of uranium dioxide bound in a matrix material. Following grinding the pellets to their final shape and before they are stacked in the fuel rods, the pellets must be inspected for flaws and other anomalies, for conformance to predetermined length measurement and conformance to a cylindrical shape.

In use, the pellets are packed tightly in metallic tubes in the nuclear reactor. The metallic tubes dissipate heat generated by the pellets into a surrounding medium. Thus, a good heat-exchange relationship must exist at the pellet-metallic tubing interface and this is provided when the pellet's surfaces conform to the cylindrical shape of the tubing. Inspection for conformance to this and other criteria is conventionally carried out manually by skilled operators. Prior art automated optical equipment is believed to be limited to equipment in experimental stages.

One approach used in prior art apparatus for optically inspecting such pellets employs mechanical hands to carry individual pellets from a stream of pellets to an inspection station. At the inspection station each pellet is rotated in order to completely expose it to view and other mechanical hands transport it back to the pellet stream where sorting is carried out to deliver the pellets to selected locations.

The prior art apparatus described requires complicated mechanical linkages to operate the hands, and the speed of inspection is limited by the speed with which the hands can move the pellet out of and back into the pellet stream, respectively. Further, since the pellets are composed of a highly abrasive material, the roller supports on which the pellets are rotated are rapidly abraded away, and the useful lifetime of each is limited. Often the rollers are abraded unevenly and develop surface ridges. These ridges can cause the pellets to jitter or chatter during rotation, thereby rendering the inspection equipment incapable of obtaining a clear pellet image and hence incapable of an accurate measurement.

Such apparatus is also prone to problems of pellet identification. It has been found difficult to correlate information concerning the actual physical location of a particular pellet with the measured information concerning the same pellet obtained by the inspection equipment. Such a situation produces difficulties in coordinating the mechanical hands with the rest of the transport, thus causing further delays in pellet viewing and sorting.

Another approach used by the prior art for optically inspecting pellets employs a camera which moves along a track located above rollers that support a rotating string of pellets. Such apparatus also causes the rollers to wear unevenly, thus causing eventual unacceptably large vibrations and jitter of the rotating pellets.

Both types of equipment discussed above are prone to introduce dust into the air and to create a dust-laden atmosphere within which both types of inspection devices are required to function. The dust particles lodged in the mechanical linkages of either the moving camera or the mechanical hands are apt to cause vibrations and other objectional phenomena.

Where the number of characteristics checked is high, a large amount of data is extracted from the optical inspection of each pellet, which must be stored and processed. In order to obtain high throughput for the inspection process, the data must be processed rapidly so that sorting of the succession of pellets may be carried on substantially concurrently with their inspection. At the current state of the art, such data processing capability is available only at a cost sufficiently high to price the inspection system capable of meeting these performance requirements out of range for most purposes.

OBJECTS OF THE INVENTION

It is an object of the present invention to provide a new and improved automated pellet inspection system which avoids the disadvantages inherent in prior art inspection systems of this type.

It is another object of the present invention to provide a new and improved automated pellet inspection system which transports pellets in a substantially continuous path from a pellet source past an inspection station and a sorter to a collection station.

It is a further object of the present invention to provide a new and improved automated inspection system which achieves a high degree of throughput without denigrating the reliability of the inspection process.

It is an additional object of the present invention to provide a new and improved pellet inspection system which provides increased stability of the pellets during inspection.

It is still another object of the present invention to provide a new and improved automated pellet inspection system for optically inspecting the surface characteristics of cylindrical pellets.

It is still a further object of the present invention to provide an automated pellet inspection system for optically inspecting pellet diameter and roundness and which locates an interface between abutting pellets by correlating the locations of low amplitude reflected signals.

It is still an additional object of the present invention to provide a new and improved automated pellet inspection system which is capable of locating the interfaces between successive abutting pellets by optical means from each pellet and associates the data into discrete groups.

It is yet another object of the present invention to provide a new and improved automated pellet inspection system which rotates stacks of abutted pellets while moving the stacks in a lateral direction to permit viewing of each pellet in its entirety by an inspection station.

It is yet a further object of the present invention to provide a new and improved automated pellet inspection system which generates signals from the optical inspection of the pellets relative to pellet characteristics and which compresses the data extracted from these signals to collapse the rate at which data is transmitted to subsequent data processing circuitry.

It is yet an additional object of the present invention to provide a new and improved automated pellet inspection system which provides a tracking gate to bracket and thereby identify data derived from respective pellets.

It is an object of the present invention to provide a new and improved automated inspection system wherein signals derived from the pellet inspection process are modified to compensate for factors extraneous to the pellet characteristics of interest.

Still another object of the invention is to provide a new and improved automated inspection system which is more economical and more cost effective than heretofore available inspection systems of this type.

BRIEF DESCRIPTION OF THE DRAWINGS

FIGS. 1A through 1F illustrate decoders for performing strobing functions and drivers for accommodating integrated circuit fan-out.

FIG. 19 illustrates circuitry for generating signals indicative of the operation of preprocessor circuitry.

FIG. 27 illustrates a preferred embodiment of pellet transport and inspection aparatus.

FIG. 28 illustrates in schematic form apparatus for optically generating signals indicative of pellet surface fea- tures.

SUMMARY OF THE INVENTION

Figure 1:
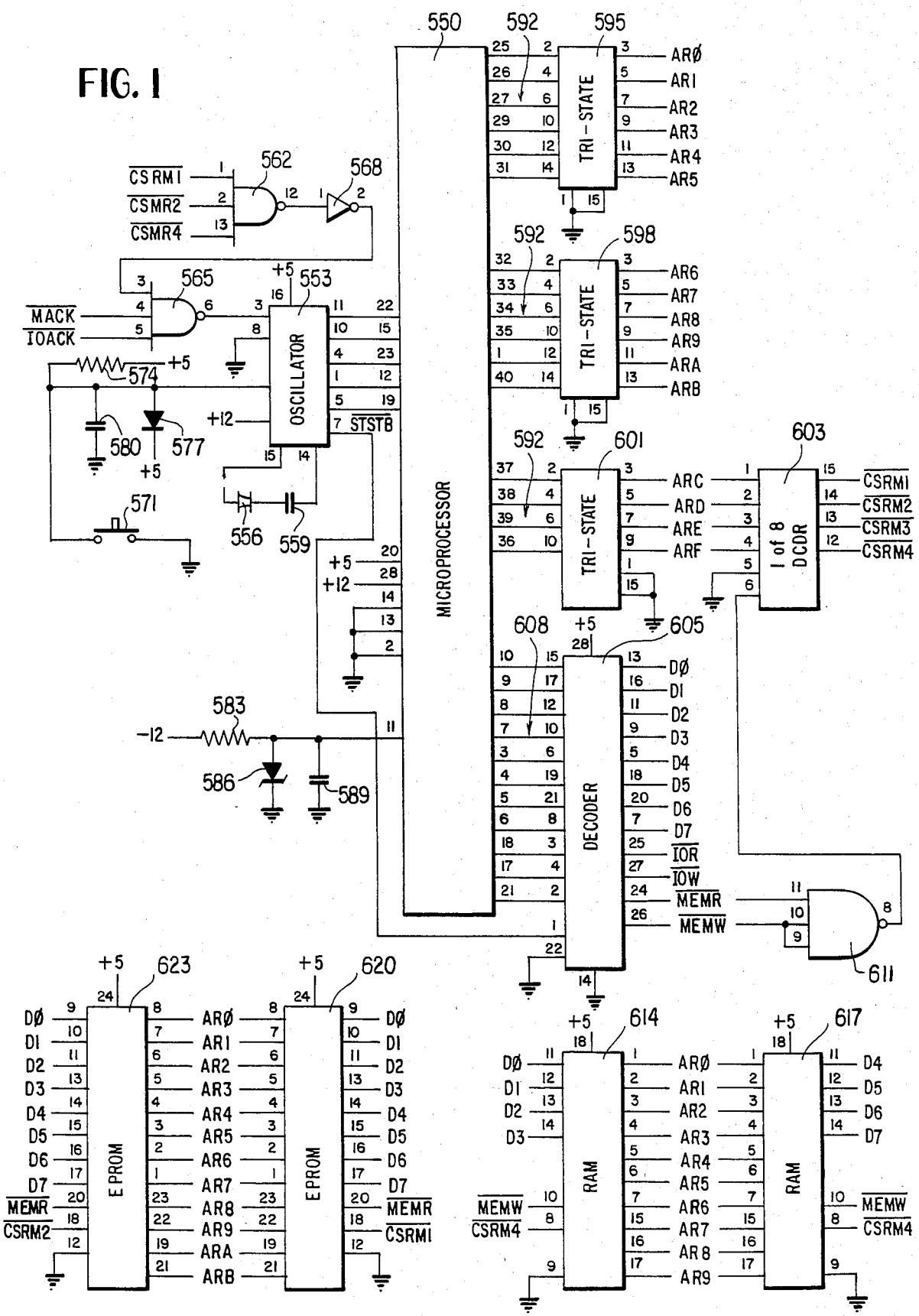
FIG. 1 illustrates microprocessor circuitry and associated memories and input-output controls.
Figure 2A:
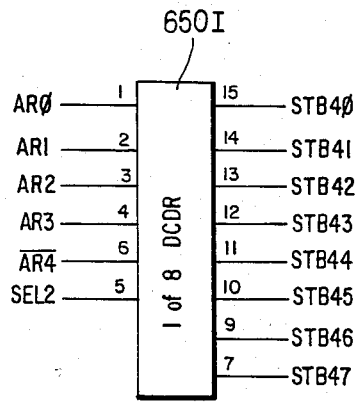
FIGS. 2A through 2F illustrate further decoders for performing strobing functions and drivers for accommodating integrated circuit fan-out.
Figure 2B:
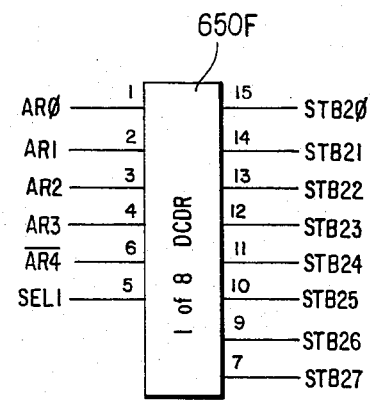
Figure 2F:
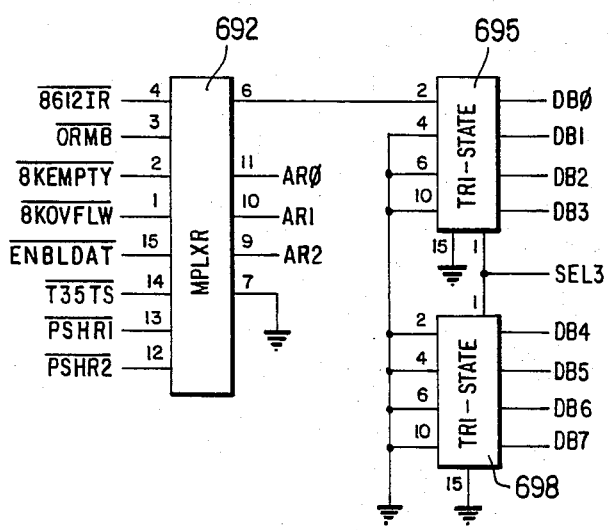
Figure 2C:
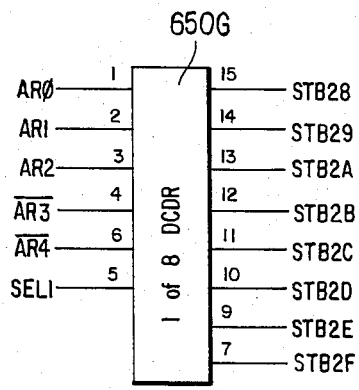
Figure 2E:
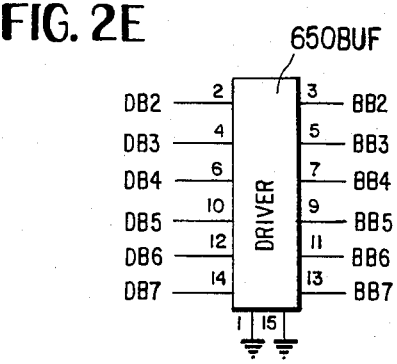
Figure 2D:
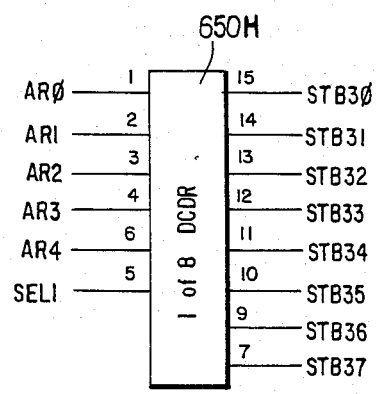

In order to facilitate an understanding of the present invention, reference is made to FIG. 27 which illustrates in a preferred embodiment certain mechanical features of a system that may be used to achieve the foregoing objects. As shown, the objects, in the form of cylindrical pellets 50, move in a substantially continuous path. The cylindrical pllets are supplied by a source not shown, and are subsequently ground to shape by grinding wheels 51 and 52. They are then deposited in mutually spaced relationship on a first transport means, such as endless belt 53 which moves the succession of spaced-apart pellets 50 to a stacking device 54. The latter may comprise a pair of endless belts positioned on opposite sides of belt 53, each having a gripping surface which is disposed in a vertical plane in the drawing. The pellets are squeezed between the pair of belts so that the gripping surfaces may transport them to a stationary support located at point 55. As the pellets arrive at the stationary support, they form stacks. As each subsequent pellet arrives the stack is urged onto a pair of rotating rollers 56 and 57. When the stack contains a predetermined number of pellets, a pusher 58 drops behind stack of pellets 59. The pusher is supported by a gantry 59A which is carried on rails 60 and 61. Motor 62 moves both gantry 59A and pusher 58 by means of a perforated steel tape 63 which engages a sprocket 64.

Rotating rollers 56 and 57 impart a rotational motion to the stack of pellets so that the pellets, which also translate in the axial direction, are caused to spiral past an inspection station 66 which views all pellets as they pass through a viewing region 66A. Thus, the entire cylindrical pellet surface is exposed to the inspection station as the pellet traverses the viewing region. Pusher 58 then pushes the stack of pellets 59 off the pair of rollers 56 and 57 and onto a second transport means, such as endless belt 67. Belt 67 travels at a higher linear velocity than pusher 58 so that a space is created between successive pellets. The belt transports the spaced pellets through a passage 68 in a turret sorter. The sorter wheel 69 of the sorter operates in response to information obtained by the present invention from the optical inspection of the pellets by the inspection station 66. Rotation of the sorter wheel 69 serves to knock the pellet present in the lowermost passage 68 into either chute 70 or 71, depending on the direction of rotation of the wheel. If the wheel does not rotate, belt 67 transports the pellets unimpeded through lowermost passage 68 to a pair of endless belts 72 and 73. The latter belts grip opposite sides of the pellets and move them to a collection station, such as a tray loader mechanism 74.

In accordance with the present invention, the pellets are inspected as they spiral past the inspection station. In a preferred embodiment, a second pusher 81 operates alternately with first pusher 58 so that, at the time when the first pusher returns to the position indicated by numeral 82 after having pushed a stack of pellets 59 along rollers 56 and 57, the second pusher is pushing the subsequent stack of pellets past inspection station 66. Thus, the pellet throughput is maintained at a relatively high level.

Inspection station 66 is illustrated in schematic form in FIG. 27. The inspection station includes optical detection apparatus such as that illustrated in greater detail in FIGS. 28 and 29. With reference to FIG. 28, a light source 300, which is preferably a multimode laser, provides a light beam 306. The light beam is reflected by reflector 308 and prism 310 and is directed to a diverging lens 312 which diverges the beam. Subsequently, beam 306 is reflected by a reflector 314 and is transmitted to a collimation lens 316 which reduces the degree of divergence. A convergance lens 318 converges the light beam in a direction different than the direction of divergence to project an elongated light beam upon a first region of illumination 370 within the aforesaid viewing region 66A. The pellets of stack 50, which are present in the first region of ilumination and supported by rollers 56 and 57, spiral past the first region of illumination. Light reflected from the surface of the pellets is collected by a lens 322 and focused onto a 1×1024 photodiode array 324. Each diode in the array corresponds to a known subregion in the first region of illumination and the light striking the photodiode contains information as to the surface characteristics of the pellet at that subregion. The photodiode signals are fed to data pre-processing circuitry (not shown) for evaluation and data compression prior to processing by subsequently connected data processing apparatus. A second light source 300A producing a light beam 306A may be provided, which is reflected and focused in a manner symmetrical to that of light beam 306.

Figure 29:
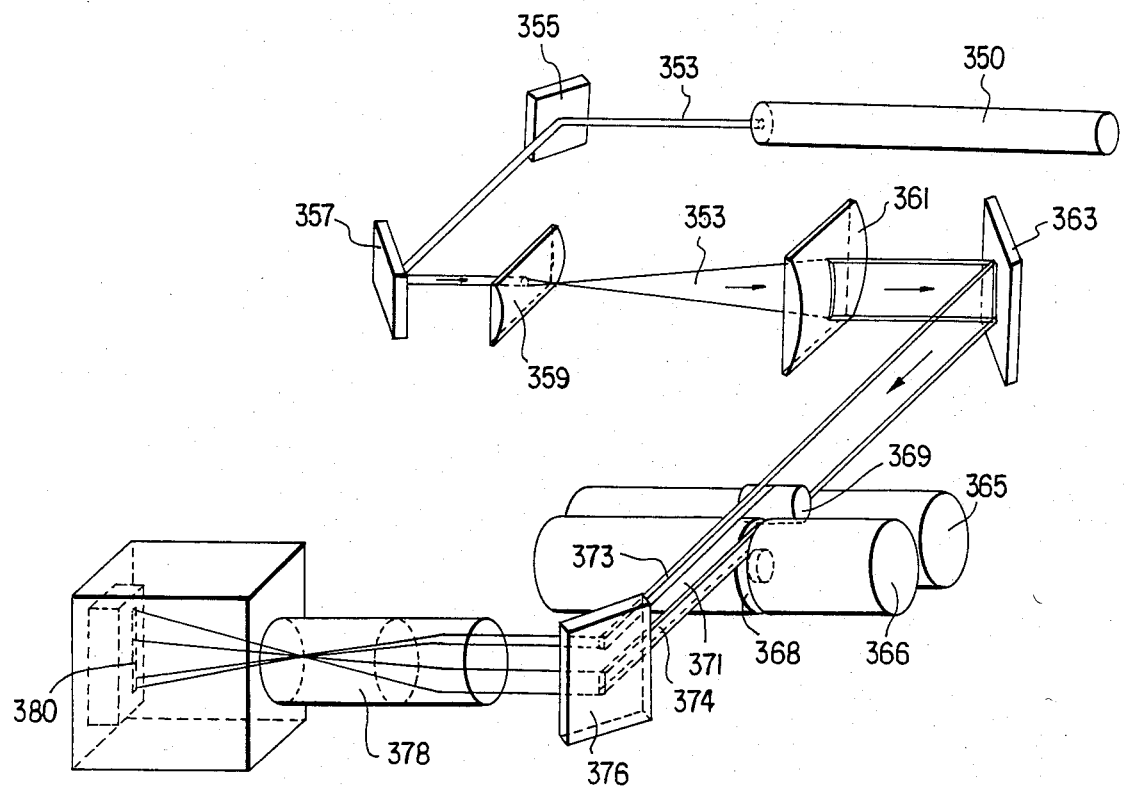
FIG. 29 illustrates in schematic form apparatus for optically generating signals indicative of pellet diameter and roundness.

Also located at the viewing region is a second illumination means, shown in FIG. 29, which comprises multi-mode laser 350 that projects a light beam 353. Beam 353 is reflected by reflectors 355 and 357 and is diverged by a diverging lens 359. A collimation lens 361 reduces the amount of divergence and directs the beam to reflector 363 and thence to rollers 56 and 57. Each of the rollers contains a slit 368. When an object such as a pellet 369 is present in this region, it will block (or eclipse) a portion of this light beam. Thus, an eclipsed portion 371 appears in this region of the light beam, as well as two portions 373 and 374 which contain light transmitted above and below the pellet respectively. A reflector 376 directs the transmitted portions to a lens 378 which collects and focuses the portions of the light beam onto a photodiode array 380. The cross sectional height of pellet 369, i.e. its diameter, is indicated by the height of the eclipsed portion 371. This information is contained in the data derived from the signals produced by individual photodiodes of photodiode array, 380, the derivation being accomplished by data pre-processing circuitry (not shown).

DETAILED DESCRIPTION OF THE INVENTION

In the drawings, the logical inverse of a signal, for example the signal CPX, is designated as $\overline{\text{CPX}}$. The lead carrying this signal is similarly designated. However, in the specification, due to typing limitations, the inverted signal and the lead carrying it are designated CPX*. This convention is adopted for all signals and leads illustrated and called out herein.

GENERATION OF TIMING PULSES

Figure 16:
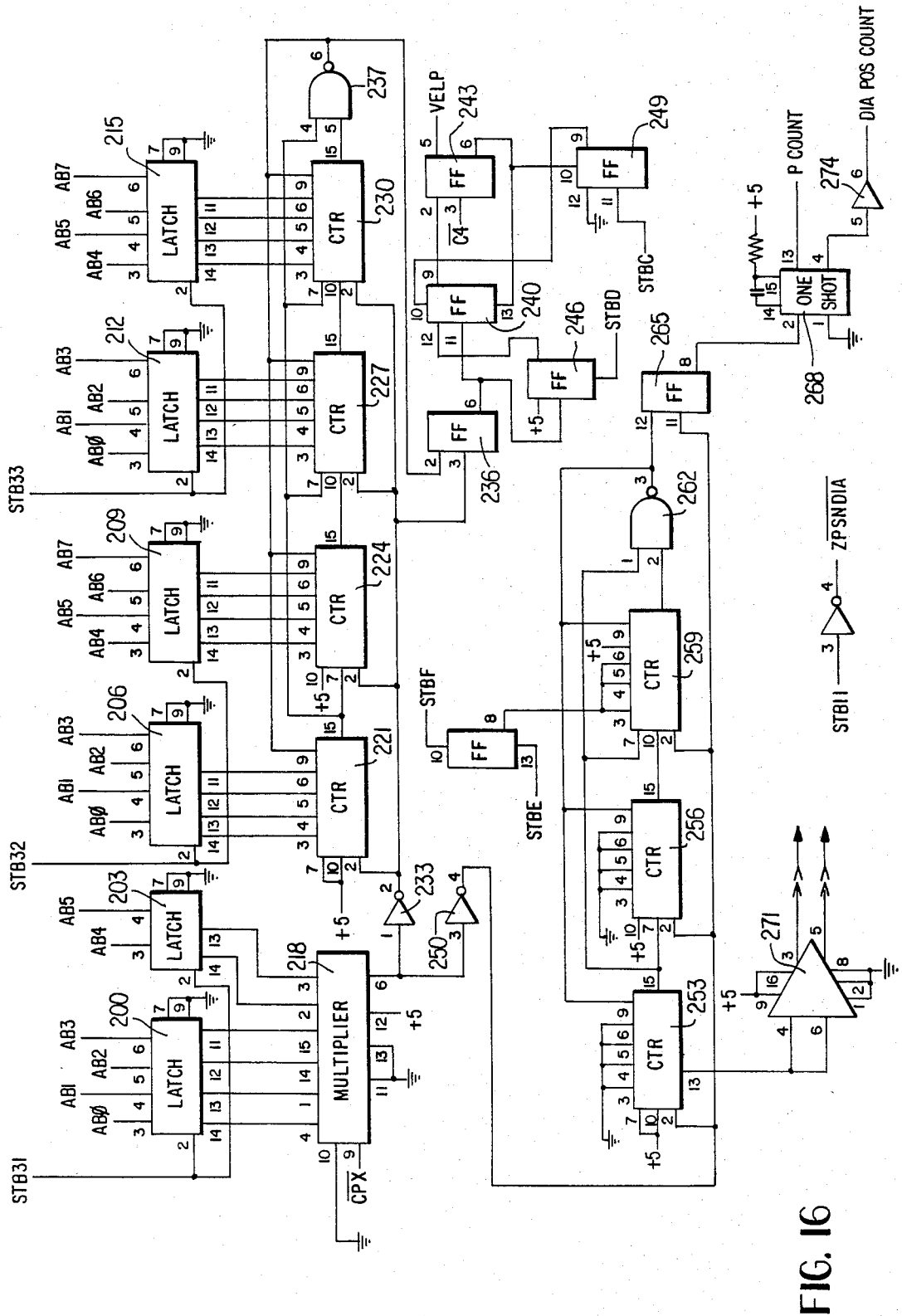
FIG. 16 illustrates circuitry for generating timing and other synchronizing pulses.

FIG. 16 illustrates circuitry which generates timing and other synchronizing pulses. The inputs of latch 203 are connected to leads AB4 and AB5. The inputs of latch 203 are connected to leads AB0–AB3, that is, to four leads of the AB bus. The inputs of latch 203 are connected to leads AB0–AB3, the inputs of latch 209 are connected to leads AB4–AB7, the inputs of latch 212 are connected to leads AB0–AB3, and the inputs of latch 215 are connected to leads AB4–AB7. A lead marked STB31 is connected to the enabling inputs of latches 200 and 203, a lead STB32 is connected to the enabling inputs of latches 206 and 209 and a lead STB33 is connected to the enabling inputs of latches 212 and 215.

The outputs of latches 200 and 203 are connected to the input of bit-rate multiplier 218. Lead CPX* is connected to the clocking input of bit-rate multiplier 218. The outputs of latches 206, 209, 212 and 215 are connected respectively to the inputs of counters 221, 224, 227 and 230.

An output of bit rate multiplier 218 is connected by way of an inverter 233 to the clocking input of each of counters 221, 224, 227 and 230. Also, the output of flip flop 236 is connected to each of the clocking inputs of these counters. An input of this flip flop is connected to the output of a NAND gate 237 as well as to the loading inputs of counters 221, 224, 27 and 230. The outputs of these counters are connected to the inputs of NAND gate 237. Flip flop 36 is connected to leads STBD and STBC by means of a flip flop network comprising flip flops 240, 243, 246 and 249. An output of flip flop 243 is connected to lead VELP.

The output of bit rate multiplier 218 is further connected, by way of inverter 250, to the clocking inputs of counters 253, 256 and 259. The output of counter 259 representing the most significant counted bit is connected by way of a NAND gate 262 to a flip flop 265. The other input of flip flop 265 is connected to the clocking inputs of counters 253, 256 and 259. The output of flip flop 265 is connected to a one-shot counter 268. The output lead 13 of counter 253 is connectd to the inputs of a differential line driver 271, the output of which is connected to and drives a stepping motor which is not shown.

The operation of the above-described circuitry is as follows:

Strobe STB31 causes the binary number, herein called "pulse frequency control number" which is present at the inputs of latches 200 and 203, to be fed to bit-rate multiplier 218. Bit-rate multiplier 218 functions to divide the pulse frequency control number by 64 and to multiply the quotient by the frequency of a pulse train present at lead CPX*. The frequency of this latter pulse train is of the order of 10 MHz and it is generated by circuitry described below. The resulting divided-and-multiplied signal is fed to counter 253 which further divides it by 16 and feeds the resulting signal to differential line driver 271. The latter applies a driving signal to the stepping motor which is of a frequency initially determined by the pulse frequency control number.

The output of bit rate multiplier 218, as inverted by inverter 250, further clocks counter 253 which divides the clocking frequency by 16; by clock counter 256 which divides the clocking frequency by 256; and by clock counter 259 which divides the clocking frequency by 8. The outputs of counters 253, 256 and 259 are fed to NAND gate 262 and thence to flip flop 265 which triggers a one-shot 268 to provide a timing pulse train of known frequency on lead marked PCOUNT. It also provides a timing pulse train via a buffer 274 to a lead marked DIA POS COUNT.

Strobe STB32 functions to feed the binary number present at leads AB∅-AB7 of the AB bus through latches 206 and 209 to counters 221 and 224, respectively. Strobe STB33 similarly functions to feed the binary numer present at leads AB∅-AB7 through latches 212 and 215 to counters 227 and 230 respectively. These counters function to divide the frequency of the pulse train produced by bit rate multiplier 218 by the numbers fed to the counters from latches 206, 209, 212 and 215. The resulting pulse train of known frequency appears at output 6 of NAND gate 237.

Strobe STBD is connected to the clocking input of flip flop 246 and functions to toggle flip flop 246 so as to delete a pulse on lead VELP. Thus, the frequency of the signal present at lead VELP is reduced.

Strobe STBC is connected to the input of flip flop 249 which toggles flip flop 243. This toggling action functions to add a pulse to the lead VELP to increase the frequency of the pulse train present at lead VELP. Signals present on leads STBC and STBD are controlled by a microprocessor described below. Accordingly, the circuitry of FIG. 16 generates timing pulse of controllable frequency at leads VELP, PCOUNT, DIA POS COUNT, and at the output of differential line driver 271.

PROCESSING OF REFERENCE PELLET DATA

Figure 25:
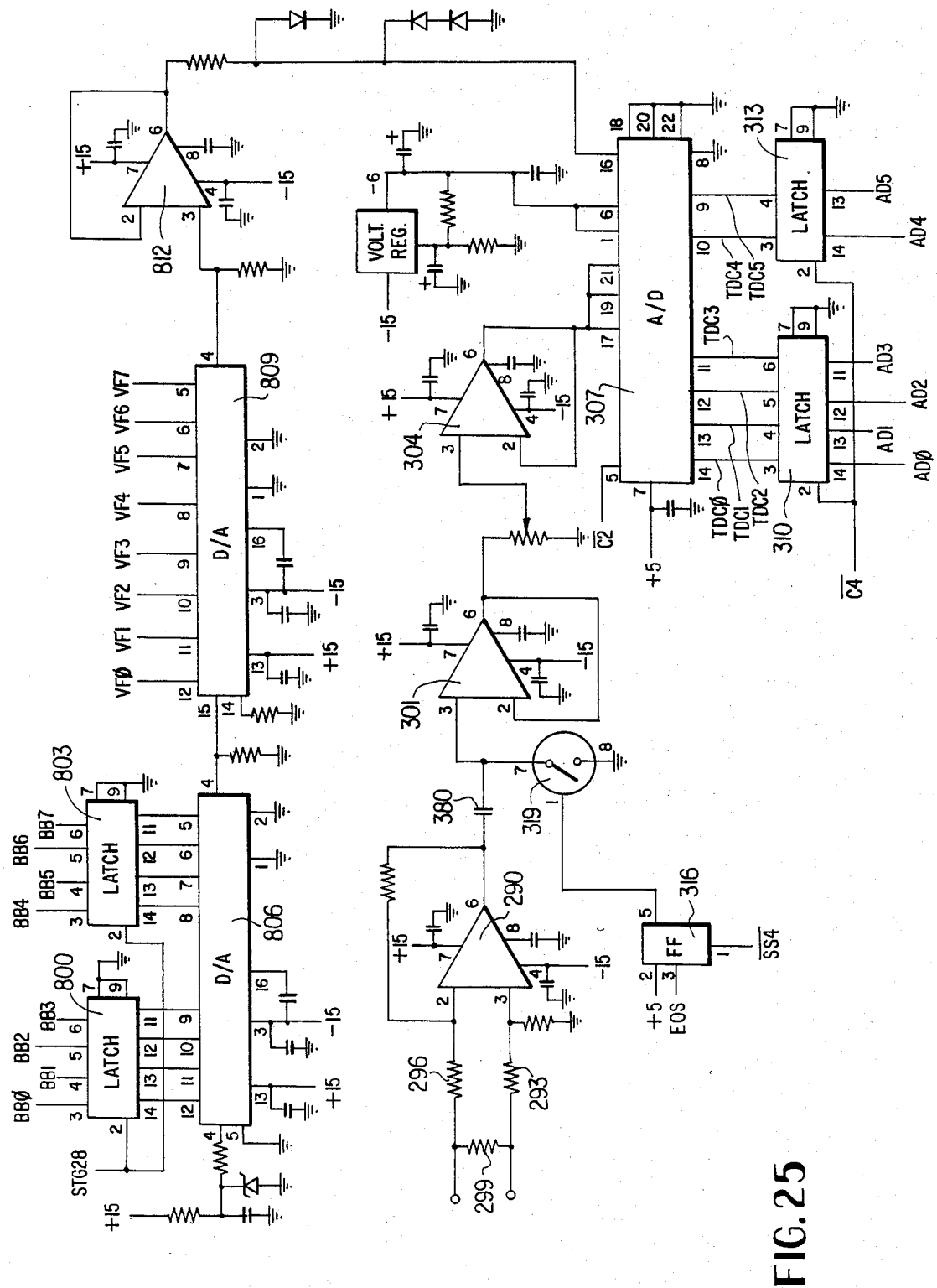
FIG. 25 illustrates circuitry for processing photodiode signals.

FIG. 25 illustrates circuitry adapted to process incoming photodiode signals. The input of buffer amplifier 290 is connected to resistor 293, 296 and 299. The output of each photodiode in the diode array is fed sequentially to resistor 299 by circuitry not shown. The output of buffer amplifier 290 is connected to the input of a second buffer amplifier 301, the output of which is connected to the input of a third buffer amplifier 304. The output of amplifier 304 is connected to an input of a flash analog-to-digital converter 307. The output of the flash analog-to-digital converter appears at leads marked TDC∅-TDC5 and is fed to latches 310 and 313. A lead EOS is connected to flip flop 316, the output of which is connected to a switch, schematically shown at 319.

Figure 20:
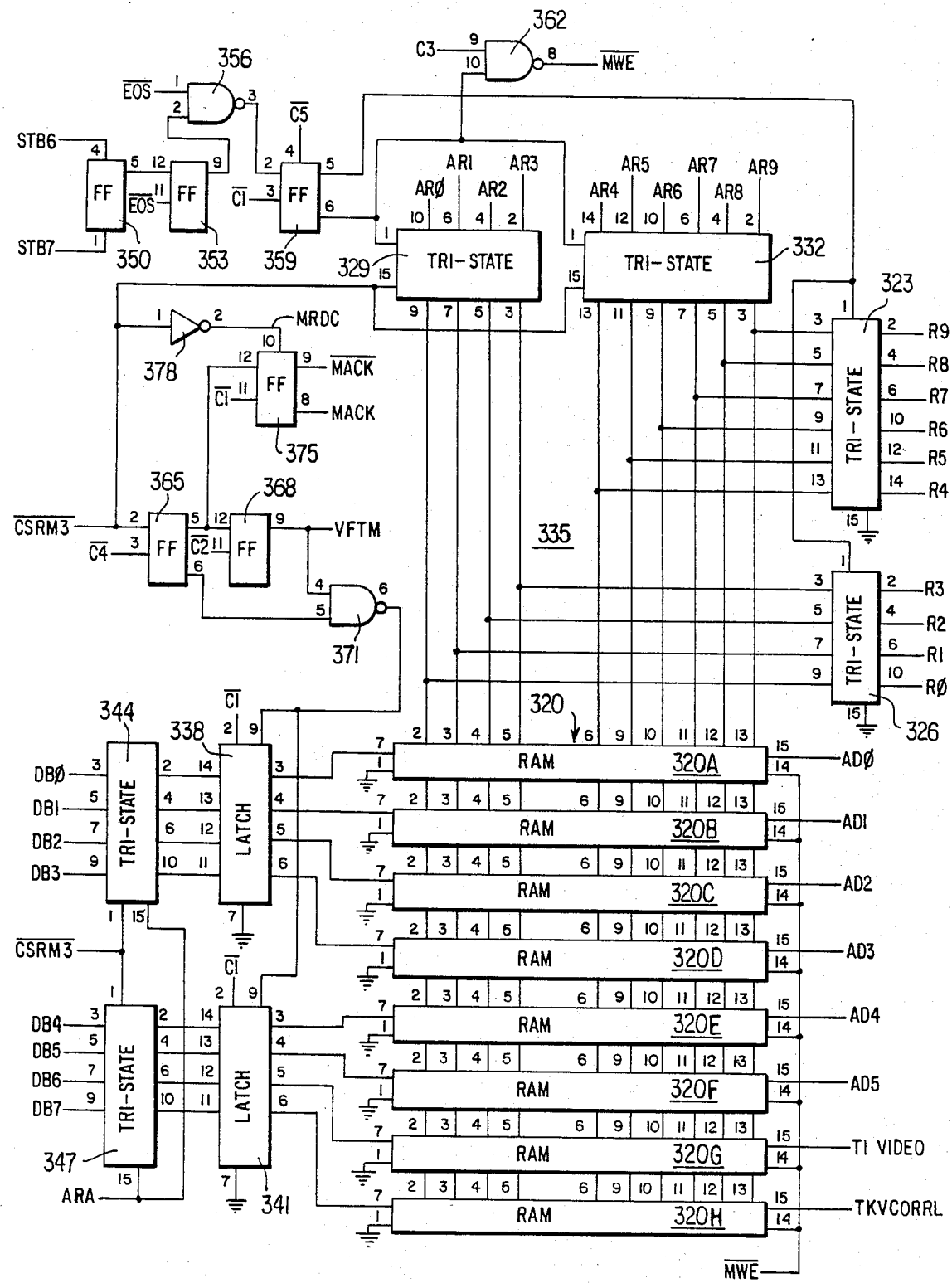
FIG. 20 illustrates a RAM and associated address selection circuitry.

The outputs of latches 310 and 313 are fed to leads marked AD∅-AD5 and lead C4* is connected to the clocking inputs of thse latches. Leads marked AD-∅-AD5 are connected to the input of random-access memory (RAM) 320 in FIG. 20. It is to be understood that RAM 320 comprises individual RAMS 320a-320h whose address inputs, namely leads 2-13, are connected in parallel so that all individual RAMS 320a-320h are addressed identically. Also in FIG. 20, leads R∅-R9 are connected to the inputs of a pair of tri-state buffers 323 and 326. Leads marked AR∅-AR9 are connected to the inputs of another pair of tri-state buffers 329 and 332. The outputs of these tri-state buffers are connected to the address selection terminals of RAM 320, which are designated generally by numeral 335. The outputs of RAM 320 are connected to the inputs of latches 338 and 341, the outputs of which are in turn connected to the input of tri-state buffers 344 and 347 respectively. The outputs of the latter buffers are connected to leads DB∅-DB7. Strobes STB6 and STB7 respectively are each connected to the resetting and clearing inputs of a flip flop 350. The output of the latter is connected to an input of flip flop 353, whose clocking input is driven by lead marked EOS*. The output of flip flop 353 is connected to the input of NAND gate 356, the other input of which is connected to lead EOS*.

The output of NAND gate 356 is connected to an input of flip flop 359, whose clocking input is connected to lead C1*. One output of flip flop 359 is connected to the enabling inputs of tri-state buffers 329 and 332, while the other output is connected to enabling inputs of tri-state buffers 323 and 326 The aforementioned output of flip flop 359 is further connected to an input of NAND gate 362. The other input of gate 362 is connected to lead C3, whose output is designated MWE*.

A lead marked CSRM3* is connected to loading input of tri-state buffers 344 and 347, as well as to an input of flip flop 365. The output of flip flop 365 is connected to an input of flip flop 368, the output of which is connected to an input of NAND gate 371, as well as to a lead VFTM. The output of NAND gate 371 is connected to the loading inputs of latches 338 and 341.

Lead CSRM3* is further connected to enabling inputs of tri-state buffers 329 and 332, as well as to an input of inverter 378. The output of inverter 378 is connected to a lead MRDC and to the resetting input of flip flop 375. An output of flip flop 365 is connected to an input of flip flop 375, whose clocking input is connected to lead C1*. The two outputs of flip flop 375 are connected to leads marked MACK and MACK*.

Accordingly, as the diode array is scanned, the analog voltage of each diode, which is fed to resistor 299 in FIG. 25, is amplified and buffered by three buffer amplifiers 290, 301 and 304. The succession of diode voltage signals produced is termed a video signal. The analog voltage is changed from analog form to digital form by flash converter 307. It is held by latches 310 and 313 and written as a 6-bit number onto leads AD0–AD5 and into RAM 320 at an address selected by the pair of tri-state buffers 323 and 326. The address is fed to these tri-state buffers by leads R0–R9. The address on leads R0–R9 is selected by virtue of strobe STB6 which toggles flip flops 350, 353 and 359. This action loads RAM 320 with data present at leads AD0–AD5, at addresses given by R0–R9 rather than at addresses given by AR0–AR9. At selected intervals, lead EOS in FIG. 25 toggles flip flop 316 to activate switch 319 to discharge capacitor 380.

After RAM 320 is loaded with the digital signal data, strobe STB7 toggles flip flops 350, 353 and 359 to enable tri-state buffers 329 and 332 and disable tri-state buffers 323 and 326. Further, it allows data stored in RAM 320 at addresses given by leads AR0–AR9, to be read out into latches 338 and 341 and thence to tri-state buffers 344 and 347 which supply the digital data to leads DB0–DB7. The data on leads marked T1VIDEO and TKVCORRL, which are stored in RAM 320 and which are read out at DB6 and DB7 respectively, are discussed hereinbelow.

Figure 22:
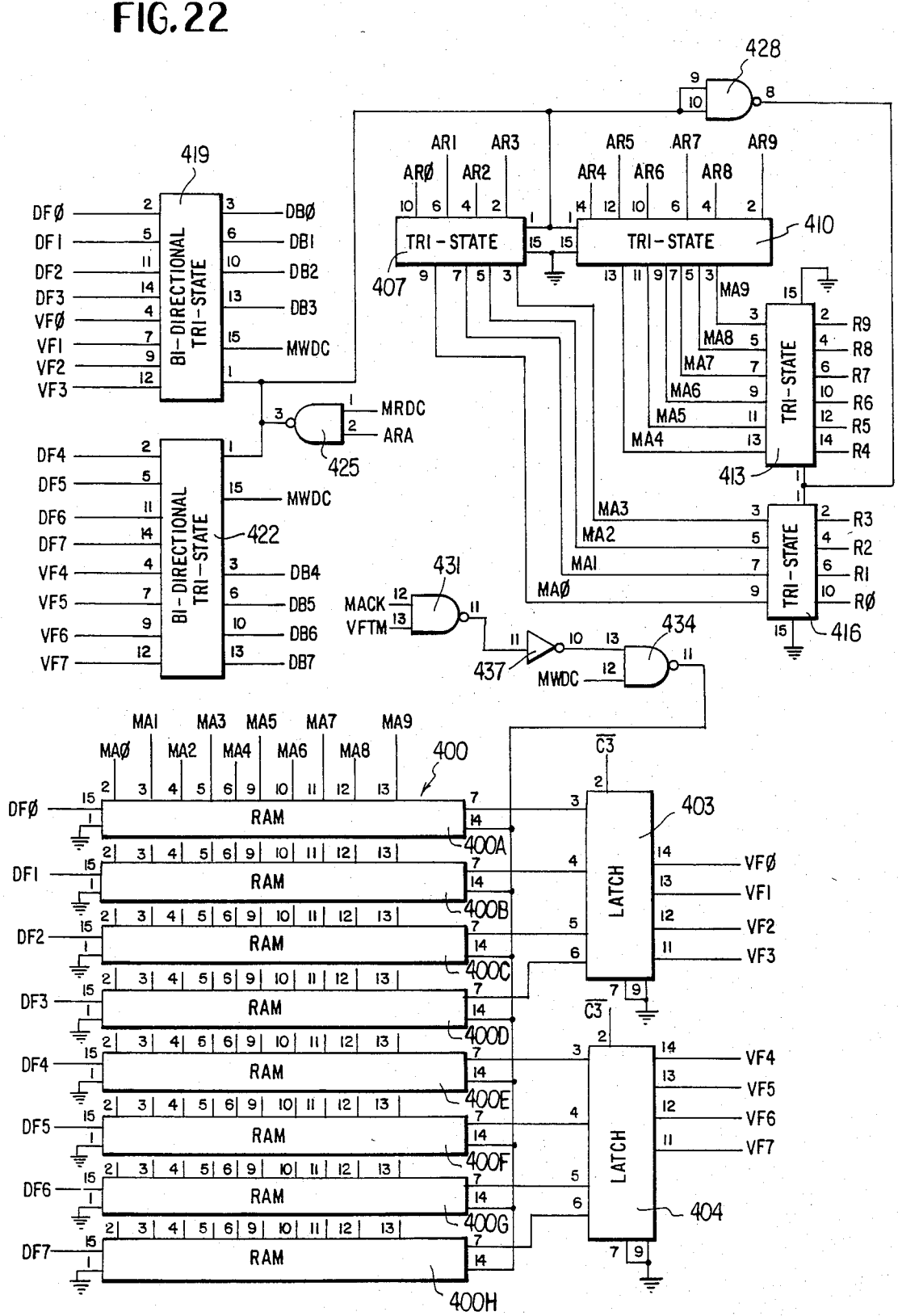
FIG. 22 illustrates a RAM for storing diode weighting factors.

FIG. 22 illustrates a random access memory (RAM) 400 which is used to store diode weighting factors. RAM 400 comprises several separate RAM's 400a–400h, the address leads of which are connected in parallel. Outputs 7 of RAM 400 are connected to inputs of latches 403 and 404. The outputs of latches 403 and 404 are connected to leads VF0–VF7. Lead C3 is connected to the clocking input of latches 403 and 404. The inputs of RAM 400 are connected to leads marked DF0–DF7. Address selection inputs of RAM 400 are connected to leads marked MA0–MA9. Leads MA0–MA9 comprise the outputs of tri-state buffer pair 407 and 410 and the pair 413 and 416. The inputs of tristate buffer pair 407 and 410 are connected to leads marked AR0–AR9. The inputs to tri-state buffer pair 413 and 416 are connected to leads marked R0–R9.

Leads marked DF0–DF7 (the DF bus) VF0–VF7 (the VF bus), and DB0–DB7 (the DB bus), are connected to bidirectional tri-state buffers 419 and 422. These bidirectional tri-state buffers function to select a signal path such that either the signal travels from the VF bus to the DB bus, or alternately, from the DB bus to the DF bus. Lead MRDC is connected to an input of a NAND gate 425, whose output is both connected to bidirectional tri-state buffers 419 and 422, and to both inputs of NAND gate 428. The output of NAND gate 428 is connected to tri-state buffer pair 413 and 416, while the input of this gate is connectd to tri-state buffer pair 407 and 410.

Leads MACK and VFTM are each connected to an input of a NAND gate 431, the output of which is coupled to an input of NAND gate 434 through an inverter 437. The other input of NAND gate 434 is connected to lead MWDC. The output of NAND gate 434 is connected to RAM 400. This circuitry must be viewed in connection with that of FIG. 9.

Figure 9:
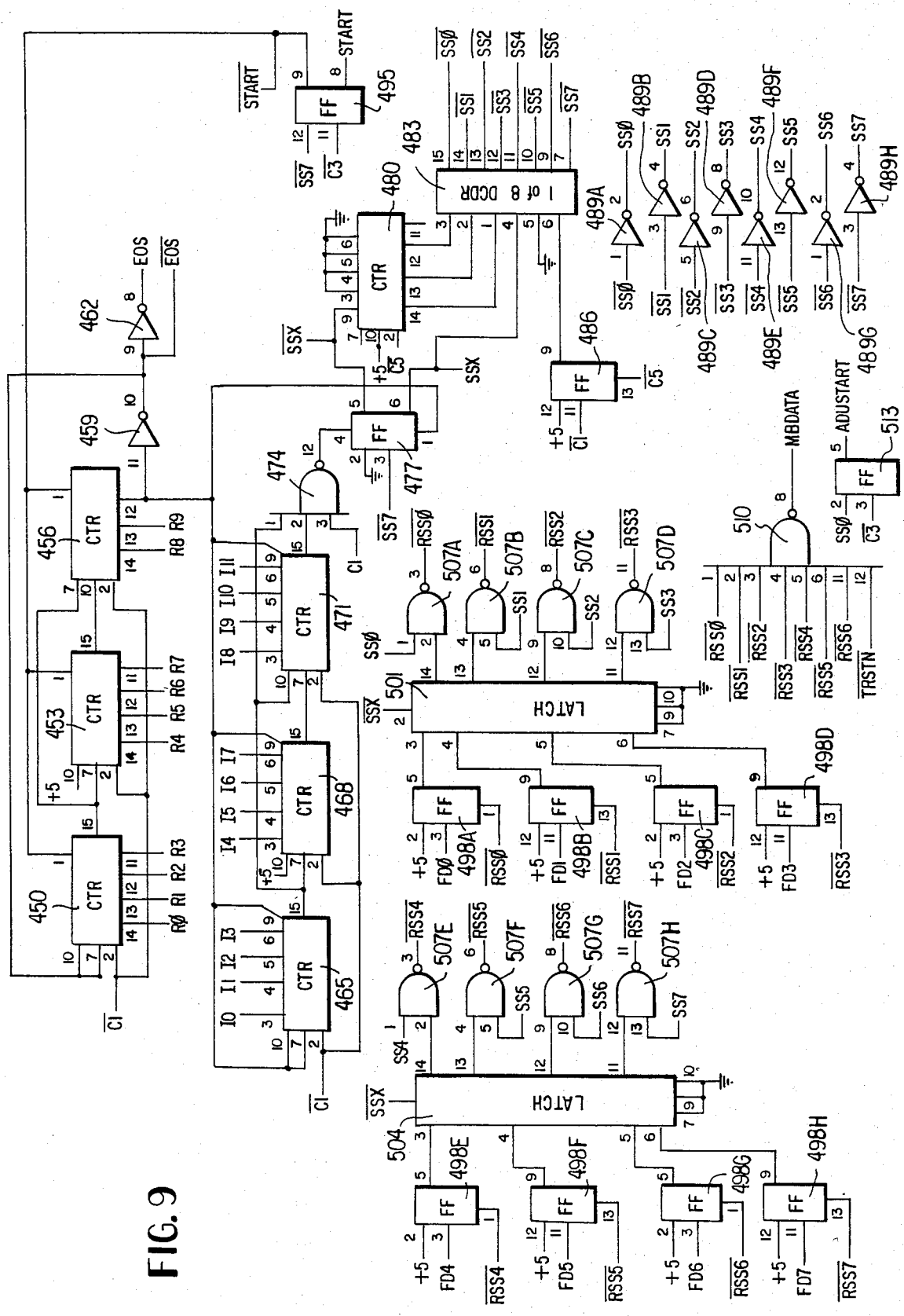
FIG. 9 illustrates the fundamental diode address generator, as well as data formatting circuitry.

FIG. 9 depicts the fundamental diode address generator, as well as data formatting circuitry. The outputs of counters 450, 453 and 456 are connected to leads R0–R9 and lead C1* is connected to the clocking input of these counters. The most significant bit of counters 450, 453 and 456 is connected to the input of inverter 459, the output of which is fed back to enabling inputs of counter 450. The output of inverter 459 is further connected to lead EOS* and to the input of inverter 462, the output of which is connected to lead EOS. The most significant bit of counters 450, 453 and 456 is also connected to the enabling inputs of counters 465, 468 and 471. The outputs of these latter counters, together with lead C1, are connected to the inputs of a NAND gate 474.

The output of gate 474 is connected to resetting input of a flip flop 477, an output of which is connected to counter 480. The outputs of counter 480, as well as an output of flip flop 477, is connected to inputs of a one-to-eight decoder 483. The outputs of this decoder are connected to leads SS0–SS7*.

The clocking and setting inputs of a flip flop 486 are connected to leads C1* and C5* respectively and the output of this flip flop is connected to an enabling input of the 1-of-8 decoder 483. Leads SS0*–SS7* are each connected to inputs of respective inverters 489a–489h, the outputs of which, labeled SS0–SS7, produce the inverse of the input signal. Lead SS7* is connected to an input of a flip flop 495, and lead C3* is connected to the clocking input of this flip flop. One output of flip flop 495 is connected to clearing inputs of counters 450, 453 and 456 as well as to a lead marked START*. The other output of flip flop 495 is connected to a lead marked START.

Leads FD0–FD7 are each connected to a clocking input of each of flip flops 498a–498h. Leads RSS0*–RSS7* are similarly each connected to each of a clearing input of these flip flops. The outputs of each of flip flops 498a–498d are connected to inputs of latch 501 and the outputs of each of flip flops 498e–498h are connected to inputs of latch 504. A lead SSX* is connected to a gating input of each of these latches. The outputs of these latches are connected to respective inputs of NAND gates 507a–507h. The other input of each of NAND gates 507a–507h is connected respectively to leads SS0–SS7. The output of each of NAND gates 507a–507h is respectively connected to leads RSS0*–RSS7*. Each of leads RSS0*–RSS6*, together with lead TRSTN*, is connected to inputs of NAND gate 510. The output of NAND gate 510 is connected to lead MBDATA. One input of a flip flop 513 is connected to lead SS0 and the clocking input is connected to lead C3*. The output of this flip flop is connectd to lead ADVSTART.

FIG. 1 illustrates a microprocessor 550 and associated memories and input-output controls. The outputs of oscillator 553 are connected to selected inputs of microprocessor 550 and the oscillator frequency is controlled by a crystal 556 and a capacitor 559 connected in series. Leads CSRM1*, CSRM2* and CSRM4*, are connected to the inputs of a NAND gate 562, the output of which is coupled to an input of a NAND gate 565 by means of inverter 568. Leads MACK* and IOACK* are each connected to other inputs of NAND gate 565, the output of which is connected to an oscillator 553. A resetting input lead 2 of oscillator 553 is selectively connectable to ground by means of a reset switch 571. Resetting input 2 is further connected to a 5 volt positive voltage source, indicated "+5", through both resistor 574 and through diode 577. It is further connected to ground through capacitor 580.

Microprocessor 550 is also connected to the 5 volt positive supply and to a 12 volt positive power supply indicated "+12" by means of leads 20 and 28 respectively. It is further connected to ground through leads 14, 13 and 2. Lead 11 of microprocessor 550 is connected to a negative 12 volt power supply indicated "−12" by a resistor 583, as well as to ground through both a Zener diode 586 and a capacitor 589.

RAM address leads AR0–ARF are connected to microprocessor terminals generally designated 592 through tri-state buffers 595, 598 and 601. Leads AR-C–ARF are further connected to a one-of-eight decoder 603, other leads of which are connected to leads CSRM1*, CSRM2*, CSRM3* and CSRM4*. The data bus comprising leads D0–D7 and a control bus comprising leads IOR*, IOW*, MEMR* and MEMW*, are connected to decoder 605, which is connected to terminals generally designated 608 of microprocesor 550. Terminals MEMR* and MEMW* are connected to inputs of NAND gate 611, the output of which is connected to one-of-eight decoder 603. Decoder 608 is further coupled to oscillator 553 by lead STSTB*. RAMs 614 and 617 are each connected to leads AR-0–AR9 and to leads MEMW* and CSRM4*. RAM 614 is connected to leads D0–D3 and RAM 617 is connected to leads D4–D7. A pair of erasable programmable memories (EPROMs) 620 and 623 are each connected to leads AR0–AR9, ARA, ARB, D0–D7, MEMR*, CSRM1* and CSRM2*.

FIGS. 1A through 1F and FIGS. 2A through 2F depict decoders which perform strobing functions and drivers that function to accommodate integrated circuit fan-out. One-of-eight decoders 650a–650i are effective to decode signals present on leads AR0–AR7, AR3*, AR4*, SEL0, SEL1, and SEL2 to information transmitted on strobe leads STB0–STB47 (hexadecimal notation). Leads IOR* and IOW* are each connected to inputs of a NAND gate 653, the output of which is connected to one-of-eight decoder 650a, as well as to an input of an inverter 656. The output of the latter is connected to lead IOACK*. Lead AR3 is connected to lead AR3* through an inverter 659. Lead AR4 is connected to lead AR4* through an inverter 662. Lead MEMW* is connected to lead MWDC through an inverter 665. Lead CSRM3* is connectd to an input of an inverter 668, the output of which is connected to an input of NAND gate 671. Lead MEMR* is connected to an input of an inverter 674, the output of which is connected to an input of NAND gate 671. The output of AND gate 671, together with leads SEL2 and SEL3, are connected to an input of a NAND gate 677.

The output of NAND gate 677 is connected to direction control buffers 680 and 683. One set of terminals of buffers 680 and 683 is connected to leads D0–D7 and another set of terminals is connected to leads DB0–DB7. Leads DB0–DB7 are connected to terminals of bidirectional bus drivers 686 and 689, while leads AB0–AB7 and leads BB0 and BB1 are connected to another set of terminals of these bidirectional bus drivers.

A set of leads AR0–AR2, PSHR2*, PSHR1*, T3STS*, ENBLDAT*, 8KOVFLW*, 8KEMPTY*, ORMB* and 8612IR* are connected to respective inputs of multiplexer 692. The output of unit 692 is connected to an input of a tri-state driver 695. The other inputs of driver 695, as well as all of the inputs of a tri-state driver 698, are connected to ground. Lead SEL3 is connected to an enabling input of these tri-state drivers, the outputs of which are connected to leads DB0–DB7. A tri-state buffer 650 but is interposed between the DB and BB buses.

Each diode in the photodiode array may possess a different response characteristic and, further, the light reflected to each may vary in intensity from light reflected to others but due to factors unrelated to pellet surface features. Thus, it is desired to normalize all diode response characteristics and this is done by the generation of diode weighting factors.

The operation of the above-described circuitry shown in FIG. 1, 1A, 2, 9, 20, 22 and 25 in reading reference pellet data and generating diode weighting factors is as follows:

Each photodiode of the 1×1024 diode array (not shown) is addressed sequentially by counters 450, 453 and 456 of FIG. 9. These counter generate and feed the addresses to the R bus at a rate determined by the C1* clock. The couhters count from 1 to 1024 and then stop, to be restarted by flip flop 495. Each number counted selects a diode whose voltage is to be read. This voltage is coupled to resistor 299 and then to buffer amplifiers 290, 301 and 304 in FIG. 25. An amplified voltage is coupled to flash A/D converter 307, thence to the TDC bus which inputs to latches 310 and 313. The output of the latter feeds the AD bus which in turn feeds the input of RAM 320 in FIG. 20. Each diode voltage contained on the AD bus and inputted to RAM 320 is stored at an address determined by the R bus. The address is fed through tri-state buffers 323 and 326 to the address selection terminals of RAM 320. The diode voltage signals are stored in RAM 320 because they are generated by flash A/D converter 307 at a rate faster than microprocessor 550 can process them.

At a selected time later, microprocessor 550 issues a signal through tri-state buffers 595, 598 and 601 to the AR bus, which is fed to the address selection terminals of RAM 320 through tri-state buffers 329 and 332. The corresponding diode signal voltage magnitude is read out of RAM 320 on the DB bus and is transmitted to microprocessor 550 for processing through tri-state buffers 686 and 689 in FIG. 1A, to the DB bus, and thence to the D bus through decoders 680 and 683. The microprocessor processes these diode signals to compute diode weighting factors as explained below.

Microprocessor 550 is programmed by instructions contained in EPROMs 620 and 623 and RAMs 614 and 617 in FIG. 1. A portion of the instructions require it to compute a weighting factor for each diode by comparing each diode signal with a predetermined norm and to generate in response a weighting factor indicative of the difference so that the diode will produce a signal of known magnitude in response to light of a fixed intensity. After computation, these weighting factors are transmitted from microprocessor 550 through decoder 605 to the D bus, through direction control buffers 680 and 683, and along the DB bus to the bidirectional tri-states 419 and 422 in FIG. 22. These bidirectional tri-states channel the DB bus information to the DF bus which is connected to the data inputs of RAM 400. The data inputs receive the weighting factors and each factor is stored at an address designated by the signals transmitted to RAM 400 on the MA bus. These signals originate at microprocessor 550 and are transmitted from it to the AR bus in FIG. 1, through tri-state buffers 407 and 410 in FIG. 22, and to the MA bus which is connected to the address selection terminals of RAM 400. Thus, a weighting factor for each photodiode is stored in RAM 400. These factors are used by circuitry described below, which process the signals produced by the diodes. The signal processing results in a situation wherein individual diode anomalies are substantially eliminated so that the signals produced by all diodes in response to light of a given intensity will be identical.

PROCESSING OF DATA FROM PELLETS UNDER EXAMINATION

Figure 4:
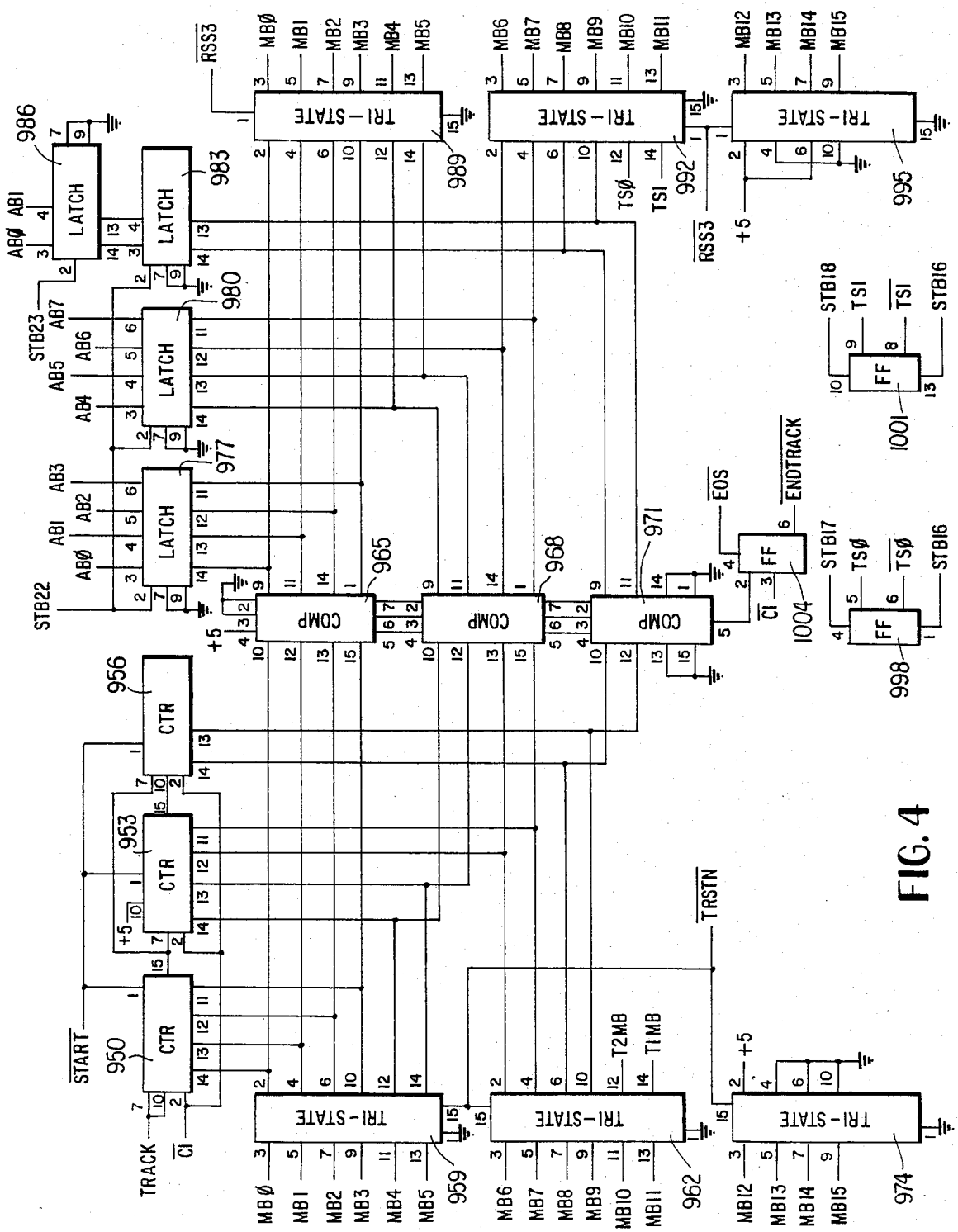
FIG. 4 illustrates circuitry for providing an address, measured from the beginning address of the track gate, of each diode whose signal is being processed.
Figure 4A:
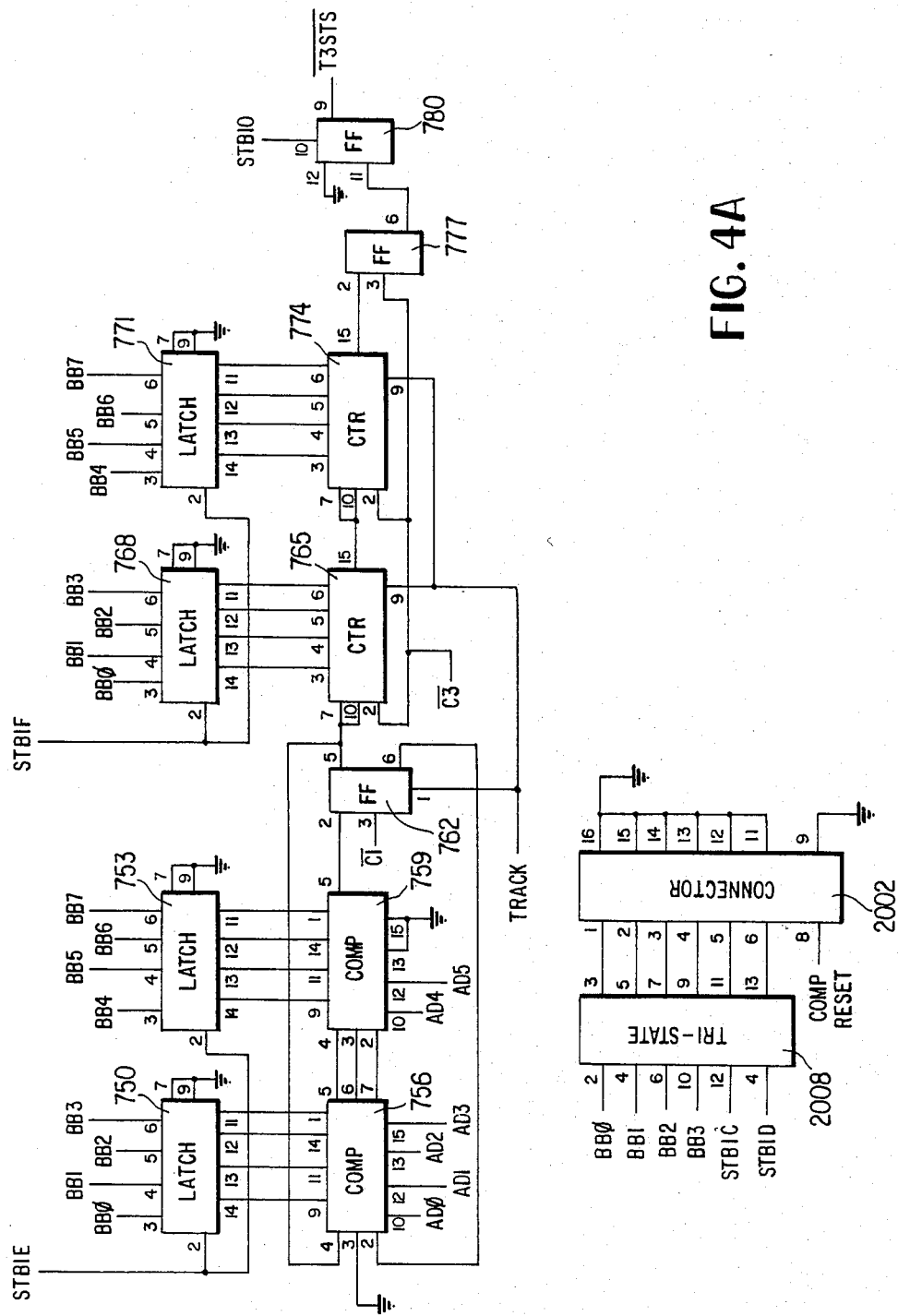
FIG. 4A illustrates automatic gain control circuitry for normalizing acquired pellet data.

FIG. 4A depicts automatic gain control circuitry used to normalize acquired pellet data. Leads BBØ BB7 are connected to inputs of latches 750 and 753, the outputs of which are fed to comparators 756 and 759. Strobe STB1E is connected to the clocking inputs of latches 750 and 753. Leads ADØ-AD5 are connected to the other inputs of comparators 756 and 759. The output of comparator 759 is connected to an input of a flip flop 762, while the clocking input of flip flop 762 is connected to lead C1*. One output of flip flop 762 is connected to counter 765, as well as to a clocking input of comparator 756. The other output of flip flop 762 is connected to a latching input of comparator 756. Leads BBØ-BB7 are connected to inputs of latches 768 and 771, the outputs of which are connected to counters 765 and 774. Strobe STB1F is connected to the clocking inputs of latches 768 and 771. A lead designated TRACK is connected to the setting inputs of flip flop 762 and to setting inputs of counter 765 and of counter 774. Lead C3* is connected to clocking inputs of counters 765 and 774 and flip flop 777. The most significant bit of counters 765 and 774 is connected to an input of flip flop 777. The output of flip flop 777 is connected to a clocking input of flip flop 780, the output of which is connected to lead T3STS*.

The operation of the circuitry illustrated in FIG. 4A is as follows:

Leads BBØ-BB7 feed a signal to latches 750 and 753 which is indicative of a reference amplitude, that is, of the magnitude of an average of the signals produced by the photosensitive diodes in response to the reference pellet. The signal on the BB bus originates at microprocessor 550, is fed to input-output decoder 605 in FIG. 1, travels along the D bus through directional control buffers 680 and 683 in FIG. 1A, from these latter buffers to the DB bus and to tri-state buffer 650buf in FIG. 2E. Tri-state buffer 650buf feeds the signal from the DB bus to the BB bus which is connected to the inputs of latches 750 and 753 in FIG. 4A. Strobe STB1E feeds this magnitude information to one set of inputs of comparators 756 and 759, which compare it to amplitude information fed to the other inputs, namely leads ADØ-AD5. This latter information indicates the magnitude of a signal produced by each diode during a scan of a pellet under examination and weighted by the weighting factors stored in RAM 400.

The output of comparator 759 indicates whether the weighted magnitude signal contained on leads ADØ-AD5 is greater than the reference magnitude contained on leads BBØ-BB7. If so, flip flop 762 is toggled, thereby advancing counters 765 and 774. These counters count upward from a number strobed into them by strobe STB1F through latches 768 and 771 and originating on the BB bus from microprocessor 550. When the output of counters 765 and 774 reaches the count of 255, flip flops 777 and 780 are toggled and signal T3STS* is fed back to microprocessor 550.

Since the output of counters 765 and 774 is the sum of the number latched into latches 768 and 771 and the number of times the diode signal magnitude has exceeded the referecce magnitude, a knowledge by the microprocessor of the latched number and the receipt of the signal on lead T3STS* allows it to calculate the number of signal excesses. If the number of excesses is not tolerable, for example due to the fact that the reflectivity of the pellet currently examined is greatly different from that of the reference pellet, microprocessor 550 adjusts the amplification, or gain, of the diode signals. In a preferred embodiment of the invention, the microprocessor is programmed to perform the gain adjustment approximately five times during the scanning of each pellet. The manner in which the gain adjustment, herein termed automatic gain control, is executed will become clear from the explanation below with reference to FIG. 25. FIG. 25, discussed hereinabove, further depicts automatic gain control circuitry. Leads BBØ-BB7 are connected to inputs of latches 800 and 803, the outputs of which are connected to digital-to-analog [D/A] converter 806. Lead STB28 is connected to the latching inputs of latches 800 and 803. The output of D/A converter 806 is connected to an input of D/A converter 809, whose other inputs are connected to leads VFØ-VF7. The output of D/A converter 809 is connected to the input of operational amplifier 812, which is operated in a current-to-voltage transform mode. The operation of this circuitry is as follows.

Leads BBØ-BB7 transmit a signal from microprocessor 550 to latches 800 and 803. This signal is based on the signal T3STS* produced by circuitry on FIG. 4A. This signal contains information pertaining to the degree of gain change needed in order to normalize the photodiode output with respect to the output produced in response to the reference pellet. This signal is strobed into D/A converter 806 by STB28. The output of converter 806 is an analog current which is proportional to the magnitude of the signal on the BB bus. This output current is fed to an input of D/A converter. Leads VFØ-VF7 are connected to the outputs of RAM 400 in FIG. 22 which stores diode weighting factors. Thus, D/A converter 809 receives as one input a microprocessor signal indicating the amount of diode gain control needed. It further receives a weighting factor on the VF bus for each diode in synchronism with diode scanning.

The output of D/A converter 809 is a current which corresponds both to the weighting factor and to the gain control signal. This current is changed to a voltage by operational amplifier 812, which produces an output voltage signal that is fed to an input of flash A/D converter 307. Flash converter 307 also receives as an input a signal for each diode originating at resistor 299 and processed by buffer amplifiers 290, 301 and 304. Converter 307 responds with a signal on leads TDCØ-TDC5, which is indicative of the diode signal magnitude but modified by the automatic gain control signal and the diode weighting factor. This signal is present on the TDC bus and is latched by latches 310 and 313 which feed the signal to leads ADØ-AD5. Thus, a signal, termed a modified video signal, is produced on the AD bus which is indicative of the reflectivity of the inspected pellet surface, yet normalized to adjust for variations in photodiode response characteristics and for variations in the general reflectivity of the pellet surface.

TRACK GATE GENERATION AND TRANSLOCATION

Figure 3:
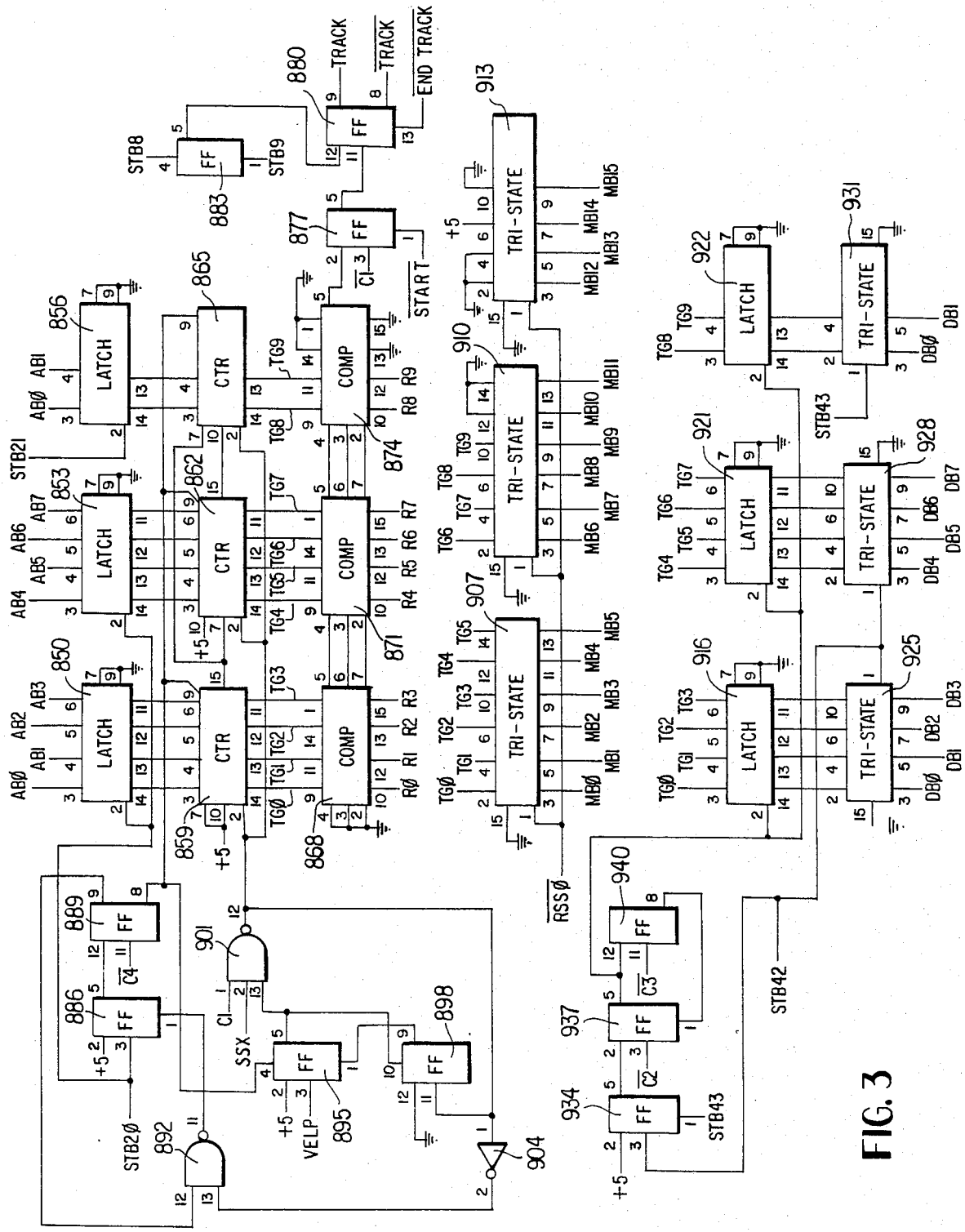
FIG. 3 illustrates circuitry for generating a track gate and locating its position.

FIG. 3 illustrates circuitry which generates a track gate and locates its position. Leads AB0-AB7 are connected to inputs of latches 850 and 853 and lead STB20 is connected to the latching inputs of these latches. Leads AB0 and AB1 are connected to the inputs of a latch 856 whose latching input is connected to lead STB21. The outputs of these latches are connected to the inputs of counters 859, 862 and 865. The outputs of these counters are connected to leads TG0-TG9 which are in turn connected to inputs of comparators 868, 871 and 874. The other inputs of these comparators are connected to leads R0-R9 which are coupled to the outputs of the fundamental diode address generator comprising counters 450, 453 and 456 and depicted in FIG. 9. The output of comparator 874 is connected to an input of a flip flop 877, whose output is coupled to the clocking input of a flip flop 880. The other input of unit 880 is connected to an output of a flip flop 883. A lead designated START* is connected to a setting input of flip flop 877, while a lead ENDTRACK* is connected to a setting input of flip flop 880. The outputs of flip flop 880 are connected to leads TRACK and TRACK*. Flip flop 883 is inputted by leads STB8, connected to the resetting input, and STB9, connected to the setting input. Lead STB20 is coupled through flip flop 886 to an input of a flip flop 889 which has lead C4* connected to its clocking input. One output of flip flop 889 is connected to an input of a NAND gate 892. The other output of flip flop 889 is connected both to the loading inputs of counters 859, 862 and 865 as well as to the resetting input of a flip flop 895.

Lead VELP, generated by flip flop 243 in FIG. 16 is connected to the clocking input of flip flop 895. The output of the latter is connected to both the resetting input of a flip flop 898 and to an input of a NAND gate 901. Both leads CI and SSX are connected to inputs of NAND gate 901. The output of NAND gate 901 is connected to a clocking input of counters 859, 862 and 865 as well as to an input of NAND gate 892 through inverter 904. Tri-state buffers 907, 910 and 913 are interposed between leads TG0-TG9 and MB0-MB15. Lead RSS0* is connected to a controlling input of these tri-state buffers.

The inputs of latches 916, 919 and 922 are connected to leads TG0-TG9 and the outputs of these latches are connected to tri-state buffers 925, 928 and 931. Lead STB43 is connected to latching inputs of latches 916, 921 and 922 by means of flip flops 934, 937 and 940. Lead STB42 is connected to controlling inputs of tri-state buffers 925 and 928. Lead STB43 is connected to a controlling input of tri-state buffer 931.

The operation of the circuitry shown in FIG. 3 is as follows:

A signal present on leads AB0-AB7 is strobed into counters 859 and 862 by strobe STB20. The signal present on leads AB and AB1 is separately strobed into counter 865 by strobe STB21. The information transmitted to counters 859, 862 and 865 by these two strobings provides a number at which the counters begin to increment. Incrementing is determined by leads VELP, SSX and C1. Thus, these counters produce a signal present on leads TG0-TG9 which is determined either by the number fed to these counters by latches 850, 853 and 856, or this latter number as incremented by counters 859, 862, and 865 by signals present on leads VELP, SSX, or C1. In either case, comparators 868, 871 and 874 compare the number present on the TG bus with the signal present on leads R0-R9. The signal present on this R bus indicates the address of the present diode whose signal is being processed. If the diode address is a lower number than that present on the TG bus, flip flops 877 and 880 remain untoggled and the signals present at leads START*, TRACK and TRACK* indicate that the track gate is not yet operative. As soon as the diode address present on the R bus exceeds the number present on the TG bus, the output of comparator 874 toggles flip flop 877 and the leads START*, TRACK and TRACK* indicate that a track gate is now in existence. Thus, a group of successive diode signals is selected which span the length of exactly one pellet.

As soon as the track gate signals come into existence, counters 916, 921 and 922 begin counting upward from the number present on the TG bus and produce an output which is fed to tri-state buffers 925, 928 and 931. The output of the latter is fed to leads DB0-DB7 and to leads DB0 and DB1 in two strokes. This output on the DB bus is fed to microprocessor 550 to provide an indication of the address of the track gate.

Figure 26:
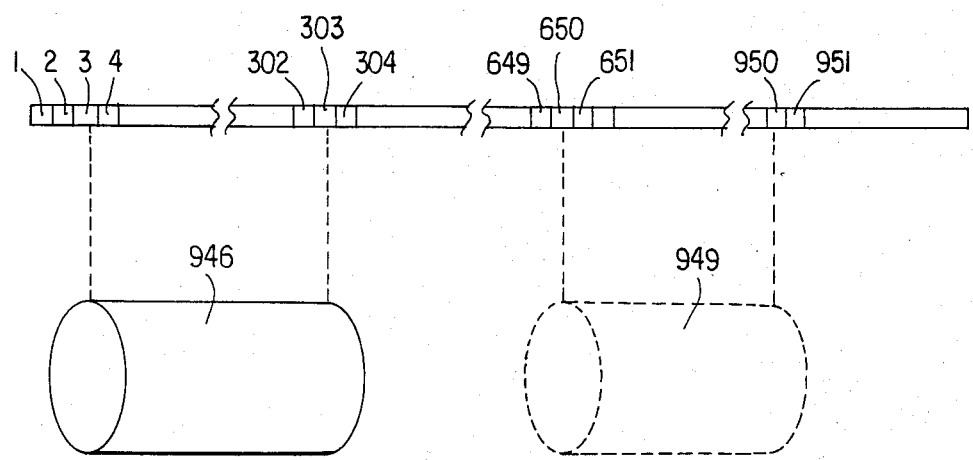
FIG. 26 is a schematic illustration of a photodiode array for reading the surface of a pellet.

The operation of the circuitry shown in FIG. 3 is further illustrated with reference to FIG. 26 in which the photodiode array 943 is shown schematically reading the surface of a pellet 946. The number strobed into counters 859, 862 and 865 from the AB bus is strobed in with two strokes by latches 850, 853 and 856 and it indicates the beginning of the track gate for the first scan of the pellets. For example, if the number on the AB bus were 3, then the track gate would begin at diode 3, namely the diode corresponding to an edge of pellet 946. In such a case, the information produced by diodes 1 and 2 would not be considered by the processing circuitry. On subsequent scans the pellet will have been advanced laterally, that is, axially along the roller supports, to a position such as that indicated by pellet 949, shown in ghost outline. The number fed by counters 859, 862 and 865 to the TG bus is advanced according to the pellet's axial velocity by signals present on leads VELP, SSX and C1 to increase the number fed to comparators 868, 871 and 874 by way of the TG bus. This changes the track gate's beginning address to one corresponding to the new position of the pellets.

For example, counters 859, 862 and 865 would be incremented upward from the number strobed into them on the AB bus by signals present on leads VELP, SSX or C1. This process will increment the number present on the TG bus to a number such as 650 shown in the drawing, such that the track gate will begin at diode 650. Diodes 1–649 will not be processed by the processing circuitry and only signals from diodes having addresses greater than 649 will be considered. Other circuitry described later determines the address at which the track gate is terminated so that diodes beyond the other edge of the pellet, such as 951–1024 with respect to pellet 946, will not be processed.

Tri-state buffers 907, 910 and 913 function to format data present on the TG bus and translate it to data of another form for transmission to the microprocessor on the MB bus. Thus, the beginning of the track gate determines the lowest address of diodes whose signals are to be processed. This lowest address is changed to accommodate pellet motion along the track so that each of the 220 scans of each pellet begins at the same distance from the pellet's end, regardless of the pellet's translation along the track.

FIG. 4 depicts circuitry which provides an address, measured from the beginning address of the track gate, of each diode whose signal is being processed. Lead C1* is connected to a clocking input of each of counters 950, 953 and 956. Lead START* is connected to a resetting input of each of said counters. Lead TRACK is connected to an enabling input of each of said counters. The outputs of counters 950, 953 and 956 are connected to tri-state buffers 959 and 962, as well as to comparators 965, 968 and 971. Tri-state buffers 959 and 962, as well as tri-state buffer 974 are connected to leads MBØ–MB15. Lead TRSTN* is connected to enabling inputs of these tri-state buffers. Lead ABØ–AB7 are connected to inputs of counters 977, 980 and 983 and lead STB22 is connected to clocking inputs of each of these counters. Leads ABØ and AB1 are connected to latch 986 and lead STB23 is connected to an enabling input of this latch.

The output of latch 986 is connected to an input of counter 983 and lead STB22 is connected to a clocking input of this counter. The outputs of counters 977, 980 and 983 are connected to comparators 965, 968 and 971, as well as to tri-state buffers 989, 992 and 995. Leads MBØ–MB15 are connected to tri-state buffers 989, 992 and 995. Leads STB16 and STB17 are connected respectively to the setting and resetting inputs of flip flop 998, the outputs of which are connected to leads TSØ and TSØ*. Leads STB16 and STB18 are connected respectively to the setting and resetting inputs of flip flop 1001 whose outputs are connected to leads TSI and TSI*. Leads TSØ and TS1 are connected to tri-state buffer 992. An output of comparator 971 is connected to an input of flip flop 1004, the clocking input of which is connected to lead C1*, and the output of which is connected to lead ENDTRACK*.

The operation of the above-described circuit shown in FIG. 4 is as follows: Lead START* sets counters 950, 953 and 956 to zero. Lead TRACK enables these counters which are clocked by lead C1*. Thus, let it be assumed when a diode is read whose address is given by the R bus in FIG. 3. If the address is equal to or greater than the track gate start address given by the TG bus, (which is comprised of the outputs of counters 859, 862 and 865), then counters 950, 953 and 956 in FIG. 4 are set to zero and they are enabled by the TRACK signal. At some other time, counters 977, 980 and 983 are set by strobe STB22 to a number determined by the AB bus. This number indicates the length of the track gate in terms of diode address units. The now-incrementing outputs of counters 950, 953 and 956 are compared with the fixed outputs of latches 977, 980 and 983 by means of comparators 965, 968 and 971. The comparison determines whether the address of the diode currently beginning read has exceeded the length of the track gate. If so, flip flop 1004 toggles and produces a signal on lead ENDTRACK* which indicates the end of the track gate. Thus, diodes having higher addresses will not be read. At this time tri-state buffers 989, 992 and 995 are strobed by lead RSS3*. Thus, the track gate length latched into latches 977, 980 and 983 is fed to leads MBØ–MB15.

During the existence of the track gate, the incrementing addresses of counters 950, 953 and 956 are fed to tri-state buffers 959 and 962. Tri-state buffer 974 contains data identity information. If a particular event occurs in the signal of a diode whose address is being read, a signal at lead TRSTN* will strobe tristate buffers 959, 962 and 974. As a result, the address of that diode and data identity information are fed to leads MBØ–MB15. This address information is used in the analysis of the diode signals as discussed hereinbelow. Thus, FIG. 4 depicts circuitry which provides the address of each diode whose signal is being read and the address is given with reference to the track gate address as the origin. For example, if in FIG. 26 the track gate begins at diode 3, counters 950, 953 and 956 indicate diode 3 as address number 0, diode 4 as address number 1 and so on. The address of each diode currently read is compared with a maximum address number such as 303 in FIG. 26 and given by latches 977, 980 and 983. When this maximum address number is reached, diode reading is terminated. At this time, the maximum address number is fed to the MB bus by tri-state buffers 989 and 992 and data identity information, is fed to the bus by tri-state buffer 995. For reasons discussed hereinbelow, the addresses of diodes providing particular signals of interest are transmitted to the MB bus by tri-state buffers 959 and 962, and data identity is provided by tri-state buffer 974.

PHOTO-DIODE SIGNAL ANALYSIS

Figure 5:
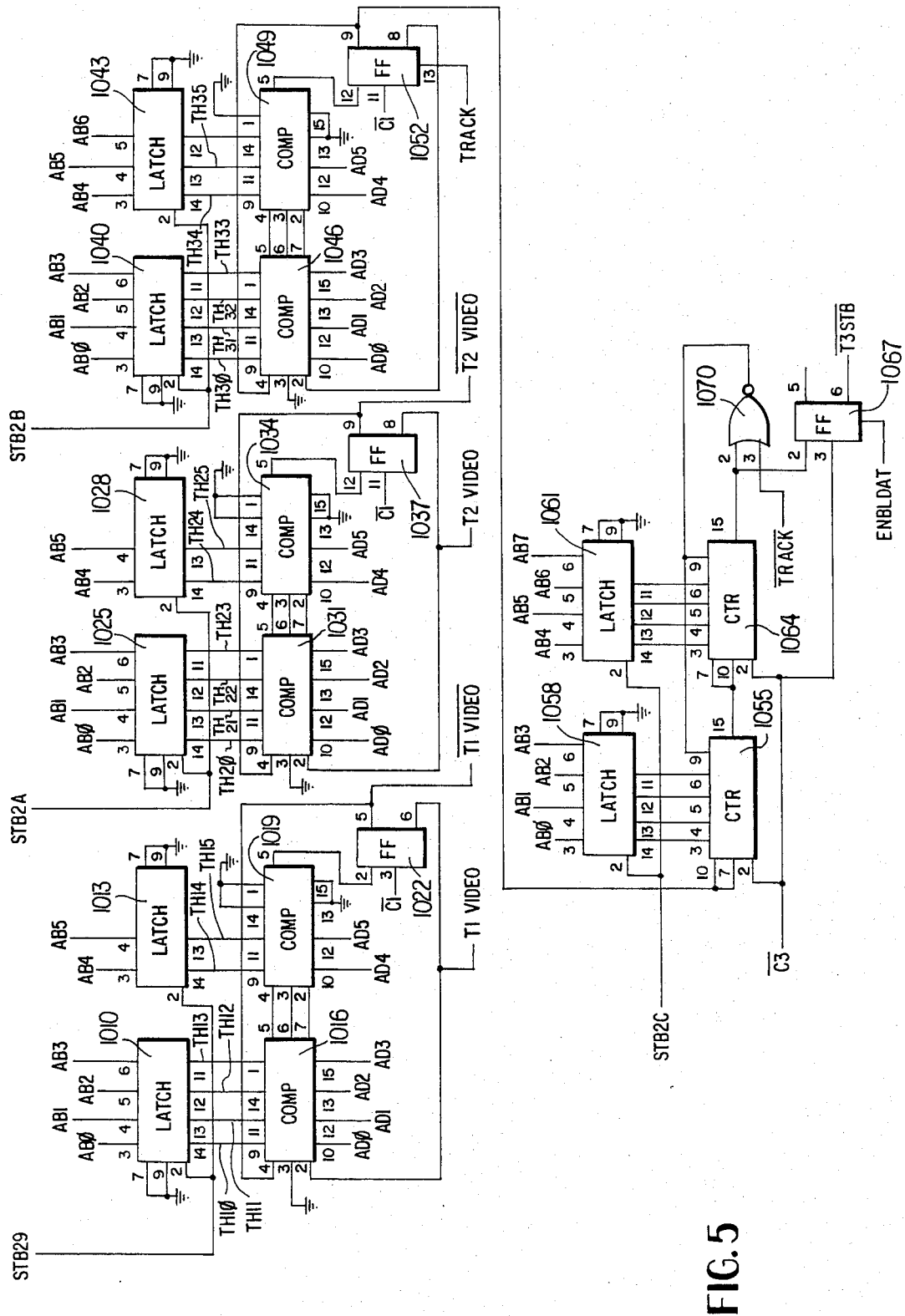
FIG. 5 illustrates circuitry for determining the output of the photosensitive diodes relative to predetermined threshold magnitudes.

FIG. 5 depicts circuitry utilized to determine whether the output of each photosensitive diode exceeds each of three predetermined threshold magnitudes. Circuitry is also shown which counts the number of times a particular threshold is exceeded. Leads ABØ–AB5 are connected to inputs of latches 1010 and 1013 and lead STB29 is connected to the latching input of each of the latches. The outputs of latches 1010 and 1013 are connected to leads TH1Ø–TH15, which are connected to inputs of comparators 1016 and 1019. Leads ADØ–AD5 are connected to the other inputs of comparators 1016 and 1019. Lead C1* is connected to the clocking input of flip flop 1022.

Leads ABØ–AB5 are connected to inputs of latches 1025 and 1028 and lead STB2A is connected to the latching inputs of each of these latches. The outputs of latches 1025 and 1028 are connected to leads TH20–TH25 which are coupled to the inputs of comparators 1031 and 1034. Leads ADØ–AD5 are connected to the other inputs of comparators 1031 and 1034 and lead C1* is connected to clocking input of flip flop 1037.

Leads ABØ–AB6 are connected to inputs of latches 1040 and 1043 and lead STB2B is connected to the latching input of each of said latches. The outputs of latches 1040 and 1043 are connected to leads TH30–TH35 which are connected to the inputs of comparators 1046 and 1049. Leads ADØ–AD5 are connected to the other inputs of comparators 1046 and 1049 and lead C1* is connected to a clocking input of flip flop 1052. An output of comparators 1016, 1031 and 1046 is connected respectively to an input of flip flops 1022, 1037 and 1052. One output of flip flop 1022 is connected to lead T1VIDEO and the other output of this flip flop is connected to lead T1VIDEO*. One output of flip flop 1037 is connected to lead T2VIDEO and the other output of this flip flop is connected to lead T2VIDEO*. Lead TRACK is connected to a setting input of flip flop 1052 and output 9 of this flip flop is connected to the enabling input of counter 1055.

Leads ABØ–AB7 are connected to inputs of latches 1058 and 1061 and lead STB2C is connected to the latching input of each of these latches. The outputs of latches 1058 and 1061 are connected to the inputs of counters 1055 and 1064. Lead C3* is connected to a clocking input of each of counters 1055 and 1064 as well as to an input of flip flop 1067. The output 15 of counter 1064 is connected to an input of a NOR gate 1070, as well as to the other input of flip flop 1067. Lead TRACK* is connected to another input of NOR gate 1070 and the output of this gate is fed back to counters 1055 and 1064. Lead ENBLDAT is connected to a setting input of flip flop 1067 and the output of flip flop 1067 is connected to lead T3STB*.

The operation of the circuit of FIG. 5 is explained as follows: Data present on the AB bus is strobed by STB29 into latches 1010 and 1013. This data is indicative of a predetermined threshold voltage termed T-1. Latches 1010 and 1013 feed the data to comparators 1016 and 1019, which compare the threshold with the actual weighted diode voltage values produced in response to the pellet under examination. These values are present on the AD bus, as supplied by latches 310 and 313 in FIG. 25. If the actual diode value exceeds the threshold value, input 2 of flip flop 1022 is triggered and the leads T1VIDEO and T1VIDEO*, each being the inverse of the other, acquire logic states indicative of the occurrence of this event. Thus, inquiry is made as to the conformance of pellet surface features, as indicated by diode signals, to a predetermined criterion, as indicated by the T-1 threshold.

The operation is similar in determining the existence of a diode voltage which exceeds a second threshold. Specifically, a threshold termed T2, indicated on the AB bus, is strobed into latches 1025 and 1028 by strobe STB2A. This data is fed to comparators 1031 and 1034 and is compared with the weighted diode values present on the AD bus. Should the actual weighted diode values exceed the threshold, flip flop 1037 is toggled and leads T2VIDEO and T2VIDEO* acquire logic values indicative of the occurrence.

Similarly, a third threshold, designated T3, is strobed into latches 1040 and 1043 by strobe STB3B from the data present on the AB bus. This latter data is fed to comparators 1046 and 1049, which compare the magnitude of threshold T3 with that of the actual weighted diode values present on the AD bus. If the actual diode values exceed the threshold, flip flop 1052 is toggled provided it is enabled by lead TRACK. The toggling action causes a signal to be fed to counter 1055 which together with counter 1064, begins counting at the number latched into the counters by latches 1058 and 1061.

In other words, every time a diode signal exceeds threshold T3, counters 1055 and 1064 are incremented upward from the numbers latched into them by latches 1058 and 1061. In particular, counters 1055 and 1064 count up to the count 255 and then feed back through the output of NOR gate 1070 and reset themselves at that time. Also, the disappearance of the track gate causes the output of the NOR gate 1070 to reload counters 1055 and 1064 in preparation for the reappearance of the track gate during a subsequent scan. Finally, when the output of counters 1055 and 1064 reaches the count 255, flip flop 1067 is toggled, provided it is enabled by lead ENBLDAT. This forces lead T3STB* to a logic state indicative of the occurrence of a specified number of diode excursions past threshold T3. The specified number is equal to 255 minus the number latched by latches 1058 and 1061.

Threshold T3 is relatively high and is taken to indicate the receipt by a diode of light which is sufficiently bright that it must have been produced by a shiny metal object, as for example, a metal inclusion in the pellet inspected. These occurrences are counted by counters 1055 and 1064. When a predetermined number of them has occurred, namely 255 minus the latch number of counters 1058 and 1061, a metal inclusion is deemed to exist. The latter condition is indicated by the logic state of lead T3STB* caused by the toggling of flip flop 1067. The signal T3STB* is further analyzed by circuitry discussed below.

Figure 11:
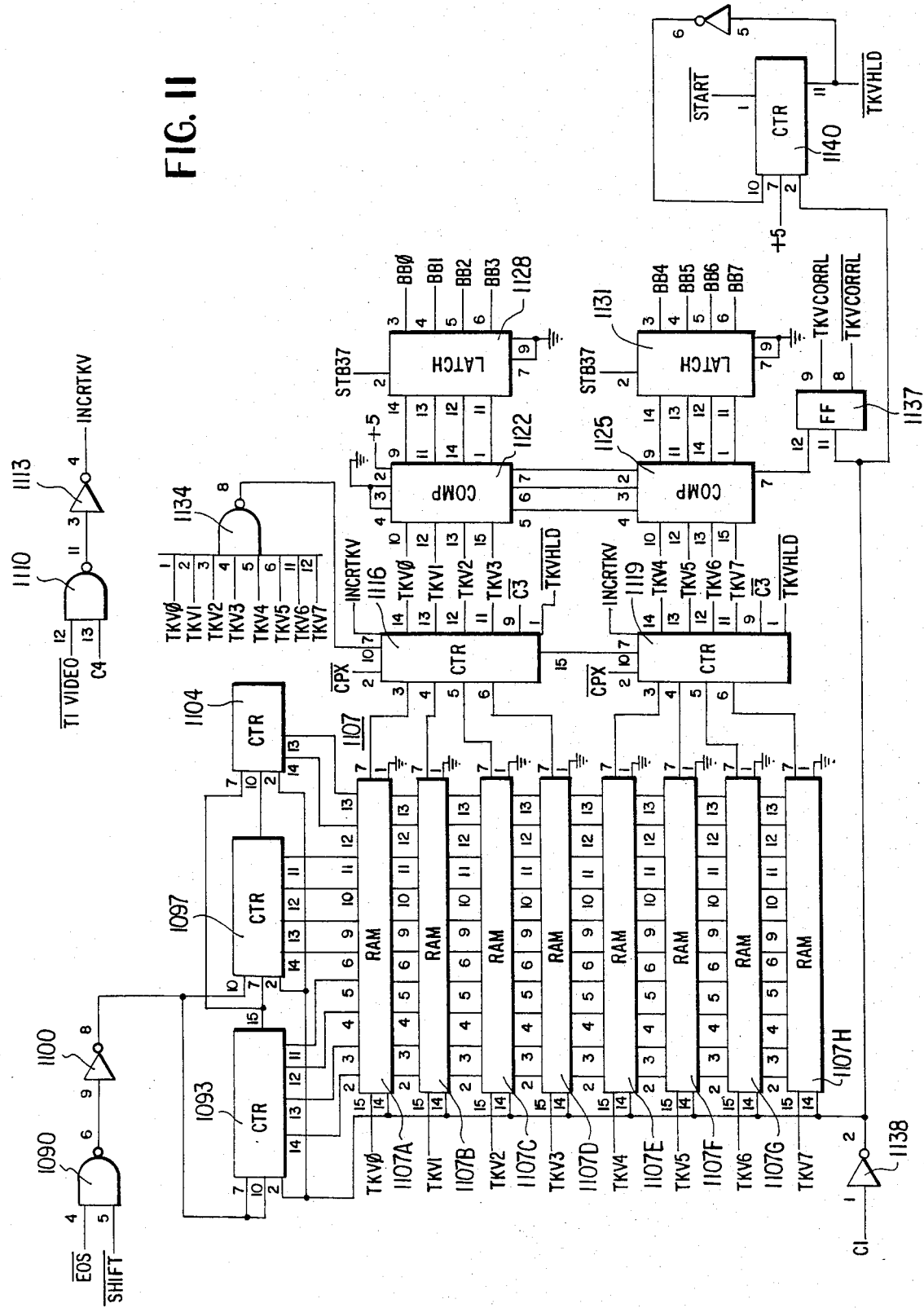
FIG. 11 illustrates a circuit for determining interfaces between adjacent pellets.

Leads T1VIDEO and T2VIDEO, and their complement leads identified above, produce signals which are analyzed by the circuitry illustrated in FIG. 11, which determines the locations of pellet-pellet interfaces by correlating the addresses of the occurrences of signals on lead T1VIDEO. In FIG. 11, leads EOS* and SHIFT* are each connected to inputs of NAND gate 1090 whose output is connected to incrementing inputs of counters 1093 and 1097 through inverter 1101. The outputs of counters 1093 and 1097, as well as that of counter 1104, are fed to the address-determining inputs of random access memory (RAM) 1107. RAM 1107 comprises individual RAMS 1107a–1107h whose address inputs are connected in parallel. Lead T1VIDEO* and lead C4 are each connected to inputs of NAND gate 1110 the output of which is fed through inverter 1113 to lead INCRTKV. This latter lead is connected to an incrementing input of counters 1116 and 1119. The output of counters 1116 and 1119 is connected to leads TKVØ–TKV7 which connect to the data inputs of RAM 1107. Leads TKVØ–7 are further connected to one set of inputs of comparators 1122 and 1125. The other set of inputs of these comparators is connected to the outputs of latches 1128 and 1131. Leads BBØ–BB7, originating at driver 650 illustrated in FIG. 2, are connected to the inputs of latches 1128 and 1131. Leads STB37 are connected to each of the latching inputs of latches 1128 and 1131. Leads TKVØ–7 are further connected to the inputs of a NAND gate 1134, the output of which is connected to an enabling input of counter 1116. Lead CPX* is connected to each of enabling inputs of counters 1116 and 1119. The output of comparator 1125 is connected to an input of flip flop 1137 whose outputs are connected to lead TKVCORRL and lead TKVCORRL*. Lead C1 is connected to an input of inverter 1138. The output of inverter 1138 is connected to the incrementing input of counter 1093, as well as to the enabling inputs of each of RAMs 1107a–1107h, to the clocking input of flip flop 1137, as well as to inputs of counters 1093, 1097 and 1104.

The operation of the above-described circuitry is as follows. Lead C1 exhibits a logic pulse each time a diode address changes. This pulse, as inverted by inverter 1138, is applied to the incrementing input of counters 1093, 1097 and 1104. It increments these counters whose output addresses successively increase address numbers in RAM 1107. Counters 1116 and 1119 are incremented upward by signals on lead INCRTKV, starting with the number read out of RAM 1107 at the address given by counters 1093, 1097 and 1104. Lead EOS* disables counters 1093, 1097 and 1104 so that no address changes occur after the end of diode array scan. Lead SHIFT* assures that counters 1093, 1097 and 1104 are operative only during the existence of a track gate pulse.

Meanwhile, latches 1128 and 1131, which are strobed by strobe STB37, feed the data contained on leads BBØ–BB7 to inputs of comparators of 1122 and 1125.

The data present on this BB bus indicates a predetermined number of T1VIDEO* events. The occurrence of each T1VIDEO* event is indicated by a logic swing of the same lead T1VIDEO*, which is connected to an input of NAND gate 1110. The output of the latter gate, provided input C4 is of a correct logic state to enable the output to appear, reflects the occurrence of the logic swing of lead T1VIDEO*. Thus lead INCRTKV undergoes a corresponding logic swing. This latter swing serves to increment counters 1116 and 1119, thus increasing by one the number present on leads TKVØ-TKV7. This TKV bus, as already mentioned, is connected simultaneously to inputs of comparators 1122 and 1125 and to data inputs of RAM 1107. Thus, as a number is read out of an address in RAM 1107, it is fed into counters 1116 and 1119. It may or may not be incremented by one of these counters due to a signal on lead INCRTKV. The number, incremented or not, is then fed back to the same address, thereby storing the number of T1VIDEO events occurring at the corresponding address on the diode array.

The particular method of establishing an interface by correlation of the addresses of T1VIDEO events will be illustratd by an example. As mentioned, counters 1093, 1097 and 1104 increment through all diode addresses whose signals are analyzed. These counters repeat this cycle for each pellet scan. It is assumed that at diode number 20, for example, in each scan a dark space occurs. Thus, as counters 1093, 1097 and 1104 increment from Ø to 19, the TKV data input bus to the RAM stores zero at each address, since no signal appears on lead INCRTKV. However, at address 20 of the first scan a signal appears on INCRTKV and a number 1 appears on the TKV bus. This number is stored at address 20 in the RAM and the signal on lead INCRTKV increments counters 1116 and 1119 from zero to one. Then counters 1093, 1097 and 1104 increment to the end of the track gate, e.g. number 400, and then restart at zero for the second scan. Again, nothing occurs on lead INCRTKV between addresses 1 to 19. However, at address 20 a signal appears on this lead and increments counters 1116 and 1119 from the number stored in RAM 1107 at address 20, namely, one to two. Thus, the number "2" appears on bus TKV and this number is fed back and stored as a "2" at the address 20 in the RAM. Again, zeroes will be stored at addresses 21-400. The process is carried out for 220 scans for each pellet, storing zeroes at all addresses between Ø and 19; storing the scan number, which is 220 at the end of all scanning at address 20; and storing zeros at addresses 21 through 400.

The existence of the interface is determined by comparing the number held on the TKV bus with that latched by the BB bus. While each pellet will be scanned 220 times, it is not considered necessary that an INCRTKV signal occur at the same address in every scan for an interface to exist. In the example above, the occurrence of perhaps 175 signals on lead INCRTKV at address 20 would be sufficient. The number considered sufficient is present on the BB bus latched by latches 1128 and 1131. When the count of INCRTKV events occurring at a given address reaches that number, comparators 1122 and 1125 issue a signal to flip flop 1137. This action toggles outputs TKVCORRL and its complement, to indicate the existence of a correlation at the address in RAM 1107 from which the number is read.

Figure 12:
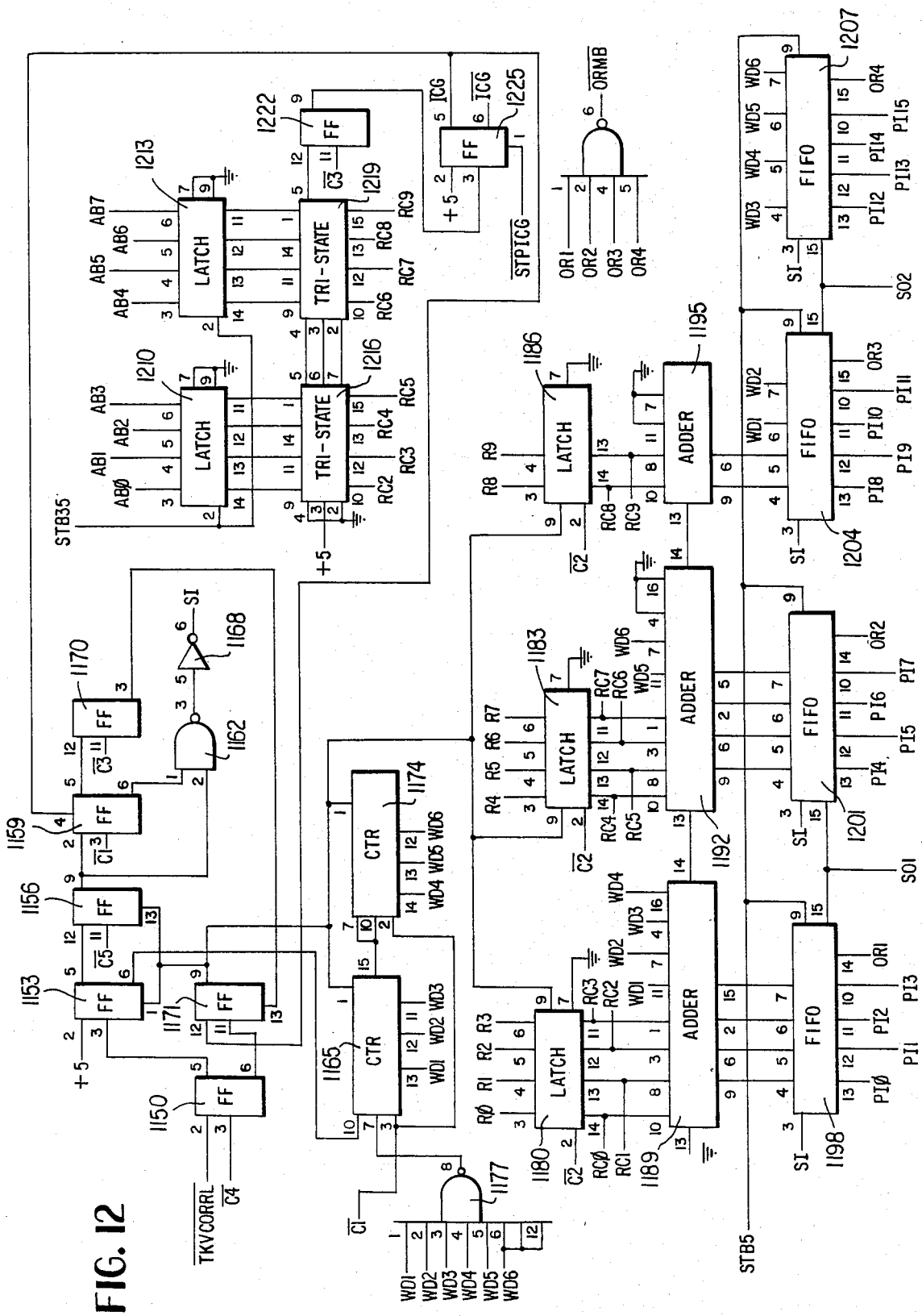
FIG. 12 illustrates circuitry for determining the address at which interface correlations are found to occur.

The method by which the correlation is determined will now be clear from the discussion above. FIG. 12 illustrates circuitry for determining the address at which the interface correlation is found to occur. Lead TKVCORRL* is connected to an input of flip flop 1150 whose clocking input is connected to lead C4*. An output of flip flop 1150 is connected to the clocking input of flip flop 1153 one of whose outputs is connected to an input of flip flop 1156 from which an output thereof is connected to both an input of flip flop 1159 as well as to an input of NAND gate 1162. The other output of flip flop 1153 is connected to an enabling input of counter 1165 and an output of flip flop 1159 is connected to an input of NAND gate 1162 whose output is connected to lead SI by way of inverter 1168. The other output of flip flop 1159 is connected to an input of flip flop 1170 whose output is connected to a setting input of flip flop 1171 the clocking input of which is connected to an output of flip flop 1150. Lead C1* is connected to an incrementing input of counters 1165 and 1174 whose outputs are connected to leads WD1-WD6. Leads WD1-WD6 are further connected to inputs of NAND gate 1177 the output of which is conected to an enabling input of counter 1165.

Leads RØ-R9 are connected to inputs of latches 1180, 1183 and 1186 and lead C2* is connected to a latching input of these latches. The outputs of these latches are connected to inputs of binary adders 1189, 1192 and 1195. Selected connections between these latches and these binary adders are designated as leads RC2-RC9. Leads WD1-WD6 are also connected to inputs of these binary adders. The outputs of binary adders 1180, 1183 and 1186 are connected to inputs of shift registes 1198, 1201 and 1204. Leads WD1-WD6 are further connected to inputs of shift registers 1204 and 1207. The outputs of shift registers 1198 and 1201 are connected to leads PIØ-PI17, OR1 and OR2. Lead S01 is connected to an enabling input of these registers. Two leads of binary adder 1195 are connected to inputs of shift register 1204. The outputs of shift registers 1204 and 1207 are connected to leads PI8-PI15 as well as to leads OR3 and OR4. Lead S02 is connected to a clocking input of these shift registers.

Leads ABØ-AB7 are connected to inputs of latches 1210 and 1213 and lead STB35 is connected to a latching input of these latches. The output of latches 1210 and 1213 are connected to the inputs of comparators 1216 and 1219 whose other inputs are connected to leads RC2-RC9. The output of comparator 1219 is connected to an input of flip flop 1222 whose clocking input is connected to lead C3*. The output of flip flop 1222 is connected to the clocking input of flip flop 1225 and lead STPICG* is connected to a setting input of this flip flop. The outputs of flip flop 1225 are connected to leads ICG and its complement ICG*.

The operation of the circuit shown in FIG. 12 is as follows: The occurrence of a number of correlations at any address which exceeds the predetermined threshold number that is fed to latchs 1128 and 1131 (shown in FIG. 11) results in the triggering of flip flops 1150, 1153, 1156, 1159, 1170 and 1171 to enable counters 1165 and 1174. During the time these counters are enabled, they count the occurrence of pulses on lead C1*. As mentioned, such pulses occur at the change of diode addresses, and thus the counters count the number of diodes over which such correlation events occur.

NAND gate 1177 functions to disable counters 1165 and 1174 in the event that excessive correlations occur, as may be mistakenly the case when a region is considered too long to be meaningful. Counter output leads WD1–WD6 are connected such that the binary number appearing thereon is exactly half the number stored in the counters. The width number of the interface is divided by two because only half of it is ascribed to the pellet under examination. The other half is attributed to the abutting pellet. This number is fed into binary address 1189 and 1192 which subtract it from the number latched into latches 1180, 1183 and 1186. The resulting number is fed into shift registers 1198, 1201 and 1204. The half-width information present on the WD bus is fed into shift registers 1204 and 1207. Accordingly, this circuit counts the number of addresses at which sufficient correlations occur to warrant the conclusion that an interface exists. The number of correlations is divided by two and subtracted from the actual diode address at the beginning of the track gate. The resulting address, indicating the actual address of the interface, together with the half-width information is available for use by other circuitry at the PI bus which constitutes the output of the shift registers.

Figure 13:
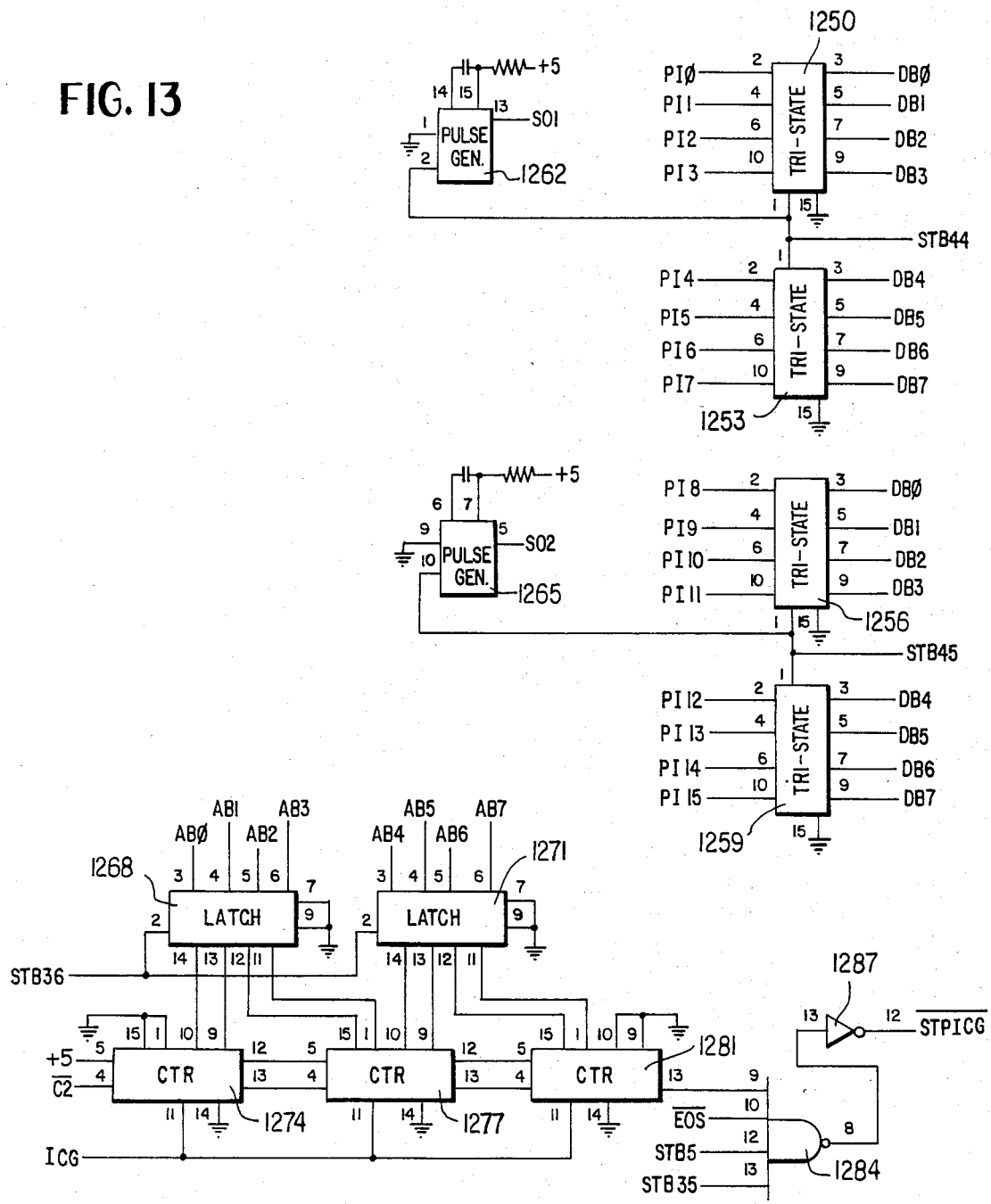
FIG. 13 illustrates circuitry for strobing data present on the PI bus into the DB bus and for limiting the areas on a pellet over which interface correlations are sought.

FIG. 13 illustrates circuitry utilized to strobe data present on the PI bus into the DB bus and circuitry used to limit the areas on a pellet over which interface correlations are sought. Leads PI∅–PI15 are connected to inputs of tri-state buffers 1250, 1253, 1256 and 1259 whose outputs are connected to the DB bus. Lead STB44 is connected to an enabling input of buffers 1250 and 1253 while lead STB45 is connected to enabling inputs of buffers 1256 and 1259. An input of pulse generator 1262 is connected to lead STB44 while an input of pulse generator 1265 is connected to lead STB45.

Leads A∅–AB7 are connectd to inputs of latches 1268 and 1271 and lead STB36 is connected to the latching inputs of these latches. The output of these latches is fed to down-counters 1274, 1277 and 1281 and lead ICG is connected to enabling inputs of these down-counters. Lead C2* is connected to a clocking input of down-counter 1274. The output of down-counter 128 together with leads EOS*, STB5, and STB35 are connected to inputs of NAND gate 1284. The output of NAND gate 1284 is connected to lead STPICG* by way of inverter 1287.

The operation of the circuit of FIG. 13, taken together with the pertinent portion of the circuit shown in FIG. 12, is as follows: Strobe 44 functions to strobe data contained on leads PI∅–P17 to part of the DB bus. Strobe 45 functions to strobe data contained on leads PI8–PI15 onto the remainder of the DB bus.

The number contained on the AB bus which is latched into latches 1268 and 1271 by strobe STB36 is the number at which down-counters 1274, 1277 and 1281 begin to count down when enabled by lead ICG. The down-counters are decremented at intervals determined by the timing of C2*, which is in time-displaced phase with the rate of diode address changes. When the downcounters have reached a predetermined number, the logic state of lead STPICG* changes and the signal change is coupled to flip flop 1225 in FIG. 12. Lead STPICG* set flip flop 1225 and thereby controls flip flop outsets puts ICG and ICG*. Flip flop 1225 is toggled by comparators 1216 and 1219, operating through flip flop 1222. These comparators compare the address of the diode whose signal, is currently being processd with the diode number latched in latches 1210 and 1213. When the address of the diode signal being processed exceeds that in latches 1210 and 1213, flip flop 1225 toggles. Leads ICG and ICG* are then used to terminate the search for interface correlation.

Thus, in summary interface correlation inquiry is only undertaken with respect to diode addresses above those latched into latches 1210 and 1213 of FIG. 12 and below those latched into latches 1268 and 1271 of FIG. 13. Thus, in searching for correlation over a limited region of a pellet, the situation of searching a region longer than a pellet with the accompanying possibility of finding correlations of both ends rather than one is eliminated.

The microprocessor 550 is programmed to establish imaginary interfaces indicating the leading edge of the first pellet and the trailing edge of the last pellet in the stack. This is done in conjunction with external optical transducers which indicate that the first or last pellet is approaching. The microprocessor then establishes the proper interface.

Figure 6:
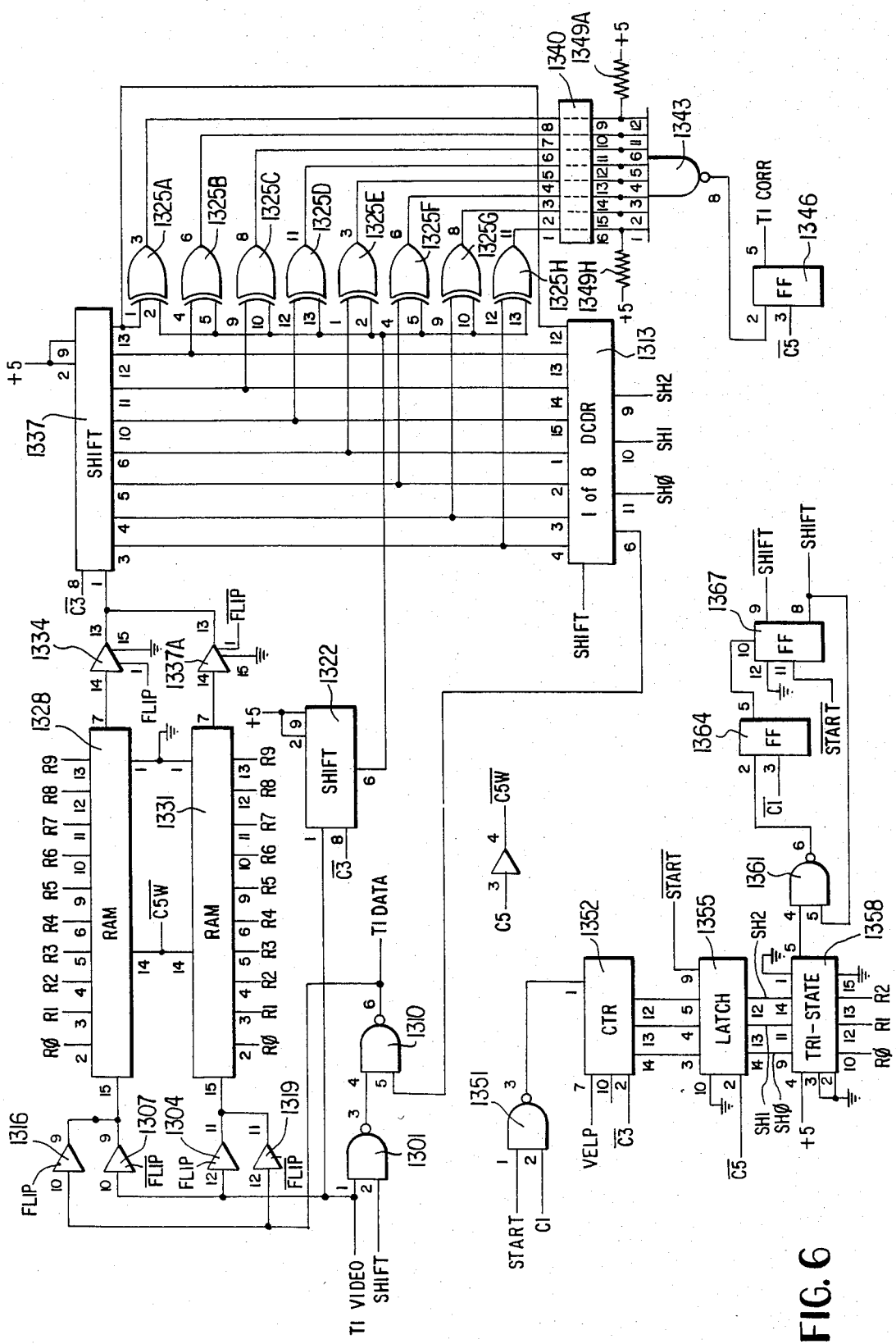
FIG. 6 illustrates circuitry for determining correlations between successive scans and for reporting the addresses of changes in correlation.

FIG. 6 illustrates circuitry used to determine correlations between successive scans and to report the addresses of changes in correlation. As shown, lead T1VIDEO is connected to an input of NAND gate 1301, as well as to inputs of tri-state buffers 1304 and 1307. Lead SHIFT is connected to the other input of NAND gate 1301. The output of NAND gate 1301 is connected to an input of NAND gate 1310, the other input of which is connected to an output of 8-to-1 decoder 1313. The output of NAND gate 1310 is connected to lead T1DATA, as well as to inputs of tri-state buffers 1316 and 1319. Lead T1VIDEO is further connected to the input of delay circuit 1322. Lead C3* is connected to a clocking input of the latter delay circuit.

The output of delay circuit 1322 is connected to an input of each of EXCLUSIVE-OR gates 1325a–1325h. outputs of both tri-state buffers 1307 and 1316 are connected to the data input of random acces memory (RAM) 1328 and the outputs of both tri-state buffers 1304 and 1319 are connected to the data input of RAM 133. Leads R∅–R9 are connected in parallel to the addressing inputs of both RAM's 1328 and 1331.

The output of RAM 1328 is connectd to an input of tri-state buffer 1334. The output of RAM 1331 is connected to an input of tri-state buffer 1337. Lead FLIP connects to the enabling inputs of tri-state buffers 1334, 1304 and 1316 and lead FLIP* connects to the enabling inputs of tri-state buffers 1337A, 1319 and 1307. The outputs of both tri-state buffers 1334 and 1337A are connected to the input of shift register 1337. Lead C3* is connected to the clocking input of this shift register.

Each output of shift register 1337 is connected to a different input of EXCLUSIVE-OR gates 1325a–1325h, as well as to each of the inputs of 8-to-1 decoder 1313. The outputs of EXCLUSIVE-OR gate 1325a–1325h are connected by way of jumper socket 1340 to the inputs of NAND gate 1343 the output of which is connected to input to flip flop 1346. Lead C5* is connected to the clocking input of flip flop 1346 the output of which is connected to lead T1CORR. Each output of EXCLUSIVE-OR gates 1325a–1325h is also connected to the 5 volt positive power supply through a resistor. Two of such resistors are shown connectd to the outputs of EXCLUSIVE-OR gates 1325a and 1325h and are designated 1349a and 1349h, respectively.

Lead START is connected to an input of NAND gate 1351 while lead C1 is connected to the other input of this NAND gate. The output of NAND gate 1351 is connected to the clocking input of counter 1352. Lead VELP is connected to an enabling input of counter 1352 and lead C3* is connected to a clocking input of this counter. The output of counter 1352 is connected to the input of latch 1355. Lead C5* is connected to the latching input of latch 1355 and lead START* is connected to the loading input of this latch.

The output of latch 1355 is connected to leads SH∅, SH1 and SH2, as well as to one set of inputs of comparator 1358. Leads R∅, R1 and R2 are connected to the other inputs of comparator 1358. The output of comparator 1358 is connected to an input of NAND gate 1361 the other input of which is connected to lead SHIFT. The output of NAND gate 1361 is connected to an input of flip flop 1364, the output of which is connected to resetting input of flip flop 1367. Lead C1* is connected to the clocking input of flip flop 1364 and lead START* is connected to the clocking input of flip flop 1367. The two outputs of flip flop 1367 are connected to leads SHIFT* and SHIFT.

The operation of the circuit of FIG. 6 is as follows: A signal present on lead T1VIDEO derived from flip flop 1022 in FIG. 5 indicates that the weighted diode signal of a diode located at an address indicated on the R bus has exceeded threshold T1. This signal is fed into one of RAM's 1328 or 1331 in FIG. 6 at the address contained on the R bus. The RAM selected depends on the signal path dictated by tri-state buffers 1316, 1307, 1304 and 1319, which are controlled by lead FLIP and FLIP*. Thus, either RAM 1328 or 1331 is loaded with T1 video signals for the duration of an entire scan.

Assuming that RAM 1328 is used, the data just stored in RAM 1328 is now used as reference data to determine the existence of correlations between it and data from subsequent scans. At the end of a scan tristate buffers 1316, 1307, 1304 and 1319 are triggered to load the data from the next scan into the other RAM, namely RAM 1331. Data from RAM 1328, which now comprises the reference scan, is sent through tri-state buffer 1334 into shift register 1337 at a rate determined by the clocking of lead C3*. Each data bit progresses along the outputs of shift register 1337 from left to right and is progressively applied to each input of EXCLUSIVE-OR gates 1325a–1325h, beginning with lowermost EXCLUSIVE-OR gate 1325h. The signal present on lead T1VIDEO is transmitted to delay means 1322 which delays the signal, preferably by four pulses of the signal on lead C3*, and then transmits it by means of lead 6 of the delay means to all the other inputs of EXCLUSIVE-OR gates 1325a–1325h. Thus, the signal on lead T1VIDEO, which indicates whether a particular diode output in the current scan exceeds threshold T1, is compared simultaneously with all of the signals of the four preceding diodes in the array, as well as to the signals of the four succeeding diodes by EXCLUSIVE-OR gates 1325a–1325h. The existence of correlation is shown by the logic state of lead T1CORR which is connectd to an output of flip flop 1346.

During the time when the information on T1VIDEO is being compared with the reference scan, namely that contained in RAM 1328 in the example above, the signals on lead T1VIDEO were simultaneously being loaded into the other RAM, i.e. RAM 1331. If the correlation between the reference scan and the current scan is perfect, this process of comparison is repeated for the following scan. That is, the data from a third scan is read into RAM 1331 as before and at the same time it is compared bit by bit with the preceding and succeeding four diode signals of reference scan data. As each new bit from the current scan is read into RAM 1331, the bit stored in RAM 1331 from the prior scan is erased. However, if a lack of correlation is found at an address, a signal appears at lead T1CORR. This signal is processed by the circuit described below.

Figure 18:
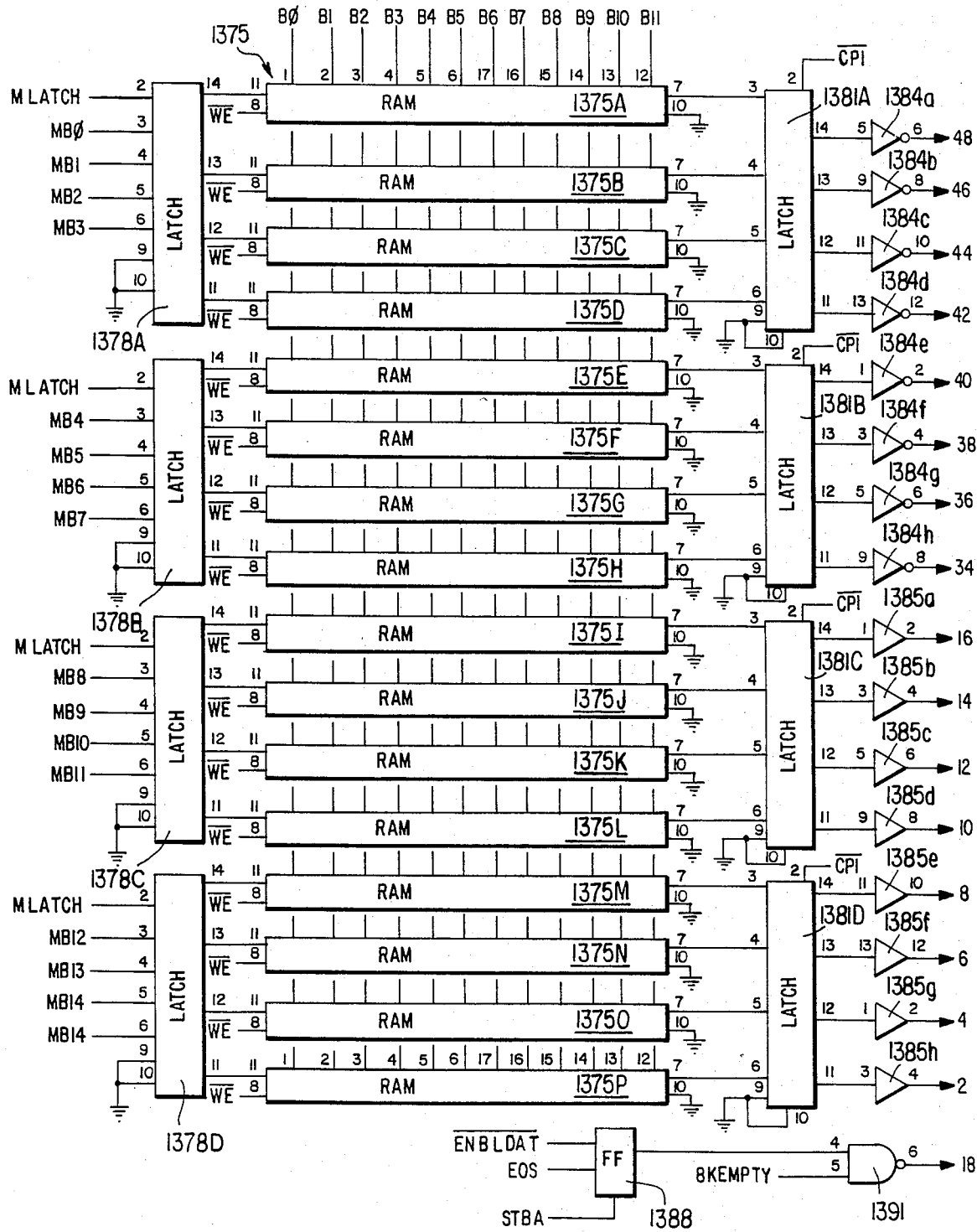
FIG. 18 illustrates a memory buffer for storing correlation data.

FIG. 18 illustrates a memory buffer used to store correlation data. Leads B∅–B11 are connected to the address inputs of RAM 1375. RAM 1375 comprises 16 individual RAM's 1375a–1375p. The address inputs of all these RAM's are all connected in parallel to the B bus. Latches 1378a, 1378b, 1378c and 1378d are interposed between leads MB∅–MB15 and are connected to the data inputs of RAM 1375. Lead MLATCH is connected to an enabling input of each latch 1378a–1378d. Lead WE* is connected to the write-enabling input of each individual RAM of RAM 1375. The output leads of each of RAM's 1375a–1375b are connected to latches 1381a, 1381b 1381c and 1381d. The outputs of latches 1381a and 1381b are connected to inputs of inverters 1384a–1384b and the outputs of latches 1381c and 1381d are connected to inputs of buffers 1385a–1385h. Lead CP1* is connected to a latching input of each of latches 1381a–1381d.

The outputs of inverters 1384a–1384h and of buffers 1385a–1385h are connected to peripheral devices not shown which are utilized for purposes such as data display. Lead ENBLDAT* and lead EOS are connected to inputs of flip flop 1388 whose setting input is connected to STBA. The output of flip flop 1388 is connected to an input of NAND gate 1391, the other input of which is connected to lead 8KEMPTY. The output of NAND gate 1391 is also connected to the peripheral display circuitry.

Figure 17:
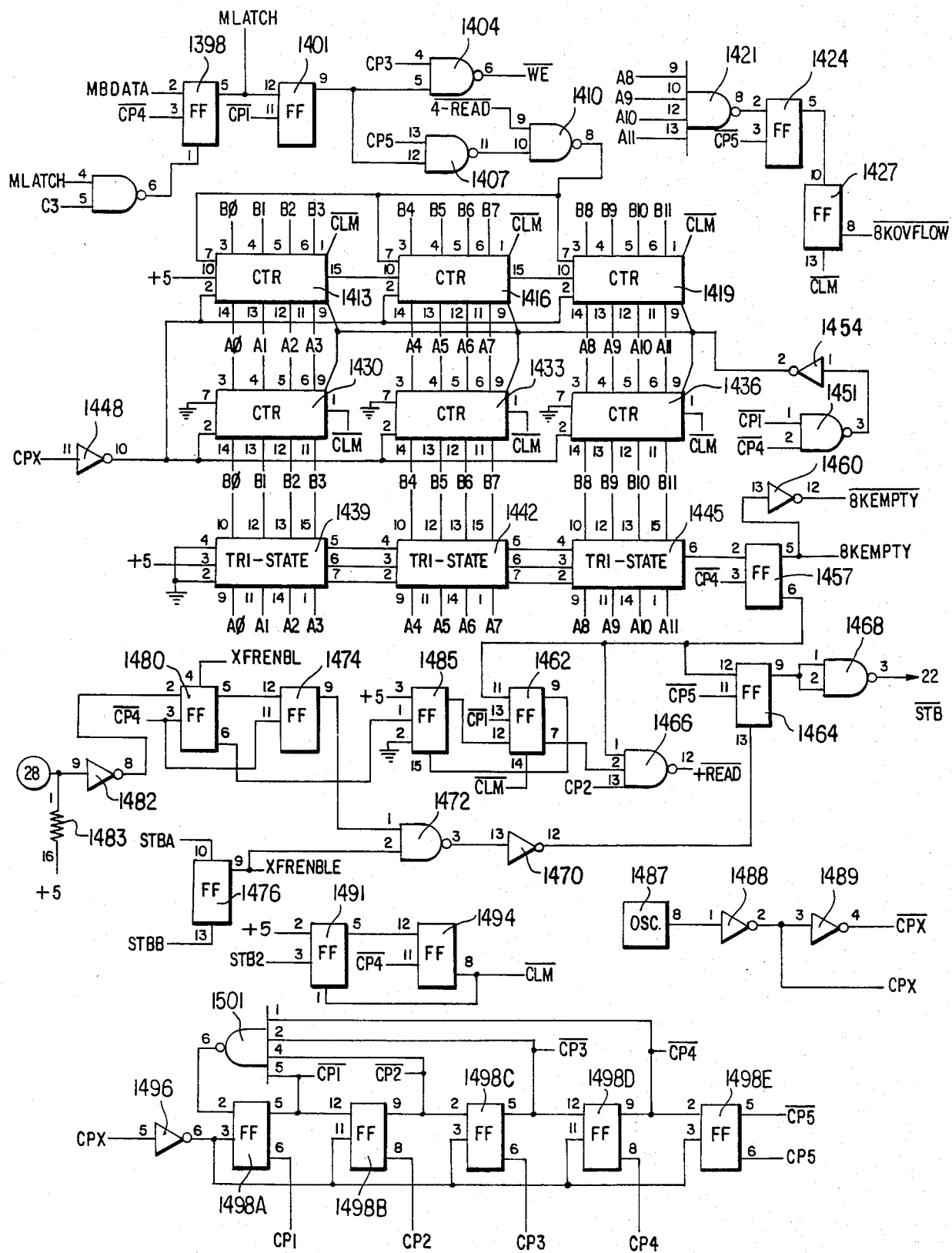
FIG. 17 illustrates a circuit for controlling the data reading and writing of RAM.

FIG. 17 illustrates a circuit used to control the data reading and writing of RAM 1375 of FIG. 18. Leads MLATCH and C3 are connected to inputs of NAND gate 1395 the output of which is connected to the setting of input of flip flop 1398. Leads MBDATA and CP4* are connected respectively to the input and clocking input of this flip flop the outputs of which are connected to both lead MLATCH and to an input of flip flop 1401. The clocking input of flip flop 1401 is connected to lead CP1*. The output of flip flop 1401 is connected to both an input of NAND gate 1404, as well as to an input of NAND gate 1407. The other input of NAND gate 1404 is connected to lead CP3 and the other input of NAND gate 1407 is connected to lead CP5.

The output of NAND gate 1404 is connected to lead WE* and the output of NAND gate 1407 is connected to an input of NAND gate 1410. The other input of gate 1410 is connected to lead 4-READ*. The output of NAND gate 1410 is connected to enabling inputs of each of counters 1413, 1416 and 1419. Leads A8–A11 are connected to inputs of NAND gate 1421. The output of the latter is connected to an input of flip flop 1424 whose clocking input is connected to lead CP5*. The output of flip flop 1424 is connected to a resetting input of flip flop 1427. The setting input of unit 1427 is connected to lead CLM*, while the outout of this flip flop is connected to lead 8KOVFLOW*.

Leads B∅–B11 are connected to inputs of latches 1413, 1416 and 1419. The outputs of these latches are connected to leads A∅–A11 as well as to inputs of counters 1430, 1433 and 1436. The outputs of counters 1430, 1433 and 1436 are connected back to leads B∅–B11 as well as to inputs of comparators 1439, 1442 and 1445. The other inputs of comparators 1439, 1442 and 1445 are connected to leads A∅–A11. Lead CPX is connected to an input of inverter 1448, the output of which is connected to the incrementing input of each of counters 1413, 1416, 1419, 1437, 1433 and 1436. Lead CLM* is connected to clearing input of each of these six counters. Leads CP1* and CP4* are connected to inputs of NAND gate 1451 the output of which is connected to an input of inverter 1454. The output of inverter 1454 is connected to the loading inputs of each of the six counters.

The output of comparator 1445 is connected to an input of flip flop 1457, the clocking input of which is connected to lead CP4*. One output of flip flop 1457 is connected to lead 8KEMPTY and also connected to an input of inverter 1460 the output of which is connected to lead 8KEMPTY*. The other output of flip flop 1457 is connected to an input of flip flop 1464, to the clocking input of flip flop 1462, and to an input of NAND gate 1466. Lead CP5* is connected to clocking input of flip flop 1464 the output of which is connected to both inputs of NAND gate 1468 whose output is connected to lead STB*. The setting input of flip flop 1464 is connected to the output of inverter 1470, the input of which is connected to the output of NAND gate 1472. One input of the latter gate is connected to lead XFRENBL and the other input is connected to the output of flip flop 1474. Lead XFRENBL is the output of flip flop 1476 whose resetting and setting inputs are connected respectively to leads STBA and STBB. Lead CP4* is connected to the clocking inputs of both flip flops 1474 and 1480. The other input of flip flop 1474 is connected to an output of flip flop 1480.

The resetting input of flip flop 1480 is connected to lead XFRENBL and the other input of this flip flop is connected to the output of inverter 1482. The input of unit 1482 is connected to the 5 volt positive power supply through resistor 1483, as well as to the peripheral display equipment. An output of flip flop 1480 is connected to the clocking input of flip flop 1485 whose output is connected to an input of flip flop 1462. Another input of flip flop 1462 is connected to lead CLM*, and the enabling input of flip flop 1485 is connectd to an outout of flip flop 1462. Lead CP2 is connected to an input of NAND gate 1466, as is an output of flip flop 1462.

The output of NAND gate 1466 is connected to lead +READ*. The output of the 10 MHz oscillator 1487 is connected to the input of inverter 1488 whose output is connected to lead CPX as well as to an input of inverter 1489. The output of inverter 1489 is connected to lead CPX*. Lead STB2 is connected to the clocking input of flip flop 1491, the output of which is connected to an input of flip flop 1494. The clocking input of flip flop 1494 is connected to lead CP4* and the output of flip flop 1494 is connected to lead CLM* as well as to the setting input of flip flop 1491.

Lead CPX is connected to an input of inverter 1496, the output of which is connected to a clocking input of each of flip flops 1498a, 1498b, 1498c, 1498d and 1498e. An output of flip flop 1498a is connected to an input of flip flop 1498b, as well as to an input of NAND gate 1501. An output of flip flop 1498b is connected to an input of flip flop 1498c, as well as to an input of NAND gate 1501. An output of flip flop 1498c is connected to an input of flip flop 1498d, as well as to an input of NAND gate 1501. The output of flip flop 1498d is connected to an input of flip flop 1498e, as well as to NAND gate 1501. The output of NAND gate 1501 is connected to the remaining input of flip flop 1498a.

An output of flip flop 1498a is connected to lead CP1. An output of flip flop 1498b is connected to lead CP2. An output of flip flop 1498c is connected to lead CP3. An output of flip flop 1498d is connected to lead CP4 and an output of flip flop 1498e is connected to lead CP5. The other outputs of flip flops 1498a–1498d which are connected to the inputs of NAND gate 1501 are connected to leads CP1*–CP4* respectively. The other output of flip flop 1498e is connected to lead CP5*.

Figure 8:
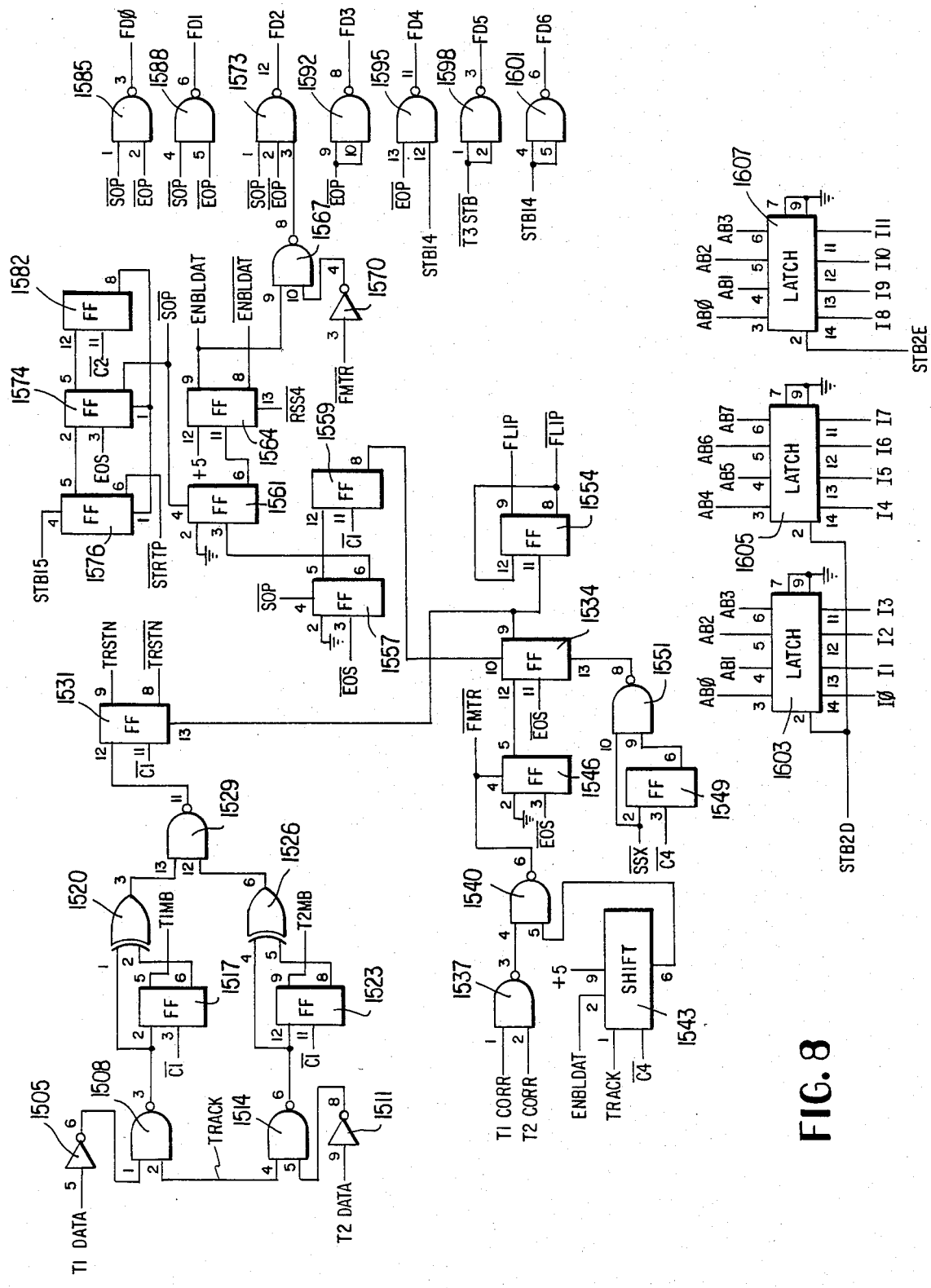
FIG. 8 illustrates circuitry for controlling data formatting in connection with the loading and unloading of a RAM shown in FIG. 18.

FIG. 8 illustrates circuitry used to control data formatting in connection with the loading and unloading of RAM 1375 in FIG. 18. Lead T1DATA is connected to an input of inverter 1505 the output of which is connected to an input of NAND gate 1508. Lead T2DATA is connected to an input of inverter 1511, the output of which is connected to an input of NAND gate 1514. Lead TRACK is connected to an input of each of NAND gates 1508 and 1514. The output of NAND gate 1508 is connected to an input of flip flop 1517, as well as to an input of EXCLUSIVE-OR gate 1520. The output of NAND gate 1514 is connected to an input of flip flop 1523, as well as to an input of EXCLUSIVE-OR gate 1526. The clocking inputs of flip flops 1517 and 1523 are connected to lead C1*.

An output of flip flop 1517 is connected to the other input of EXCLUSIVE-OR gate 1520, while an output of flip flop 1523 is connected to the other input of EXCLUSIVE-OR gate 1526. The other output of flip flop 1517 is connected to lead T1MB and the other output of flip flop 1523 is connected to lead T2MB. Both outputs of EXCLUSIVE-OR gates 1520 and 1526 are connected to inputs of NAND gate 1529. The output of the latter is connected to an input of flip flop 1531, the clocking input of which is connected to lead C1*. The outputs of flip flop 1531 are connected to leads TRSTN and to TRSTN*. The setting input of flip flop 1531 is connected to an output of flip flop 1534. This flip flop is connected to an output of flip flop 1576. The output of flip flop 1561 is connected to the clocking input of flip flop 1564, the other input of which is connected to the 5 volt positive voltage supply. The setting input of unit 1564 is connected to lead RSS4*.

One output of flip flop 1564 is connected to lead ENBLDT* while the other output is connected to lead ENBLDAT as well as to an input of NAND gate 1567. Lead FMTR* is connected to an input of inverter 1570, the output of which is connected to an input of NAND gate 1567. The output of the latter unit is connected to an input of NAND gate 1573. The other two inputs of NAND gate 1573 are connected to leads SOP* and EOP*. The output of NAND gate 1573 is connected to lead FD2. Lead STB15 is connected to the resetting input of flip flop 1576, an output of which is connected to lead STRTP*. Another output of flip flop 1576 is connected to an input of flip flop 1579, the clocking input of which is connected to lead EOS and an output of which is connected to lead SOP*. The other output of flip flop 1579 is connected to the input of flip flop 1582, the clocking input of which is connected to lead C2*. The output of flip flop 1582 is connected to setting inputs of both flip flops 1576 and 1579.

Leads SOP* and EOP* are connected to inputs of NAND gate 1585, the output of which is connected to lead FD∅. Leads SOP* and EOP* are both connected to inputs of NAND gate 1588, the output of which is connected to lead FD1. Lead EOP* is connected to both inputs of NAND gate 1592. The output of gate 1592 is connected to lead FD3.

Leads T1CORR and T1CORR are connected to inputs of NAND gate 1537, the output of which is connected to an input of NAND gate 1540. Leads ENDB-LDAT, TRACK and C4* are connected to inputs of delay means 1543, the output of which is connected to an input of NAND gate 1540. The output of NAND gate 1540 is connected to lead FMTR*, as well as to the resetting input of flip flop 1546. The clocking input of the latter is connected to lead EOS*. The output of flip flop 1546 is connected to an input of flip flop 1534, the clocking input of which is connected to lead EOS*. Lead SSX* is connected to an input of flip flop 1549, the clocking input of which is connected to lead C4*. The output of flip flop 1549 is connected to an input of NAND gate 1551. Lead SSX* is further connected to the other input of NAND gate 1551, the output of which is connected to a setting input of flip flop 1534. The output of flip flop 1534 is connected to the clocking input of flip flop 1554. One output of unit 1554 is connected to lead FLIP and the other output is connected to both lead FLIP* and to the other input of this flip flop. Lead EOS is connected to the clocking input of flip flop 1557, the other input of which is grounded. The resetting input of flip flop 1557 is connected to lead SOP*. One output of flip flop 1557 is connected to an input of flip flop 1559. The other output of flip flop 1557 is connected to the clocking input of flip flop 1561.

Lead C1* is connected to the clocking input of flip flop 1559, the output of which is connected to the resetting input of flip flop 1534. The other input of flip flop 1561 is grounded and the resetting input of Lead EOP* and STB14 are connected to inputs of NAND gate 1505, the output of which is connected to lead FD4. Lead T3STB* is connected to both inputs of NAND gate 1598, the output of which is connected to lead FD5. Lead STB14 is connected to both inputs NAND gate 1601, the output of which is connected to lead FD6. The inputs of latches 1603, and 1605 are connected to leads AB0-AB7 and the inputs of latch 1607 are connected to leads AB0-AB3. The outputs of latches 1603 and 1605 are connected to leads I0-I7 and the outputs of latch 1607 are connected to leads I8-I11. Lead STB2D is connected to the latching inputs of latches 1603 and 1605, while lead STB2E is connected to the latching inputs of latch 1607.

The operation of the above-described circuitry, in conjunction with the correlation-determining circuitry of FIG. 6, is as follows: Flip flop 1531 FIG. 8 toggles if the signal on lead T1DATA changes. This flip flop is enabled by flip flop 1534, which in turn responds to correlation occurrences indicated by signals on lead T1CORR. Futher, flip flop 1554 toggles if prompted by a signal on lead T1CORR to provide signals on leads FLIP and FLIP* which have the effect of changing the path of data from lead T1VIDEO from either of RAM's 1328 or 1331 to the other. In other words, a new reference scan is designated by signals on leads FLIP and FLIP*. Should a failure of correlation occur between the current scan and the reference scan, the diode address of this failure is written into RAM 1375 in FIG. 18 by means of leads MB0-MB15. This information is stored by RAM 1375 at an address determined by leads B0-B11. This address is chosen by circuitry in FIG. 17. Counters 1413, 1416, 1419, 1430, 1433 and 1436 have the characteristic that the number stored in them can be read out at the same time at which a new number is being written into them as ordered by their clocking inputs. Thus, a number can be transferred from latches 1413, 1416, 1419 to the inputs of latches 1430, 1433 and 1436, while the outputs of latches 1430, 1433 and 1436 are transferred to the inputs of latches 1413, 1416 and 1419. Thus, leads B0-B11 function to select an address of RAM 1375 in FIG. 18 for writing in the diode address of a T1 correlation event.

In order to retrieve this stored information from RAM 1375, the numbers present on leads A0-A11 are transferred to leads B0-B11 in FIG. 17. Comparators 1439, 1442 and 1445 compare the number on the A bus with that on the B bus and generate signals on leads 8KEMPTY and 8KEMPTY* indicating whether the two numbers are equal or not: Accordingly, this circuitry functions to load information concerning T1 correlation events into sequential addresses of RAM 1375, with the result that the adjacency of addresses at which information is stored in RAM 1375 is interpreted as indicating that the information denotes the beginning and end of a particular artifact contained on the surface of the pellet examined. This results from the fact that at the beginning of an artifact a T1 correlation event occurs because the diode signal at this point does not agree with the stored signal in the reference scan. Thus, data is compressed in that only selected beginning and end points of artifacts are recorded; points therebetween are ignored. Reporting only these peripheral points allows the data rate to be collapsed.

The diode address is stored in RAM 1375. However, the diode signals reported during the duration of the artifact are not stored because they are deemed redundant. The next signal which is stored is that from the diode at which the artifact stops and this diode address is stored in RAM 1375. Therefore, a linear artifact of a width equal to that of the width scanned by the photodiode array, will be recorded in RAM 1375 as two addresses, namely the beginning and the end. A rectangular artifact of substantial width will be recorded by the diode addresses and scan numbers of its four corners, and so on.

Figure 7:
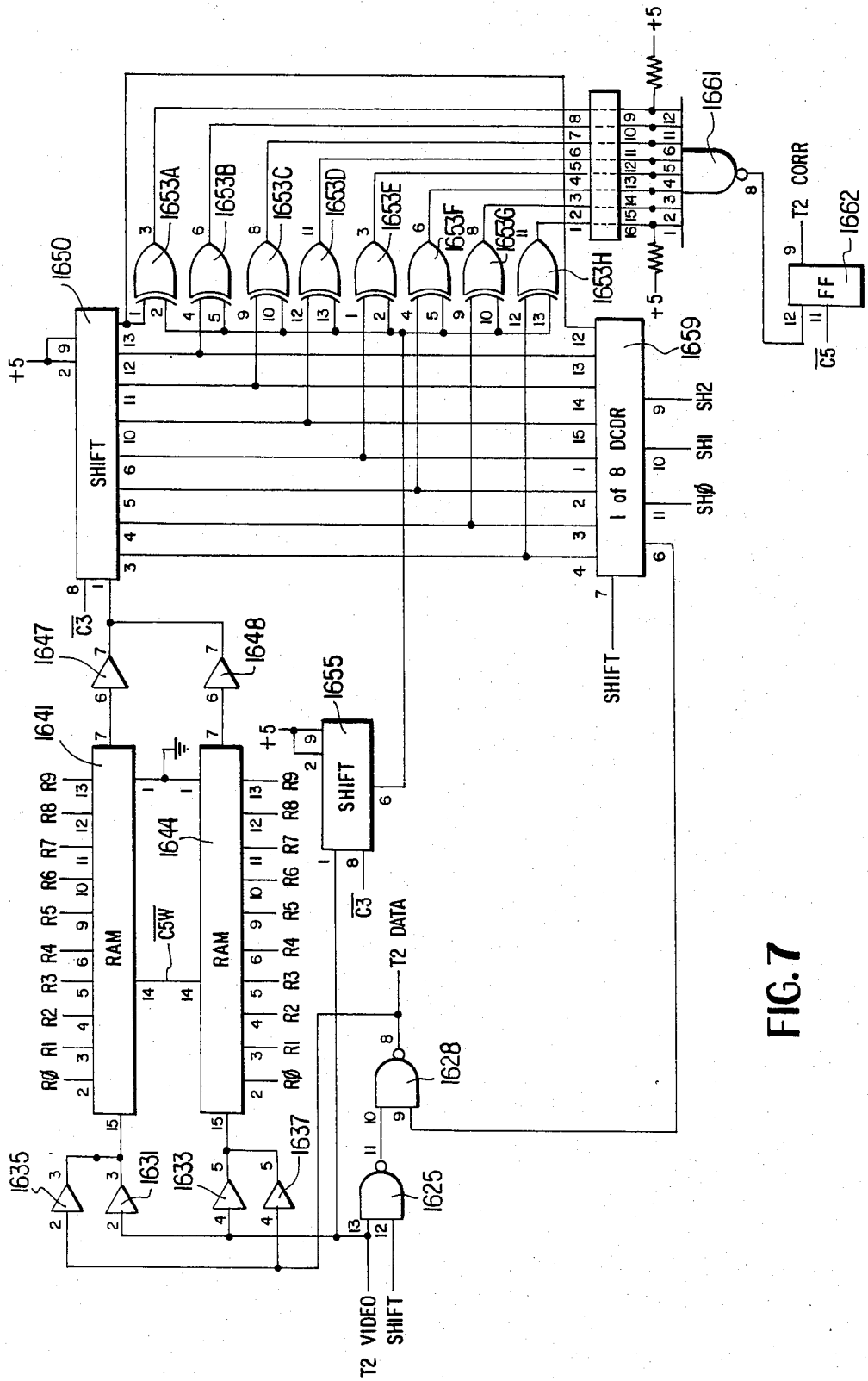
FIG. 7 illustrates circuitry for determining the existence of the correlation of events at which diode signals exceed a predetermined threshold.

FIG. 7 illustrates circuitry utilized to determine the existence of the correlation of events at which diode signals exceed the T2 video threshold. Lead T2VIDEO and lead SHIFT are connected to inputs of NAND gate 1625, the output of which is connected to an input of NAND gate 1628. Lead T2VIDEO is also connected to inputs of tri-state buffers 1631 and 1633. The output of NAND gate 1628 is connected to inputs of tri-state buffers 1635 and 1637. The output of tristate buffers 1631 and 1635 are connected to the data input of RAM 1641, while the outputs of tri-state buffers 1633 and 1637 are connected to data inputs of RAM 1644. The addressing inputs of RAM's 1641 and 1644 are connected in parallel to leads R0-R9. The output of RAM 1641 is connected to tri-state buffer 1647 and the output of RAM 1644 is connected to tri-state buffer 1648. The outputs of both tri-state buffers 1647 and 1648 are connected to the input of shift register 1650. The outputs of shift register 1650 are each connected to an input of different EXCLUSIVE-OR gates 1653a–1653b. Lead T2VIDEO is also connected to an input of delay means 1655, the clocking input of which is connected to lead C3*. The output of delay means 1655 is connected to an input of each of EXCLUSIVE-OR gates 1653a–1653h. The outputs of shift register 1650 are further connected to the inputs of 8-to-1 decoder 1659, the clocking input of which is connected to lead SHIFT. The decoding inputs of decoder 1659 are connected to leads SH0, SH1 and SH2 and the output is connected to an input of NAND gate 1628. Outputs of EXCLUSIVE-OR gates 1653a–1653h are each connected to the 5 volt positive power supply by resistors. Two of such resistors, namely 1660a and 1660b are shown connected to outputs of EXCLUSIVE-OR gates 1653a and 1653b respectively. Outputs of EXCLUSIVE-OR gates 1653a–1653h are further connected to inputs of NAND gate 1661, the output of which is connected to an input of flip flop 1662. The clocking input of this flip, flop is connected to lead C5* and the output is connected to lead T2CORR.

The operation of the circuitry of FIG. 7 is similar to that of the corresonding circuitry of FIG. 6 and need not therefore be further described.

Figure 14:
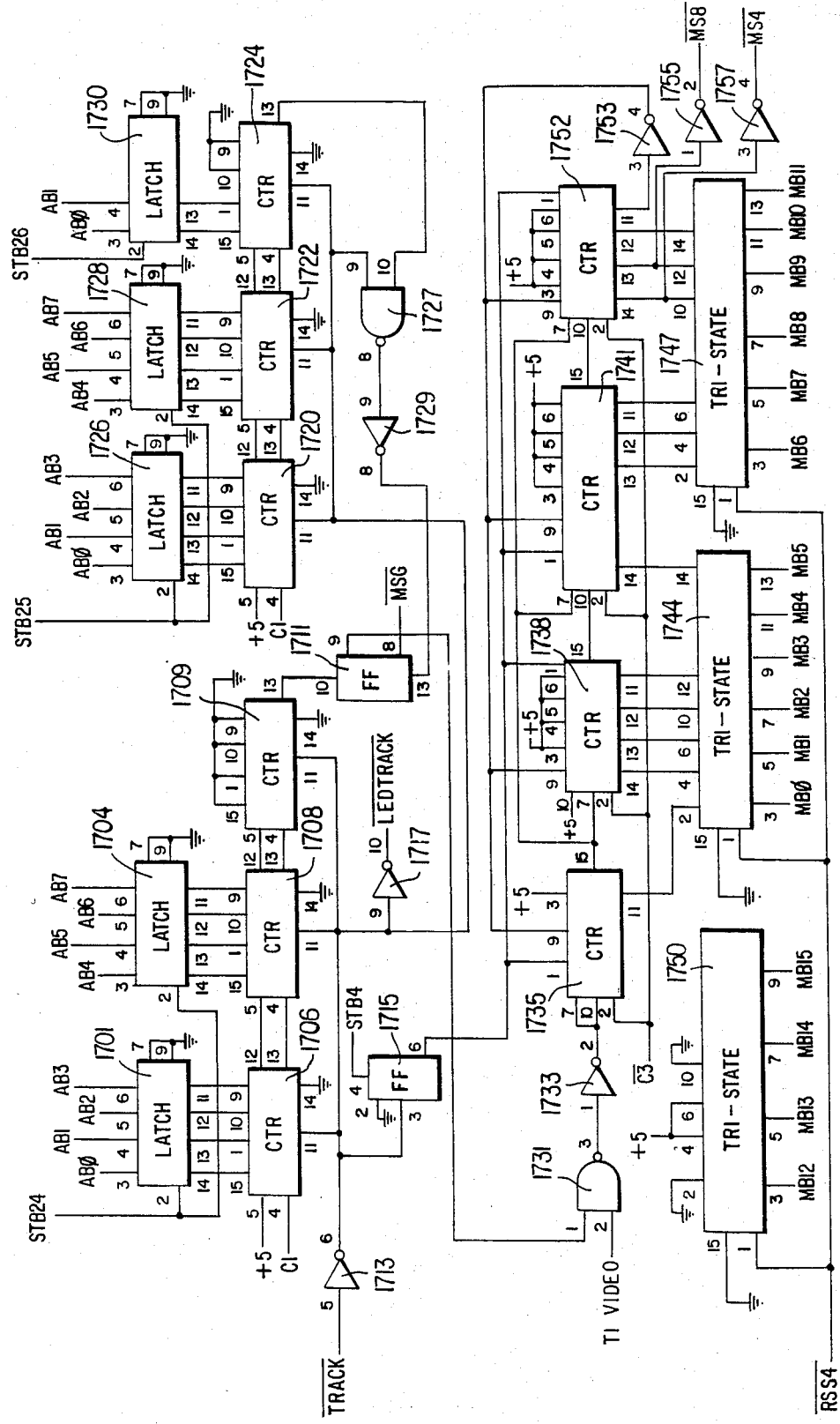
FIG. 14 illustrates a circuit for tallying areas of missing pellet surface.

FIG. 14 illustrates a circuit for tallying areas of missing pellet surface. Leads AB∅–AB7 are connected to the inputs of latches 1401 and 1404, the latching inputs of which are connected to lead STB24. The outputs of latches 1701 and 1704 are connected to inputs of down-counters 1706 and 1708. The inputs of down-counter 1709 are connected to ground and the output of this down-counter is connected to the resetting input of flip flop 1711. Lead TRACK* is connected to an input of inverter 1713, the output of which is connected to enabling inputs of down-counters 1706, 1708 and 1709.

Lead C1 is connected to the clocking input of down-counter 1706. The output of inverter 1713 is further connected to the clocking input of flip flop 1715, the resetting input of which is connected to lead STB4. The output of inverter 1713 is further connected to an input of inverter 1717 whose output is connected to lead LEDTRACK*. The inputs of down-counters 1720, 1722 and 1724 are connected to the outputs of latches 1726, 1728 and 1730, with the exception of leads 9 and 10 of counter 1724 which are connected to ground. The inputs of latches 1726 and 1728 are connected to leads AB∅–AB7 and the latching input of these latches is connected to lead STB25.

The inputs of latch 1730 are connected to leads AB∅ and AB1. The latching input of the latter latch is connected to lead STB26. The enabling inputs of down-counters 1720, 1722 and 1724 are connected to the output of inverter 1713 which output is also connected to an input of NAND gate 1727. The other input of NAND gate 1727 is connected to an output of down-counter 1724. The output of NAND gate 1727 is connected to an input of inverter 1729, the output of which is connected to the setting input of flip flop 1711. An output of flip flop 1711 is connected to lead MSG*. Another output of flip flop 1711 is connected to an input of NAND gate 1731. The other input of the latter gate is connected to lead T1VIDEO.

The output of NAND gate 1731 is connected to an input of inverter 1733, whose output is connected to the enabling inputs of counter 1735. Outputs of counters 1735, 1738 and 1741 are connected to tri-state buffers 1744 and 1747. The outputs of the latter are connected to leads MB∅–MB11. The outputs of tristate buffer 1750 are connected to leads MB12–MB15. Lead RSS4* is connected to enabling inputs of tri-state buffers 1744, 1747 and 1750. An output of counter 1752 is fed back to an input of counter 1735 through inverter 1753. Lead 13 of counter 1752 is further connected to an input of inverter 1755 whose output is connected to lead MS8*. Lead 14 of counter 1752 is connected to an input of inverter 1757, the output of which is connected to lead MS4*.

The operation of the circuit shown in FIG. 14 is as follows: It is desired to limit the portions of pellet surface which are inspected for areas of missing surface because certain areas such as the chamfered ends of the pellets can be misconstrued as exhibiting reflectivity properties characteristic of missing surfaces. Thus, latches 1701 and 1704 feed a number into down-counters 1706 and 1708, which represents the number of diode addresses by which a new gate, namely a missing surface gate, is offset from the leading edge of the track gate. Down-counters 1706, 1708 and 1709 are clocked by lead C1. When their output reaches zero, the missing surface gate comes into existence and allows counters 1735, 1738, 1741 and 1752 to count T1VIDEO events. These events are deemed to indicate occurrences of missing pellet surface.

At approximately the same time, a number contained in latches 1726, 1728 and 1730 is fed to downcounters 1720, 1722 and 1724 which begin counting at the time the missing surface gate comes into existence. They are clocked by lead C1 and for the interval during which they count from the number fed to them by latches 1726, 1728 and 1737 to the number zero, the missing surface gate is kept in existence. When these latches reach zero, a signal fed to flip flop 1711 toggles the flip flop and thereby prevents counting of T1VIDEO events by counters 1735, 1738, 1741 and 1752. The output of counters 1735, 1738, 1741 and 1752 is indicative of the total number of T1VIDEO events which occurred. After the entire pellet has been scanned, the number contained in these four counters is transmitted to leads MB∅–MB11 by means of tri-state buffers 1744 and 1747. Information from tri-state buffer 1750 is fed to leads MB12–MB15 and identifies the information on leads MB∅–MB11 as missing surface data.

Figure 15:
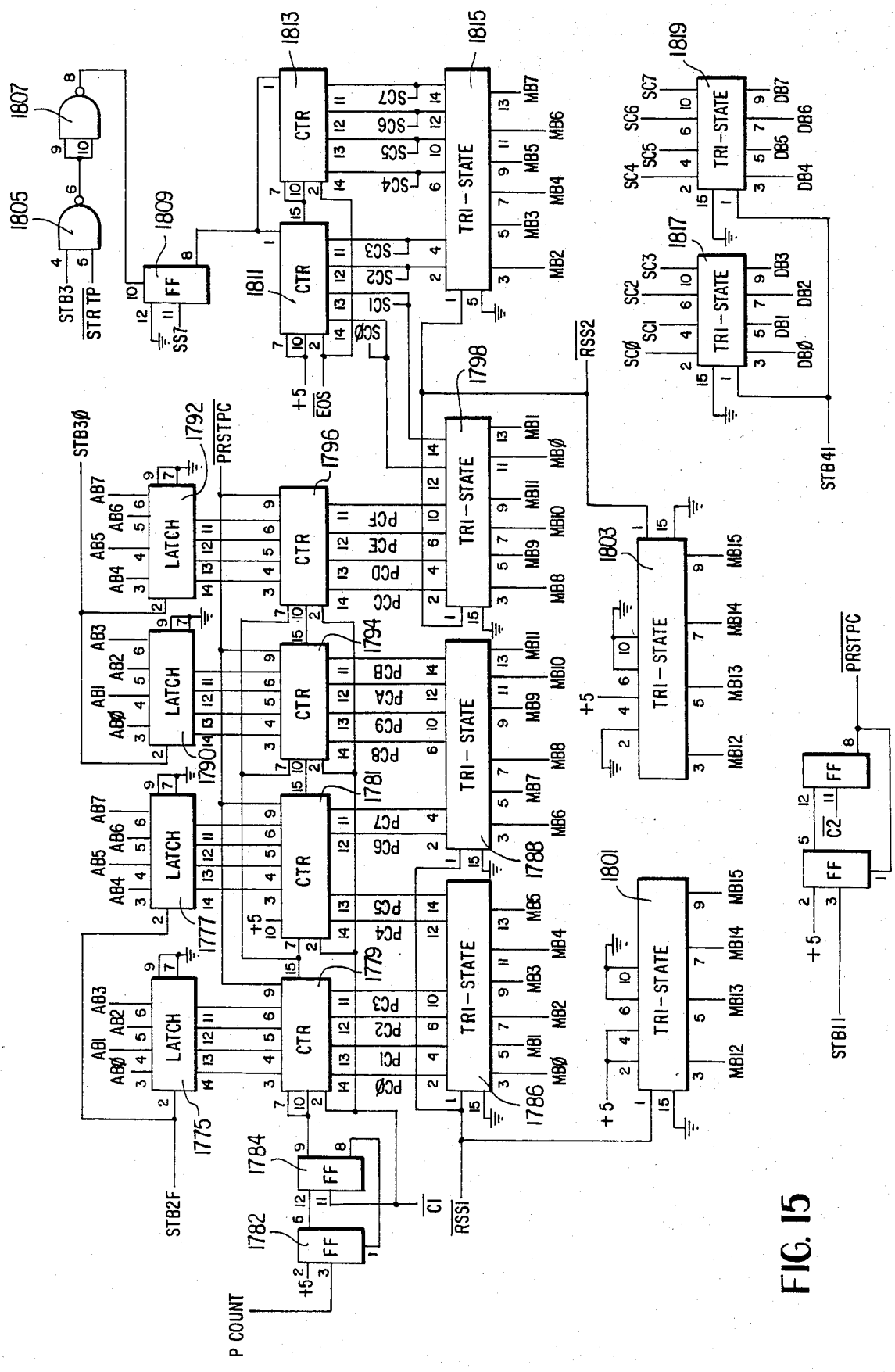
FIG. 15 illustrates a circuit for generating identification numbers for pellet-associated data and for the scans that produce such data.

FIG. 15 illustrates a circuit which generates a number to be associated with data corresponding to each pellet for identification of the data and, further, to generate a number identifying the scan which is producing the data. The scan number accordingly gives a circumferential coordinate while the diode address gives an axial coordinate. Of course, these two coordinates may refer to a diode currently being scanned or to the signal of a diode stored in memory. Leads AB∅–AB9 are connected to inputs of latches 1775 and 1777 and lead STB2F is connected to the latching input of these latches. The outputs of latches 1775 and 1777 are connected to inputs of counters 1779 and 1781 and lead C1* is connected to the clocking input of these counters. Lead PCOUNT is connected to the clocking input of flip flop 1782, the output of which is connected to an input of flip flop 1784. Lead C1* is connected to the clocking input of flip flop 1784. One output of flip flop 1784 is attached to the enabling input of counter 1779, while the other output of flip flop 1784 is fed back to the setting input of flip flop 1782.

The outputs of counters 1779 and 1781 are connected to tri-state buffers 1786 and 1788 whose outputs are connected to the MB bus. Leads AB∅–AB7 are connected to the inputs of latches 1790 and 1792. Lead STB30 is connected to the latching inputs of these latches. The outputs of latches 1790 and 1792 are connected to inputs of counters 1794 and 1796 and lead C1* is connected to the clocking inputs of these counters. The outputs of counters 1794 and 1796 are connected to inputs of tri-state buffers 1788 and 1798, the outputs of which are connected to the MB bus. Lead RSS1* is connected to the enabling input of tri-state buffers 1786 and 1788 and lead RSS2* is connected to the enabling input of tri-state buffer 1798.

Two inputs of tri-state buffer 1801 are connected to the 5 volt positive voltage supply to provide a logical "one" signal to these inputs. Two other inputs of buffer 1801 are connected to ground to providing logical "zero" to these inputs. The outputs of tri-state buffer 1801 are connected to leads MB12-MB15. Lead RSS1* is connected to an enabling input of this tri-state buffer.

One input of a tri-state buffer 1803 is connected to the 5 volt source and thus is held at logic ONE, while three other leads are connected to ground thus held at logic ZERO. The outputs of tri-state buffer 1803 are connected to leads MB12-MB15. Unit 1803 is enabled by lead RSS2*. Lead STB3 and lead STRTP* are connected to inputs of NAND gate 1805 the output of which is connected to both inputs of NAND gate 1807.

The output of gate 1807 is connected to the resetting input of flip flop 1809. Lead SS7 is connected to the clocking input of flip flop 1809, whose output is connected to clearing input of counters 1811 and 1813. Lead EOS* is connected to the clocking inputs of counters 1811 and 1813. The outputs of the latter counters are connected to leads SC∅-SC7 and also to inputs of tri-state buffers 1798 and 1815. The outputs of tri-state buffers 1798 and 1815 are connected to the MB bus. The enabling input of tri-state buffer 1815 is connected to lead RSS2*. Leads SC∅-SC7 are connected to tri-state buffers 1817 and 1819 whose enabling inputs are connected to lead STB41. The outputs of buffers 1817 and 1819 are connected to leads DB∅-DB7.

The operation of the circuit shown in FIG. 15 is as follows.

Prior to the first scan of a pellet, a signal from NAND gate 1807 clears counters 1811 and 1813. At the end of each scan, a pulse at lead marked EOS* increments counters 1811 and 1813, thereby providing a scan count number on leads SC∅-SC7. This signal is fed to the MB bus by signal present on lead RSS2*. Tri-state buffers 1817 and 1819 feed the scan count number to the DB bus which is connected to the microprocessor 550, as indicated by connections in FIGS. 1 and 1A, and these tri-state buffers are strobed by a signal present on lead STB41.

Lead PRSTPC* presets counters 1779, 1781, 1794 and 1796 to the numbers latched into them by latches 775, 1777, 1790 and 1792. Beginning with this number, counters 1779, 1781, 1794 and 1796 count upward, as clocked by signals on lead C1*. Thus a unique number is provided which can be associated with each pellet in the pellet string. Thus, data being processed by other circuitry can be associated with the pellet to which the data belongs.

Figure 10:
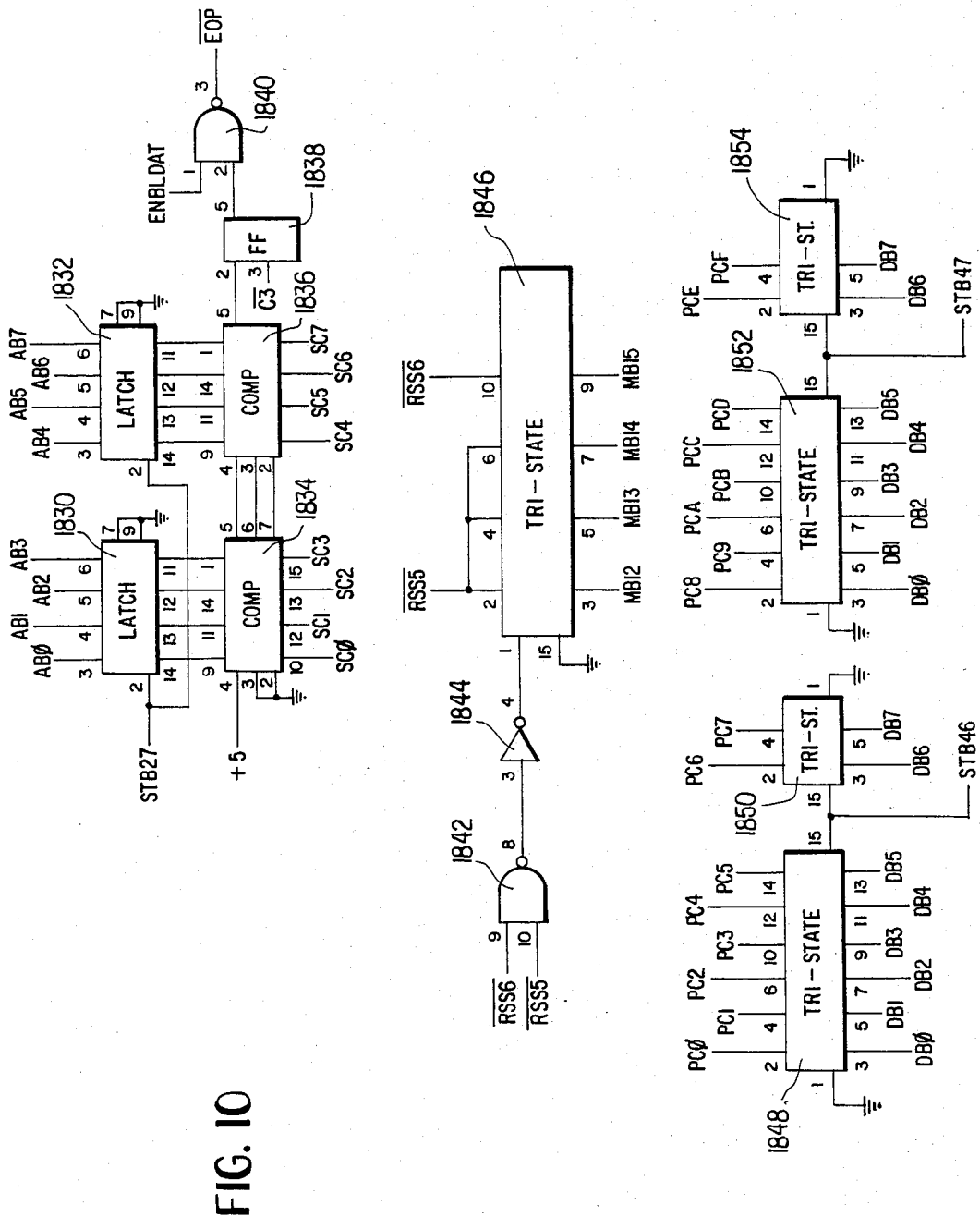
FIG. 10 illustrates a circuit for counting scan numbers; for feeding data identity information; and for strobing pellet position count data.

FIG. 10 illustrates a circuit which counts scan numbers to determine whether a full pellet has been scanned; which feeds data identity information to be associated with certain data transmitted on the MB bus; and which strobes pellet position count data to the DB bus for the microprocessor to use. Leads A-AB7 are connected to inputs of latches 1830 and 832 and lead STB27 is connected to the latching inputs thereof. The outputs of latches 1830 and 1832 are connected to one set of nputs of comparators 1834 and 1836 and the other set of inputs of these comparators is connected to leads SC∅-SC7. The output of comparator 1836 is connected to an input of flip flop 1838, the clocking input of which is connected to lead C3*. The output of flip flop 1838 is connected to an input of NAND gate 1840, the other input of which is connected to lead ENDBLDAT. The output of NAND gate 1840 is connected to lead EOP*.

Lead RSS6* and RSS5* are each connected to inputs of NAND gate 1842 whose output is connected to an input of inverter 1844. The output of unit 1844 is connected to an enabling input of tri-state buffer 1846.

Lead RSS5* is connected to three inputs of buffer 1846, while RSS6* is conneted to a fourth input. The output of this buffer is connected to leads MB12-MB15. Leads PC∅-PCF are connected to inputs of tri-state buffers 1848, 1850, 1852 and 1854, while the outputs of tri-state buffers 1848 and 1850 are connected to leads DB∅-DB7. The outputs of tri-state buffers 1852 and 1854 are connected to leads DB∅-DB7. Lead SB46 is connected to enabling inputs of tristate buffers 1848 and 1850, while lead STB47 is connected to enabling inputs of tri-state buffers 1852 and 1854. The operation of the circuity of FIG. 10 is as follows:

A signal present on lead STB27 functions to strobe the number contained in latches 1830 and 1832 into comparators 1834 and 1836, to be compared with the actual scan number fed to comparators 1834 and 1836 by leads SC∅-SC7. When the numbers are found to be equal, flip flop 1838 is toggled and produces a signal on lead EOP* which indicates that a full pellet has been scanned. For example, in the preferred embodiment of the invention the binary number contained in latches 1830 and 1832 is decimal 220. Leads RSS6* and RSS5* trigger tri-state buffer 1846 to transmit the four-bit word present at leads 2, 4, 6 and 10 to leads MB12-MB15 respectively. This information is transmitted in parallel with the other information transmitted on other leads of the MB bus to identify the information on the other leads. Signals present on leads STB46 and STB47 strobe information present on the PC bus into the DB bus at two different times.

Figure 23:
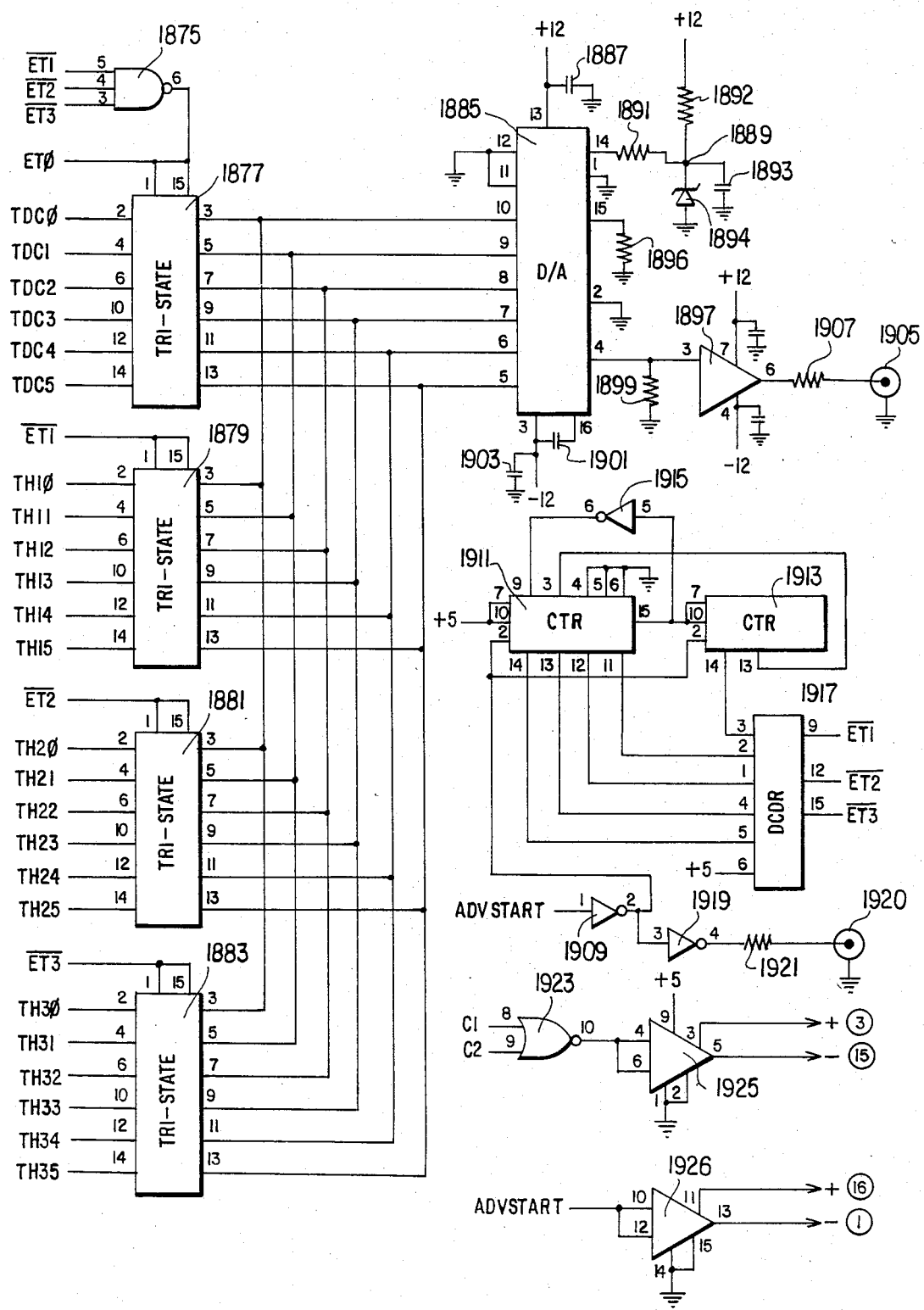
FIG. 23 illustrates circuitry for converting certain digital signals into analog signals and for multiplexing the latter for further transmission.

FIG. 23 depicts circuitry which converts the digital output of flash A/D converter 307 in FIG. 25, as well as the digital values of thresholds $T_1$, $T_2$ and $T_3$, into analog signals and multiplexes the signals for transmission to an oscilloscope. Leads ET1*, ET2* and ET3* are each connected to inputs of NAND gate 1875, the output of which is connected to an enabling input of tri-state buffer 1877. Also connected to an enabling input of tri-state buffer 1877 is lead ET0*. Pins 3, 5, 7 9, 11 and 13 of tri-state buffers 1877, 1879, 1881 and 1883 are all connected together in parallel and further connected to inputs of digital-toanalog [D/A]converter 1885. Leads TDC∅-TDC5 are Connected to other input terminals of tri-state buffer 1877. Leads TH10-TH15 are connected to other terminals of tri-state buffer 1879. Leads TH20-TH25 are connected to other terminals of tri-state buffer 1881 and leads TH30-TH35 are connected to other inputs of tri-state buffer 1883.

Leads ET1*, ET2* and ET3* are connected to enabling inputs of tri-state buffers 1879, 1881 and 1883 respectively. Pins 11 and 12 of D/A converter 1885 are connected to ground. Pin 13 is connected to the 12 volt power supply, as well as to ground through capacitor 1887. Pin 14 is connected to node 1889 through resistor 1891. Node 1889 is connected to the 12 volt power supply through resistor 1892, as well as to ground through capacitor 1893 and to ground through Zener diode 1894. Pin 1 of D/A converter 1885 is connected to ground. Pin 15 is connected to ground through resistor 1896. Pin 2 is connected to ground. Pin 4 is connected to an input of operational amplifier 1847, as well as to ground through resistor 1899. Pin 16 is connected to pin 3 by means of capacitor 1901 and pin 3 is connected to the negative 12 volt power supply, as well as ground by means of capacitor 1903. The output of operational amplifier 1897 is connected to a terminal 1905 through resistor 1907. Terminal 1905 is dapted to be coinnected to an oscilloscope [not shown].

Lead ADVSTART is connected to an input of inverter 1909 the output of which is connected to clocking inputs of counters 1911 and 1913. Enabling inputs of counter 1913 are connected to the loading input of counter 1911 by means of inverter 1915. The outputs of counters 1911 and 1913 are connected to decoder 1917, the outputs of which are connected to leads ET1*, ET2* and ET3*. The output of inverter 1909 is further connected to an input of inverter 1919 whose output is connected to a terminal 1920 through resistor 1921. Terminal 1920 is adapted to be connected to a triggering input of an oscilloscope [not shown]. Leads C1 and C2 are connected to inputs of NOR gate 1923 the output of which is connected to driver 1925. Lead ADV-START is further connected to the inputs of driver 1926. Drivers 1925 and 1926 function to start the scanning sequence of the photodiode array and to supply the array with clock pulses.

The operation of the above-described circuitry is as follows: Counters 1911 and 1913 together with decoder 1917 provide a repeating sequence of pulses on leads ET1*, ET2* and ET3*. These latter leads, together with the output of NAND gate 1875 provide timing signals which sequentially trigger tri-state buffers 1877, 1879, 1881 and 1883. Thus, the inputs of these tri-state buffers are separately and sequentially fed to the input of D/A converter 1885 whose output appears as an analog signal at terminal 1905 by way of operational amplifier 1897. Therefore, the weighted photodiode signal present on leads TDC∅-TDC5, as well as the threshold signals of thresholds T$_1$, T$_2$ and T$_3$ present on leads TH1∅-TH15, TH2∅-TH25 and TH3∅-TH35, are multiplexed into D/A converter 1885 which allows an output signal is provided at terminal 1905 which allows simultaneous oscilloscope display of the four signals.

Figure 24A:
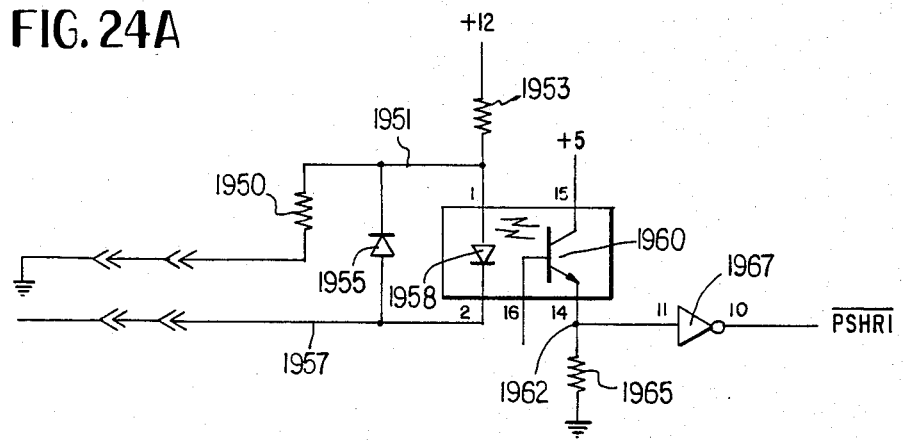
FIG. 24A and 24B illustrate pusher detector circuitry.
Figure 24B:
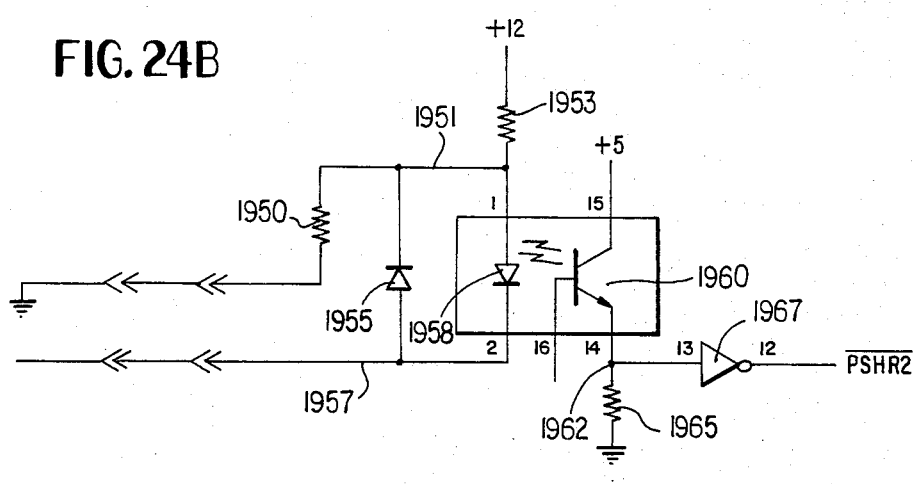

FIG. 24 illustrates pusher detector circuitry. Two circuits are shown, namely those of FIG. 24A and FIG. 24B. These are substantially identical except for the fact that the input of FIG. 24A is connected to pusher 1 and the input of FIG. 24B is connected to pusher 2. Further, the output of the circuit of FIG. 24A is designated PSHR1*, while the output of the circuit of FIG. 24B is designated PSHR2*. The following description therefore applies to both FIG. 24A and 24B.

One terminal of resistor 1950 is connected to ground while the other terminal is connected to node 1951. Node 1951 is connected to the 12 volt positive power supply by resistor 1953. Diode 1955 is connected between node 1955 and node 1957 which is the lead providing the signal from pusher 1. Light-emitting diode [LED]1958 is connected between nodes 1951 and 1957 and with polarity opposite that of diode 1955. The base of a photo-transistor 1960 is connected to lead 16. The collector of photo-transistor 1960 is connected to the 5 volt positive voltage supply and its emitter is connected to node 1962. Node 1962 is connected to ground through resistor 1965, as well as to an input of inverter 1967 the output of which is connected to lead PSHR1*.

The operation of the circuit of FIGS. 24A and 24B is as follows:

With reference to FIG. 24A, the metal body of one of the two pushers [not shown]approaches a transducer [not shown]which may comprise an eddy current coil fixed to a stationary support. This action causes signal to be applied to node 1957 and thence to LED 1958. Light produced by LED 1958 is transmitted to the phototransistor and serves to modulate the current flowing through resistor 1965. Thus it produces a voltage signal at node 1962 which is indicative of the position of the pusher. Diode 1955 protects LED 1958 in the event that an excessive voltage is applied to node 1957. The use of LED 1958 and phototransistor 1960 isolates the signal produced at node 1962 from noise present at node 1957. The operation of the circuitry of FIG. 24B is substantially the same, but is applicable to the other pusher.

Figure 4B:
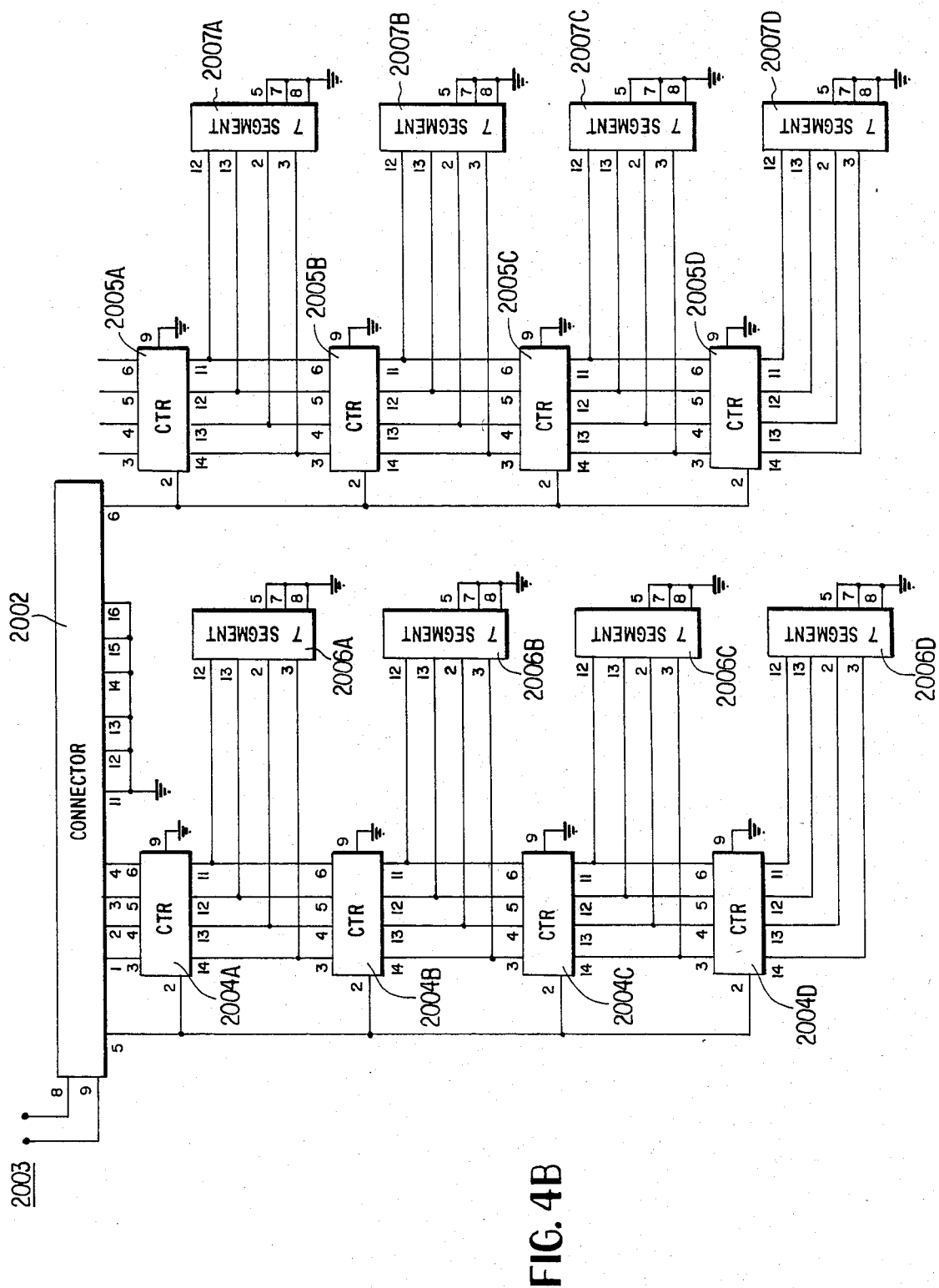
FIG. 4B illustrates circuitry for generating operating signals to an external transducer.

FIG. 4B depicts circuitry which generates operating signals to an external transducer. Connector 2002 is connected to enabling switch 2003. A lead of connector 2002 is connected to clocking inputs of counters 2004a-2004d. Another lead of connector 2002 is connected to the clocking inputs of counters 2005a-2005d. Terminals 1-4 of the connector are connected to the inputs of counters 2004a and 2005a.

The outputs of counter 2004a are connected to the inputs of counter 2004b; the outputs of counter 2004b are connected to the inputs of counter 2004c; and the outputs of counter 2004c are connected to the inputs of counter 2004d.

The outputs of counter 2005a are connected to the inputs of counter 2005b; the outputs of counter 2005b are connected to the inputs of counter 2005c; and the outputs of counter 2005c are connected to the inputs of counter 2005d.

The outputs of conters 2004a-2004c are further connected to the inputs of seven segment display [SSD's] 2006a-2006c, respectively. The outputs of counter 2004d are connected to the inputs of SSD 2006d. The outputs of counters 2005a-2005c are further connected to the inputs of SSD's 2007a-2007c, respectively, and the outputs of counter 2005d are connected to the inputs of SSD 2007d. Pins 5, 7 and 8 of SSD's 2006a-2006d and of SSD's 2007a-2007d are connected to ground. In FIG. 4A, leads BB∅-BB3, STB1C and STB1D are connected to inputs of tri-state buffer 2008. The output of buffer 2008 is connected to inputs of connector 2002, which is also shown in FIG. 4B.

In the operation of the circuit of FIG. 4B, the successful sending or receipt of selected signals on the BB bus is indicated by the output of the SSD's. The output is indicative of the signals present on leads BB∅-BB3 and the output is coded to indicate the type of signal sent or received on the bus.

FIG. 19 depicts circuitry for generating signals availale to an operator which indicate the operation of preprocessor circuitry. The following leads, herein terms "monitoring leads", namely, LEDTRACK*, TS∅*, TS1*, XFRENBL*, 8KEMPTY, 8KOVFL*, SYSMEM* MS4*, MS8*, LEDTRACK*, TKVCORRL, T1VIDEO, T2VIDEO, T3VIDEO, MSG*, and ICG*, are connected to inputs of inverters 2050a-2050p respectively. The outputs of inverters 2050a-2050p are each connected to the 5 volt power supply through resistors 2052a-2052p respectively. The outputs of inverters 2050a-2050i are further connected to inputs of LED's 2054a-2054i, whose outputs are connected to ground. The outputs of inverters 2054j-2054p are further connected to leads TP1-TP7 respectively.

Lead CP1* is connected to an input of inverter 2056, the output of which is connected to lead C1. Lead CP1 is connected to each input of four inverters 2058a–2058d whose outputs are each connected to lead C1*. Lead CP2* is connected to an input of inverter 2060, the output of which is connected to lead C2. Lead CP2 is connected to each of two inputs of inverters 2062a and 2062b whose outputs are connected to leads C2*. Lead CP3* is connected to an input of inverter 2064, the output of which is connected to lead C3. Lead CP3 is connected to each input of two inverters 2066a and 2066b, the outputs of which are connected to lead C3*. Lead CP4* is connected to an input of inverter 2068, the output of which is connected to lead C4. Lead CP4 is connected to each of two inputs of inverters 2070a and 2070b whose outputs are connected to lead C4*. Lead CP5* is connected to an input of inverter 2072 whose output is connected to lead C5. Lead C5 is connected to an input of inverter 2074, the output of which is connected to lead C5*.

In operation of the circuit of FIG. 19, the signals on some of the monitoring leads are manifest as optical signals by LED's 2054a–2054i. The signals on the rest of the monitoring leads are transmitted to leads TP1–TP7 for connection to external monitoring circuitry. The inverters interposed between the CP bus and the C bus function to invert signals on the CP bus, as well as to provide current sources to accommodate circuit fan-out.

Figure 21:
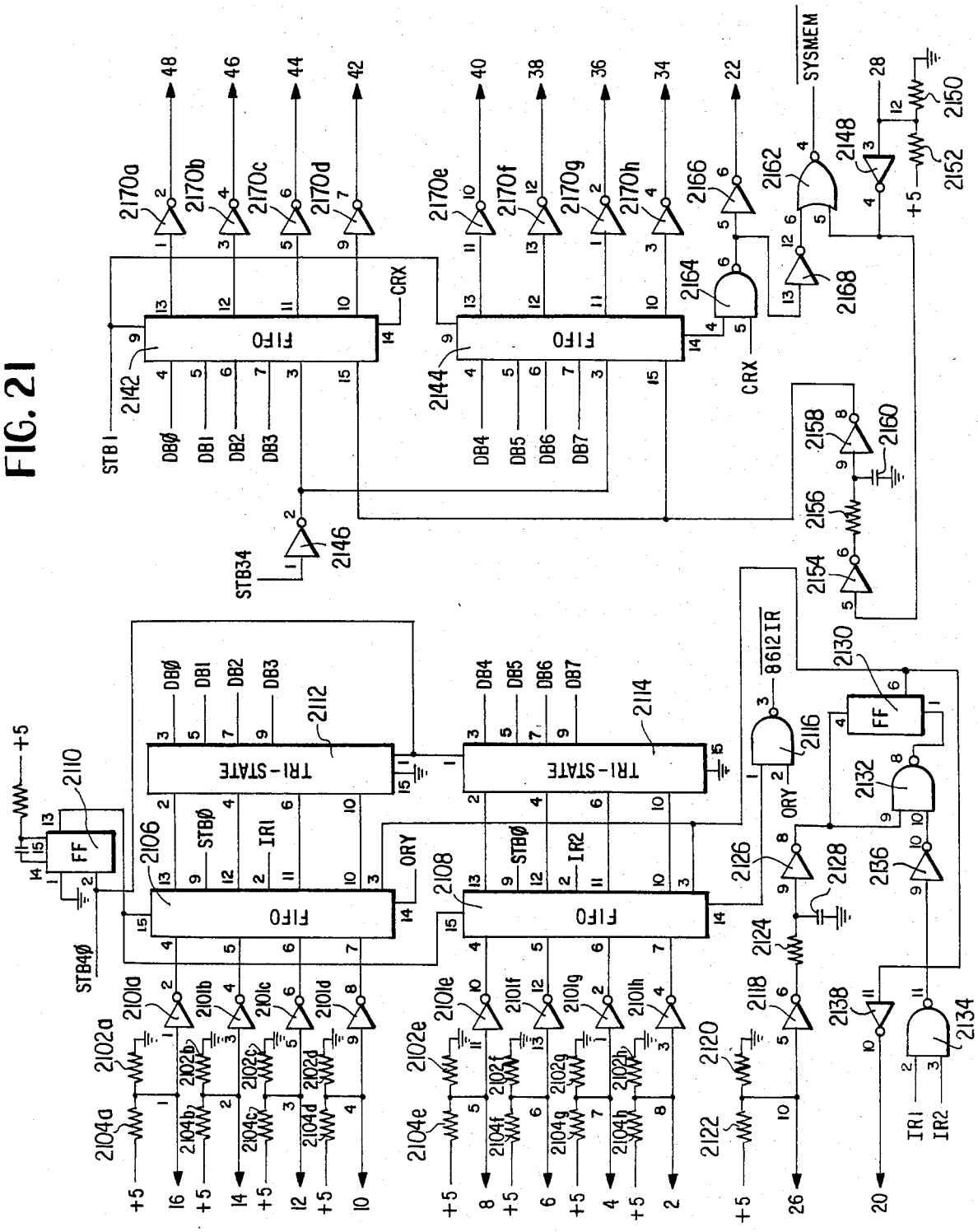
FIG. 21 illustrates circuitry comprising the executive controller.

FIG. 21 illustrates circuitry comprising the executive controller. The inputs of inverters 2101a–2101h are connected to input/output connectors 16, 14, 12, 10, 8, 6, 4 and 2 respectively. The inputs of these inverters are further connected to ground by means of resistors 2102a–2102h respectively and to the 5 volt positive voltage supply through resistors 2104a–2104h respectively. The outputs of inverters 2101a–2101h are connected to inputs of first-in-first-out [FIFO] memories 2106 and 2108. These memories have a capacity of 64 bits. The outputs of FIFO's 2106 and 2108 are connected to the setting input of flip flop 2110, the input of which is connected to lead STB40. Lead STB40 is also connected to enabling inputs of tri-state buffers 212 and 2114. The outputs of FIFO memories 2106 and 2108 are connected to terminals of tri-state buffers 2112 nd 2114 the outputs of which are connected to leads DB0–DB7.

An output of FIFO 2108 is connected to an input of NAND gate 2116 the other input of which is connected to lead ORY. The output of this NAND gate is connected to lead 8612IR*. The input of inverter 2118 is connected to input/output connector number 26, as well as to ground through a resistor 2120 and to the 5 volt positive power supply through resistor 2122. The output of inverter 2120 is connected to one terminal of resistor 2124, the other terminal of which is connected to an input of inverter 2126. The input of inverter 2126 is further connected to ground through capacitor 2128. The output of inverter 2126 is connected to a resetting input of flip flop 2130, as well to an input of NAND gate 2132 whose output is connected to a setting input of flip flop 2130. Leads IR1 and IR2 are connected to inputs of NAND gate 2134, the output of which is connected to an input of inverter 2136. The output of unit 2136 is connected to an input of NAND gate 2132. The output of flip flop 2130 is connected to an input of inverter 2138 whose own output is connected to lead 20 of an input/output connector. The output of flip flop 2130 is further connected to latching terminals of FIFO memories 2106 and 2108.

Leads DB0–DB7 are connected to inputs of 64 bit FIFO memories 2142 and 2144. Lead STB34 is connected to latching inputs of these chips by means of inverter 2146. Lead 28 of input/output connector is connected to an iuput of inverter 2148. The input of inverter 2148 is further connected to ground through resistor 2150 and to the 5 volt positive power supply by resistor 2152. The output of inverter 2148 is connected to the input of inverter 2154 whose own output is connected to one terminal of resistor 2156. The other terminal of the latter resistor is connected to the input of inverter 2158. The input of inverter 2158 is further connected to ground by capacitor 2160. The output of inverter 2158 is further connected to pins 15 of FIFO memories 2142 and 2144. The output of inverter 2148 is futher connected to an input of NOR gate 2162 whose output is connected to lead SYSMEM*.

An output of FIFO memory 2144 is connected to an input of NAND gate 2164 the other input of which is connected to lead ORX. The output of NAND gate 2164 is connected to an input of driver 2166 the output of which is connected to input/output connector 22. The input of driver 2166 is further connected to an input of inverter 2168, the output of which is connected to an input of NOR gate 2162. The outputs of FIFO memories 2142 and 2144 are connected to inputs of inverters 2170a–2170h whose outputs are connected to input/output connector leads 48, 46, 44, 42, 40, 38, 36 and 34 respectively. Lead STB1 is connected to an enabling input of each of FIFO memories 2142 and 2144.

The operation of the above-described circuitry is as follows: Resistors 2104a–2104h function in an impedance matching capacity and to minimize noise. A signal on lead 26, delayed by resistor 2124 and capacitor 2128, latches the signals present on the eight inputs of FIFO's 2106 and 2108 into these FIFO's STB0 shifts the data, in parallel, within the FIFO's. The data present in the FIFO's is read out onto the DB bus through latches 2112 and 2114.

FIFO's 2142 and 2144 function in a symmetrical manner to store in parallel eight-bit groups of data inputted by the DB bus and to then feed the data to inverters 2170a–2170h.

Information fed into FIFO's 2106 and 2108 is relevant to decision making. The output of FIFO's 2142 and 2144 contains information relevant to sorting actions to be taken with respect to the pellets.

Figure 30:
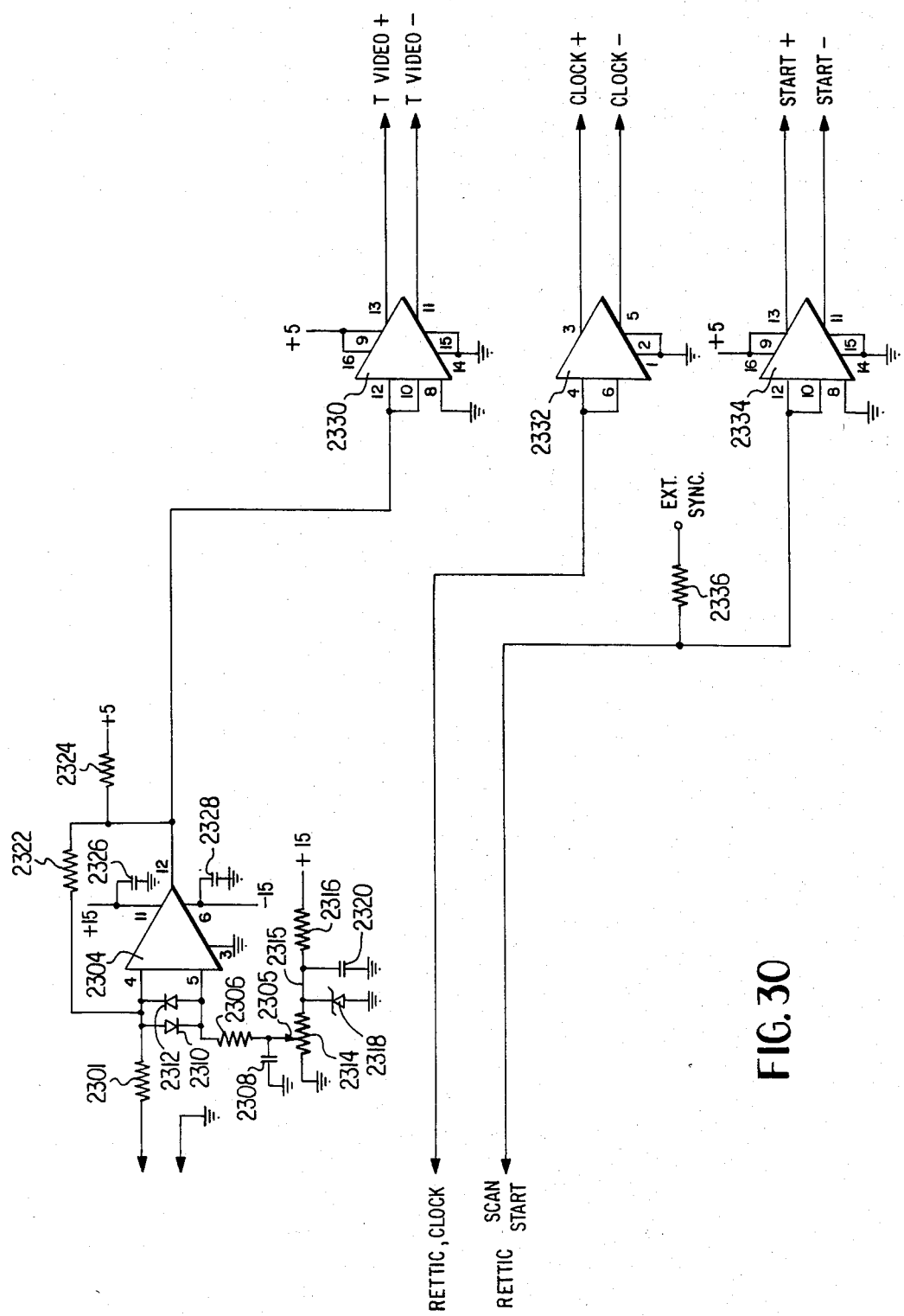
FIG. 30 illustrates a portion of circuitry for making diameter measurement computations.
Figure 31:
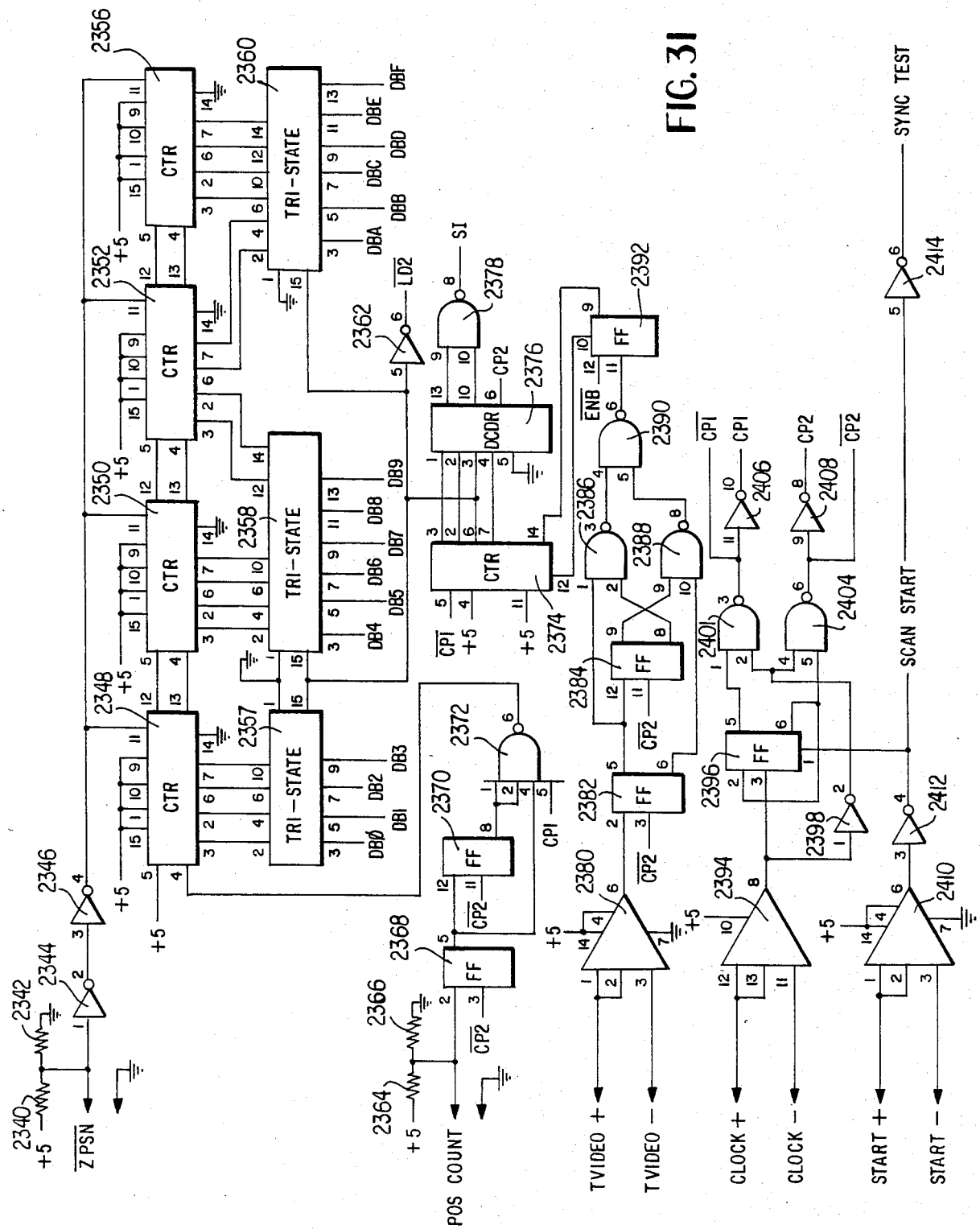
FIG. 31 illustrates another portion of circuitry for making diameter measurement computations.
Figure 32:
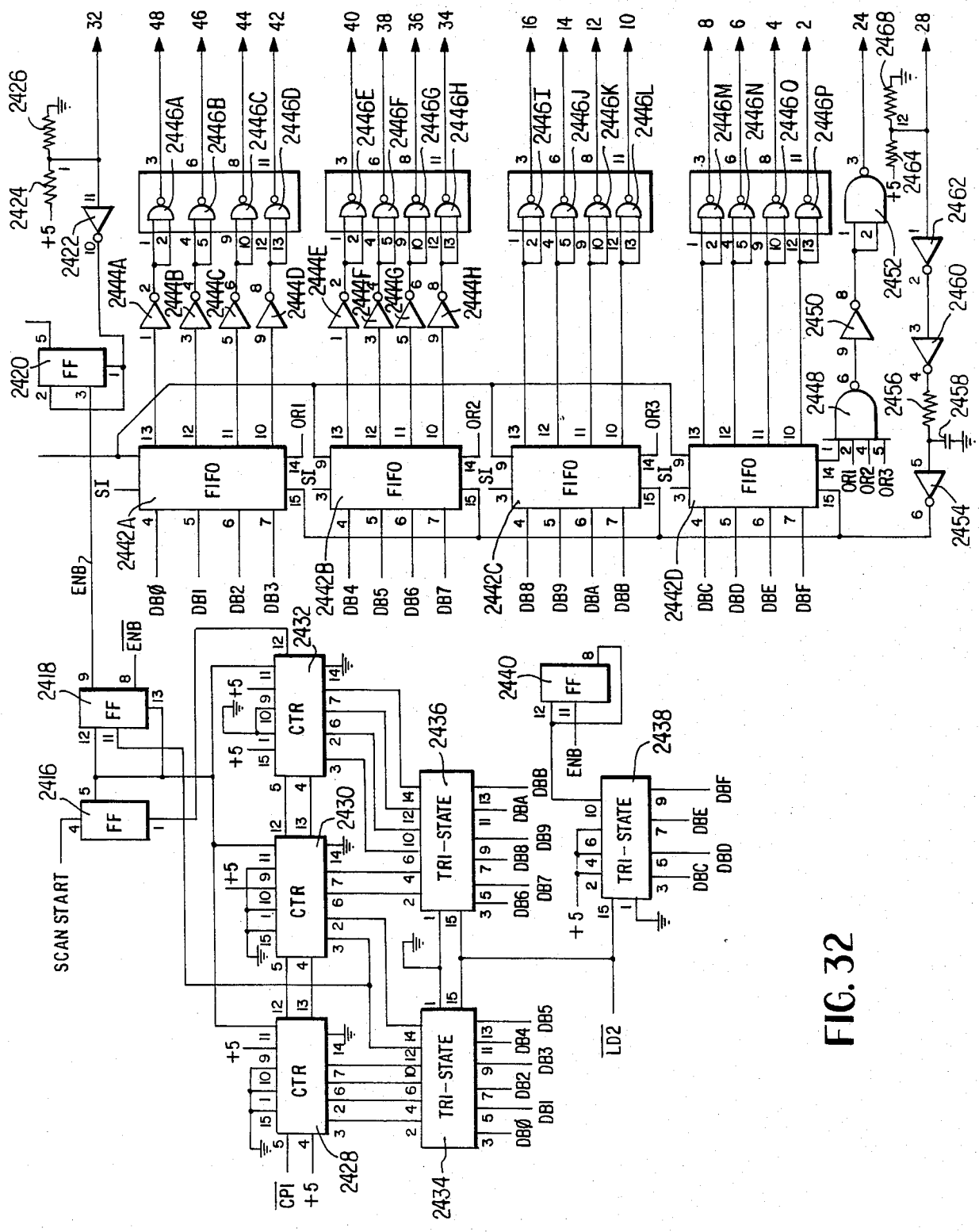
FIG. 32 illustrates a further portion of circuitry for making diameter measurement computations.

FIGS. 30, 31 and 32 illustrate circuitry utilized in conjunction with photodiode array 380 in FIG. 29 to make diameter measurement computations. In FIG. 30 one terminal of resistor 2301 is connected to an input of comparator 2304. The other input of comparator 2304 is connected to a tap 2305 of variable resistor 2314 by means of resistor 2306. The tap 2305 is also connected to ground. by capacitor 2308. One terminal of variable resistor 2314 is connected to ground while the other terminal is connected to node 2315. Node 2315 is connected to ground by Zener diode 2318 and by capacitor 2320. Node 2315 is also connected to the 15 volt positive power supply by resistor 2316. The two inputs of comparator 2304 are connected to each other by back-to-back diodes 2310 and 2312. The output of comparator 2304 is connected to the terminal of resistor 2301 which is connected to the comparator's input by resistor 2322 and the output is also connected to the 5 volt positive power by resistor 2324. The output of comparator 2304 is further connected to an input of amplifier 2330 the outputs of which are connected to leads marked TVIDEO+ and TVIDEO−.

A lead marked RETTIC, CLOCK is connected to an input of amplifier 2332 the outputs of which are connected to leads labeled CLOCK+ and CLOCK−. A lead marked RETTIC, SCANSTART is connected to the inputs of amplifier 2334 the outputs of which are connected to leads START+ and START−. The input of this amplifier is also connected to a lead marked EXT. SYNC through resistor 2336.

In FIG. 31 lead ZPSN* is connected to the input of inverter 2344. This input is connected to ground by resistor 2342 and to the 5 volt positive power supply by resistor 2340. The output of inverter 2344 is connected to an input of inverter 2346 the output of which is connected to the inputs of counters 2348, 2350, 2352 and 2356. The outputs of these counters are connected to inputs of tri-state buffers 2357, 2358 and 2360. The outputs of these buffers are connected to leads DB∅–DBF. Pins 15 of these buffers are all connected to an input of inverter 2362 the output of which is conneqted to lead LD2*. The input of inverter 2362 is further connected to pin 3 of 1–8 decoder 2376.

A lead marked POS COUNT is connected to an input of flip flop 2368 the clocking input of which is connected to lead CP2*. Lead POS COUNT is further connected to ground by resistor 2366 and to the 5 volt positive power supply by resistor 2364. The output of flip flop 2368 is connected to an input of flip flop 2370 as well as to an input of NAND gate 2372. The clocking input of flip flop 2370 is connected to lead CP2*. The output of flip flop 2370 is connected to two other inputs of NAND gate 2372 the fourth input of which is connected to CP1. The output of NAND gate 2372 is connected to an input of counter 2348. Leads TVIDEO+ and TIVIDEO− are connected to inputs of amplifier 2380 the output of which is connected to an input of flip flop 2382. The clocking input of flip flop 2382 is connected to lead CP2*. One output of this flip flop is connected to an input of flip flop 2384 as well as to an input of NAND gate 2386. The clocking input of flip flop 2384 is connected to lead CP2*. The other output of this flip flop is connected to the other input of NAND gate 2386. The other output of flip flop 2382 is connected to an input of NAND gate 2388 the other input of which is connected to the other output of flip flop 2384. The outputs of NAND gates 2386 and 2388 are connected to inputs of NAND gate 2390 the output of which is connected to an input of flip flop 2392. The other input of flip flop 2392 is connected to lead ENB*. An output of flip flop 2392 is connected to an input of counter 2374 and an output of counter 2374 is connected to the presetting input of flip flop 2392. The outputs of counter 2374 are connected to inputs of decoder 2376. Two outputs of which are connected to inputs of NAND gate 2378 the output of which is connectd to lead SI. Pin 6 of this decoder is connected to lead CP2.

Leads CLOCK+ and CLOCK− are connected to inputs of amplifier 2394 the output of which is connected to the clocking input of flip flop 2396 as well as to the input of inverter 2398. One output of this flip flop is connected to an input of NAND gate 2401 and the other output is connected to an input of NAND gate 2404 as well as to an input of the same flip flop. The output of inverter 2398 is connected to the other inputs respectively of NAND gates 2401 and 2404. The output of NAND gate 2401 is connected to lead CP1* as well as to CP1 through inverter 2406. The output of NAND gate 2404 is connected to lead CP2* as well as to lead CP2 through inverter 2408. The setting input of flip flop 2396 is connected to the output of inverter 2412 the input of which is connected to the output of amplifier 2410. The inputs of this amplifier are connected to leads START+ and START−. The output of inverter 2412 is further connected to a lead marked SCAN START and thence to the input of inverter 2414 the output of which is connected to lead marked SYNC TEST.

In FIG. 32 lead SCAN START is connected to a presetting input of flip flop 2416, an output of which is connected to an input of flip flop 2418 as well as to a setting input of flip flop 2418. The setting input of flip flop 2418 is further connected to inputs of down counters 2428, 2430 and 2432. An output of down counter 2432 is connected to the setting input of flip flop 2416. Pin 3 of counter 2430 is connected to the clocking input of flip flop 2418. The outputs of down counters 2428, 2430 and 2432 are connected to inputs of tri-state buffers 2434 and 2436 the outputs of which are connected to leads DB∅–DBB. Lead LD2* is connected to inputs of tri-state buffers 2434 and 2436 as well as to an input of tri-state buffer 2438. The outputs of tri-state buffer 2438 are connected to leads DBC–DBF. An output of this latter tri-state buffer is connected to an input of flip flop 2440 the clocking input of which is connected to lead ENB and the output of which is fed back to said input. One output of flip flop 2418 is connected to lead ENB as well as to a clocking input of flip flop 2420. The other output of flip flop 2418 is connected to lead ENB*.

A lead marked 32 is connected to an input of inverter 2422 as well as to ground by resistor 2426 and to the 5 volt positive power supply by resistor 2424. The output of inverter 2422 is connected to an input of flip flop 2420 as well as to the setting input of this flip flop. An output of flip flop 2420 is connected to the latching inputs of 64 bit FIFO memories 2442a–2442d. The inputs of these FIFO's are connected to leads DB∅–DBF. An output of FIFO 2442a is connected to lead OR1, an output of FIFO 2442b is connected to lead OR2 and an output of FIFO 2442c is connected to lead OR3. An output of FIFO 2442d is connected to an input of NAND gate 2448, the other inputs of which are connected to leads OR1, OR2 and OR3. The output of NAND gate 2448 is connected to an input of inverter 2450 the output of which is connected to the inputs of NAND gate 2452. The output of gate 2452 is connected to lead 24. Outputs of FIFO's 2442a and 2442b are connected to inputs of inverters 2444a–2444h, the outputs of which are connected to inputs of NAND gates 2446a–2446h. The outputs of these NAND gates are connected respectively to pins 48, 46, 44, 42, 40, 38, 36 and 34. The outputs of FIFO's 2442c and 2442d are connected to inputs of NAND gates 2446i–2446p, the outputs of which are respectively connected to pins 16, 14, 12, 10, 8, 6 and 2. Pin 28 is connected to an input of inverter 2462 as well as to ground through resistor 2468 and to the 5 volt positive power supply by resistor 2464. The output of inverter 2462 is connected to an input of inverter 2460, the output of which is connected to the input of inverter 2454 through resistor 2456. The input of inverter 2454 is connected to ground by capacitor 2458. The output of inverter 2454 is connected to inputs of FIFO memories 2444a–2444d.

The operation of the circuits of FIGS. 30, 31 and 32 is as follows:

A signal generated by each photodiode in array 380*b* in FIG. 29 is applied to the input of comparator 2304. When this signal exceeds the threshold determined by the position of tap 2305 on variable resistor 2314 appropriate signals appear at leads TVIDEO+ and TVIDEO−. A signal appears on leads CLOCK+ and CLOCK− each time a diode is scanned and a signal appears at leads START+ and START− each time the entire array is scanned. Down counters 2428, 2430 and 2432 in FIG. 32 function to provide information as to the pellet's position along the path because the position at which the diameter measurement is made, namely at slits 368 in FIG. 29, will be different than the position at which surface feature identification is made, namely at the position indicated by bracket 370 in FIG. 28. Accordingly the down counters start at a predetermined number and count down to zero. This indicates that a corresponding position on the pellet surface formerly located at bracketed region 370 is now located at slit 368. This information is fed to the DB bus and thence to FIFO's 2442*a*–2442*d*.

Leads CP1, CP1*, CP2 and CP2* feed signals to the counters in FIG. 31 to thereby indicate the positions of transmitted light beams 373 and 374 in FIG. 29 in terms of diode addresses of photodiode array 380. Thus the length of the eclipsed region 371 and hence the pellet diameter can be determined.

In the preferred embodiment described above, the latches called out may be integrated circuit (IC) type 74161 operated in a latching mode and the counters called out may be the identical type of chip operated in a counting mode. The microprocessor is preferably an IC type 8080A-1 chip. The 1-of-8 decoders may be 1C type 8205 chips. The EPROMS may be IC type 2732 chips and RAMs 614 and 617 in FIG. 1 may be IC type 2114 chips. The bidirectional bus drivers called out in the spec may be 8216 chips. Oscillator 553 in FIG. 1 may be an IC type 8224 chip. Decoder 605 in FIG. 1 may be an IC type 8228 chip, 8-to-1 encoder-multiplexer 692 in FIG. 2F may be an IC type 74151 chip. The comparators called out may be IC type 74585 or 7485 chips. The flip flops may be IC type 7474 or 745112 chips. Delay/shift registers 1322 and 1655 in FIGS. 6 and 7 may be IC type 74164 chips; shift registers 1337 and 1650 in these Figures may be 1C type 74164 chips. Decoders 1659 and 1313 in these Figures may be IC type 74151; and the RAM's in these Figures may be IC type 2125 chips. The latter chips may also be used for the RAM's in FIGS. 20 and 22. The RAM's in FIG. 11 may be IC type 2125. The adders in FIG. 12 may be IC type 7483 chips and the FIFO's called out may be IC type 74193 chips.

Multiplier 218 in FIG. 16 may be IC type 7497. Driver-amplifiers called out may be IC type DS8832. RAM's in FIG. 18 may be IC type 2147. D/A converters called out may be IC type DAC08. Flash A/D converter 307 in FIG. 25 may be IC type TDC1014J. Buffer/amplifiers 290, 301, 304 and 812 may be IC type 2520. The above IC types refer to standard industry designations. Tri-state buffers called out may be IC type DM 8095 chips manufactured by National Semiconductor Corp.

From the foregoing discussion it will be clear that the present invention provides an automated pellet inspection system in which pellets following a substantialy continuous path are spiraled past an inspection station with a high degree of mechanical stability. The inspection station optically inspects the pellets and associated preprocessor circuitry allows high throughput with minimal denigration of inspection reliability. The system allows scrutiny of minute pellet area.

In order to cope with the large amount of data indicative of pellet characteristics which can be derived from the signals that are generated upon pellet inspection, and to permit the use of low cost, relatively low performance data processing equipment, a unique data compression technique using exception reporting is implemented, which results in collapsing the data rate. Each pellet further has a diameter measurement performed on it and is inspected for roundness and the like. The pellets are stacked in end-to-end abutment during inspection and each is identified by the interface separating it from its abutting neighbors. This is effected by the correlation of the locations of specific signal intensities and includes the generation of a track gate which identifies all data with the particular pellet from which it is derived. The reliability of inspection is further enhanced by modifying the signals derived from the optical inspection process. These signals may vary due to factors extraneous to the pellet characteristics of interest and the signal modification compensates for such variations.

From the foregoing discussion it will be clear that the automated pellet inspection system disclosed herein lends itself to numerous modifications, changes, substitutions and equivalents, and that portions of the invention may be used without the use of other parts thereof. All of these variations are deemed to fall within the scope of the invention disclosed herein and, accordingly, it is intended that the invention be limited only by the spirit and scope of the appended claims.

What is claimed is:

1. A system for inspecting a succession of discrete, substantially cylindrical pellets for conformance to predetermined criteria, including length and diameter, wherein said pellets are presented for inspection in a stack with said pellets disposed substantially coaxially and with the interfaces of said pellets in end-to-end abutment, said system comprising in combination;

transport means for advancing said stack of said pellets along a path for presentation to an optical inspection station by spiraling around the stack axis at a controlled linear and angular velocity respectively;

said optical inspection station including means for illuminating an elongated inspection region of said path while said pellets travel within the limits of a stationary viewing region, said elongate portion of said path exceeding in length that of at least a single pellet;

a linear array of photosensitive elements, disposed in said stationary viewing region, each photosensitive element adapted to provide an output signal as a function of the intensity of light reflected thereto from said illuminated pellets; and means for periodically scanning said output signals to derive a video signal from successive scans representative of selective characteristics of each pellet under inspection; and a first preprocessing circuit, including:

means for extracting data from said video signal indicative of said conformance of the pellet under inspection to said predetermined criteria;

means for compressing said extracted data to collapse the rate at which preprocessed data is provided for further data processing;

means for normalizing said video signal to compensate for signal variations caused by factors extraneous to the inspection of said pellets for conformance to said criteria;

means responsive to said video signal for detecting each of said interfaces as a plurality of diminished video signal amplitudes each occurring at the same selective array position during a plurality of scans;

means responsive to said detecting means for generating a track gate by selecting signals corresponding to a group of successive array elements whose output signals correspond to illumination received from a single pellet; and means responsive to the linear velocity of said single pellet for advancing said track gate;

whereby said track gate tracks the interfaces of said linearly moving single pellet and continuously brackets the signals corresponding to said pellet by means of leading and trailing track gate edges.

2. A surface preprocessing circuit in accordance with claim 1 and further comprising:

means for determining the distance between the bracketing pair of interfaces for each pellet under inspection as a measure of its actual length dimension;

means for comparing said actual and predetermined pellet length dimensions;

means responsive to said comparing means for locating each of said track gate edges in the center of its corresponding interface if said actual length dimension falls within a predetermined range of said predetermined length dimension;

means responsive to a determination by said comparing means of an actual length dimension outside said range for locating said leading track gate edge at the center of the interface between the pellet under inspection and the previously tracked pellet; and means for spacing the trailing track gate edge for said pellet under inspection behind said last-recited leading edge a distance equal to said predetermined pellet length dimension.

3. A surface preprocessing circuit in accordance with claim 2 and further comprising:

means for locating the trailing track gate edge for the first pellet in said stack at the center of the interface between said first pellet and the subsequent pellet of said stack;

means for spacing the leading track gate edge for said first pellet forward from its corresponding trailing track gate edge a distance equal to said predetermined pellet length dimension;

means for locating the leading track gate edge for the last pellet in said stack at the center of the interface between said last pellet and the preceeding pellet of said stack; and means for spacing the trailing track gate edge for said last pellet behind its corresponding leading track gate edge a distance equal to said predetermined pellet length dimension.

4. A surface preprocessing circuit in accordance with claim 3 wherein said angular and linear velocities are selected to provide at least one complete revolution of each spiraling pellet while traversing the length of said window, the cylindrical surface of each pellet being inspected at intervals dependent on the selected scan rate and scan period;

said surface preprocessing circuit further comprising:

means for detecting amplitude changes of said video signal in excess of a predetermined threshold, each crossing of said last-recited threshold being indicative of a transition between light and dark surface portions on the inspected pellet surface;

means for correlating said transitions with the pellet defined by the corresponding track gate;

means for determining the axial coordinate of each correlated transition on its pellet surface by the location of the corresonding photosensitive device within said linear array;

means dependent on said angular velocity and on a selected circumferential reference on said pellet surface for determining the circumferential coordinate of each correlated transition on said pellet surface;

and means for storing the coordinates of each of said transitions as extracted data indicative of the condition of said pellet surface;

whereby the volume of data contained in said video signal is compressed.

5. A system for inspecting a succession of discrete, substantially cylindrical pellets for conformance to predetermined criteria, said system comprising:

transport means for advancing a stack of said pellets disposed in substantially coaxial, end-to-end abutment for presentation to an optical inspection station to inspect each pellet;

said optical inspection station including means for illuminating an elongated inspection region of said path while said pellets travel within the limits of a stationary viewing region, said elongate illuminated region exceeding in length the length of any single pellet;

a linear array of photosensitive devices each adapted to provide an output signal as a function of the intensity of light reflected thereto from said illuminated pellets; and means for periodically scanning said output signals to derive a video signal from successive scans;

a first preprocessing circuit, comprising:

means responsive to said video signal for detecting each of said pellet end-to-end abutments as a plurality of diminished video signal amplitudes;

means responsive to said detecting means for generating a track gate by selecting signals corresponding to a group of successive array devices corresponding to illumination received from at least a single pellet; and means responsive to the linear velocity of said at least a single pellet for advancing said track gate;

whereby said track gate tracks at least one linearly moving pellet and continuously brackets the signals corresponding to said at least one pellet by means of leading and trailing track gate edges.

6. A preprocessing circuit in accordance with claim 5 and further comprising:

means for determining the distance between the end-to-end abutments for each pellet under inspection as a measure of its actual length dimensions;

means for comparing said actual and predetermined pellet length dimension;

means responsive to said comparing means for locating each of said track gate edges in the center of its corresponding abutment if said actual length dimension falls within a predetermined range of said predetermined length dimension;

means responsive to a determination by said comparing means of an actual length dimension outside said range for locating said leading track gate edge at the center of the abutment between the pellet under inspection and the previously tracked pellet; and means for spacing the trailing track gate edge for said pellet under inspection behind said last-recited leading edge a distance equal to said predetermined pellet length dimension.

7. A preprocessing circuit in accordance with claim 6 and further comprising:

means for locating the trailing track gate edge for the first pellet in said stack at the center of the abutment between said first pellet and the subsequent pellet of said stack;

means for spacing the leading track gate edge for said first pellet forward from its corresponding trailing track gate edge a distance equal to said predetermined pellet length dimension;

means for locating the leading track gate edge for pellet in said stack at the center of the abutment between said last pellet and the preceding pellet of said stack; and means for spacing the trailing track gate edge for said last pellet behind its corresponding leading track edge a distance equal to said predetermined pellet length dimensions.

* * * * *